United States Patent
Harding et al.

(10) Patent No.: US 10,537,611 B2
(45) Date of Patent: Jan. 21, 2020

(54) METHODS OF TREATING LUNG CANCER

(71) Applicant: Five Prime Therapeutics, Inc., South San Francisco, CA (US)

(72) Inventors: Thomas Harding, San Francisco, CA (US); Servando Palencia, San Francisco, CA (US); Li Long, Lafayette, CA (US); Kevin Hestir, Kensington, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/003,590

(22) Filed: Jun. 8, 2018

(65) Prior Publication Data
US 2019/0000920 A1    Jan. 3, 2019

Related U.S. Application Data

(62) Division of application No. 14/357,336, filed as application No. PCT/US2012/064772 on Nov. 13, 2012, now Pat. No. 10,016,484.

(60) Provisional application No. 61/616,761, filed on Mar. 28, 2012, provisional application No. 61/559,259, filed on Nov. 14, 2011.

(51) Int. Cl.
| | | |
|---|---|---|
| *A61K 38/17* | (2006.01) | |
| *A61K 45/06* | (2006.01) | |
| *A61K 39/395* | (2006.01) | |
| *A61K 45/00* | (2006.01) | |
| *C07K 14/71* | (2006.01) | |
| *C12Q 1/6813* | (2018.01) | |
| *C12Q 1/686* | (2018.01) | |
| *G01N 33/50* | (2006.01) | |

(52) U.S. Cl.
CPC .......... *A61K 38/179* (2013.01); *A61K 39/395* (2013.01); *A61K 45/00* (2013.01); *A61K 45/06* (2013.01); *C07K 14/71* (2013.01); *C12Q 1/686* (2013.01); *C12Q 1/6813* (2013.01); *G01N 33/5005* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,229,501 A | 7/1993 | Keifer et al. |
| 5,288,855 A | 2/1994 | Bergonzoni et al. |
| 5,474,914 A | 12/1995 | Spaete |
| 5,486,462 A | 1/1996 | Rutter et al. |
| 5,707,632 A | 1/1998 | Williams et al. |
| 5,750,371 A | 5/1998 | Senoo et al. |
| 5,767,250 A | 6/1998 | Spaete |
| 5,863,888 A | 1/1999 | Dionne et al. |
| 6,255,454 B1 | 7/2001 | Keifer et al. |
| 6,344,546 B1 | 2/2002 | Dionne et al. |
| 6,350,593 B1 | 2/2002 | Williams et al. |
| 6,355,440 B1 | 3/2002 | Williams et al. |
| 6,384,191 B1 | 5/2002 | Williams et al. |
| 6,517,872 B1 | 2/2003 | Yayon et al. |
| 6,656,728 B1 | 12/2003 | Kavanaugh et al. |
| 6,844,168 B1 | 1/2005 | Keifer et al. |
| 7,135,311 B1 | 11/2006 | David et al. |
| 7,297,493 B2 | 11/2007 | Lorenzi et al. |
| 7,297,774 B2 | 11/2007 | Ullrich et al. |
| 7,645,609 B2 | 1/2010 | Follstad |
| 7,678,890 B2 | 3/2010 | Bosch et al. |
| 7,947,811 B2 | 5/2011 | Pereira et al. |
| 7,982,014 B2 | 7/2011 | Williams et al. |
| 8,119,770 B2 | 2/2012 | Blanche et al. |
| 8,173,134 B2 | 5/2012 | Bosch et al. |
| 8,338,569 B2 | 12/2012 | Marshall et al. |
| 8,481,038 B2 | 7/2013 | Keer |
| 8,501,191 B2 | 8/2013 | Williams et al. |
| 8,580,936 B2 | 11/2013 | Williams et al. |
| 2004/0063910 A1 | 4/2004 | Kavanaugh et al. |
| 2004/0115768 A1 | 6/2004 | Follstad |
| 2005/0043233 A1* | 2/2005 | Stefanic ............... A61K 31/404 514/418 |
| 2005/0187150 A1 | 8/2005 | Mohammadi et al. |
| 2006/0234347 A1 | 10/2006 | Harding et al. |
| 2006/0286102 A1 | 12/2006 | Jin et al. |
| 2007/0248604 A1 | 10/2007 | Desnoyers et al. |
| 2007/0248605 A1 | 10/2007 | Hestir et al. |

(Continued)

FOREIGN PATENT DOCUMENTS

| | | |
|---|---|---|
| EP | 0545343 A1 | 6/1993 |
| EP | 1910542 B2 | 2/2009 |

(Continued)

OTHER PUBLICATIONS

Gatius et al., "FGFR2 alterations in endometrial carcinoma," Modern Pathology, 2011, 24:1500-1510.

(Continued)

*Primary Examiner* — Elly-Gerald Stoica
(74) *Attorney, Agent, or Firm* — McNeill Baur PLLC

(57) ABSTRACT

Methods of treating cancers comprising FGFR1 gene amplification are provided. In some embodiments, the methods comprise administering a fibroblast growth factor receptor 1 (FGFR1) extracellular domain (ECD) and/or an FGFR1 ECD fusion molecule. In some embodiments, the methods comprise administering a fibroblast growth factor receptor 1 (FGFR1) extracellular domain (ECD) and/or an FGFR1 ECD fusion molecule in combination with at least one additional therapeutic agent.

20 Claims, 15 Drawing Sheets

Specification includes a Sequence Listing.

(56) References Cited

U.S. PATENT DOCUMENTS

| | | | |
|---|---|---|---|
| 2008/0171689 | A1 | 7/2008 | Williams et al. |
| 2010/0111873 | A1 | 5/2010 | Russell et al. |
| 2012/0128672 | A1 | 5/2012 | Keer |
| 2012/0183541 | A1 | 7/2012 | Brennan et al. |
| 2012/0237511 | A1 | 9/2012 | Long et al. |
| 2012/0251538 | A1 | 10/2012 | Harding et al. |
| 2013/0004492 | A1 | 1/2013 | Marshall et al. |
| 2013/0324701 | A1 | 12/2013 | Williams et al. |
| 2014/0056891 | A1 | 2/2014 | Keer |
| 2014/0140995 | A1 | 5/2014 | Williams et al. |
| 2014/0227263 | A1 | 8/2014 | Harding et al. |

FOREIGN PATENT DOCUMENTS

| | | | |
|---|---|---|---|
| EP | 2083081 | A1 | 7/2009 |
| WO | 9100916 | | 1/1991 |
| WO | 9111459 | | 8/1991 |
| WO | 2002094852 | | 11/2002 |
| WO | 2004110487 | A1 | 12/2004 |
| WO | 2005113596 | A2 | 12/2005 |
| WO | 2005115363 | A2 | 12/2005 |
| WO | 2006081430 | A2 | 8/2006 |
| WO | 2006113277 | A2 | 10/2006 |
| WO | 2007014123 | A2 | 2/2007 |
| WO | 2007059574 | A1 | 5/2007 |
| WO | 2007134210 | A2 | 11/2007 |
| WO | 2008065543 | A2 | 6/2008 |
| WO | 2008118877 | A2 | 10/2008 |
| WO | 2008133873 | | 11/2008 |
| WO | 2009133101 | | 11/2009 |
| WO | 2010017198 | | 2/2010 |
| WO | 2011034940 | | 3/2011 |
| WO | 2011060333 | A1 | 5/2011 |
| WO | 2011084711 | | 7/2011 |
| WO | 2012068030 | | 5/2012 |
| WO | 2012125812 | A1 | 9/2012 |
| WO | 2012177481 | A2 | 12/2012 |
| WO | 2013074492 | | 5/2013 |
| WO | 2014179448 | | 11/2014 |

OTHER PUBLICATIONS

Gelsi-Boyer et al., "Comprehensive Profiling of 8p11-12 Amplification in Breast Cancer," Mol Cancer Res 2005;3(12): 655-667.
Genbank Accession No. Q90330, Nov. 1, 1996, 6 pages.
Genbank Accession No. X76885, 1994, 2 pages.
Gowardhan et al., "Evaluation of the fibroblast growth factor system as a potential target for therapy in human prostate cancer" British Journal of Cancer, vol. 92, Jan. 18, 2005, pp. 320-327.
Grossman et al., "Expression of human thyrotropin in cell lines with differentglycosylation patterns combined with mutagenesis of specific glycosylation sites" J.Biol. Chem., vol. 270, No. 49, Dec. 8, 1995, pp. 29378-29385.
Guillonneau et al., "Fibroblast growth factor (FGF) soluble receptor 1 acts as anatural inhibitor of FGF2 neurotrophic activity during retinal degeneration" Molecular Biology of the Cell, vol. 9, Oct. 1998, pp. 2785-2802.
Hanneken et al., "Identification of soluble forms of the fibroblast growth factorreceptor in blood" Proc. Natl. Acad. Sci., vol. 91, Sep. 1994, pp. 9170-9174.
Hanneken et al., "Soluble forms of the high-affinity fibroblast growth factor receptor in human vitreous fluid" Investigative Opthalmology & Visual Science, vol. 36, No. 6, May 1995, pp. 1192-1196.
Hanneken et al., "Structural characterization of the circulating soluble FGF receptors reveals multiple isoforms generated by secretion and ectodomain shedding" FEBS Letters, vol. 489, 2001, pp. 176-181.
Harding et al., "Blockade of Nonhormonal Fibroblast Growth Factors by FP-1039 Inhibits Growth of Multiple Types of Cancer," Science Translational Medicine, Mar. 2013, 5:178ra39 , pp. 1-9.

Harding et al., "Blockade of Nonhormonal Fibroblast Growth Factors by FP-1039 Inhibits Growth of Multiple Types of Cancer," Sci Transl Med, 2013, 5:178ra39, Supplemental Materials, 28 pages.
Harding et al., "Preclinical efficacy of fibroblast growth factor ligand trap HGS1036 in lungcarcinoma models with genomic amplification of FGFR1" Poster from AACR Annual Meeting, Mar. 31-Apr. 4, 2012, 1 page.
Harding et al., "Role of VEGF, PDGF and FGF in glioblastoma progression asdetermined by soluble decoy receptor expression in preclinical models" Cell Genesys, Inc., Abstract No. 3030, presented at the AACR Annual Meeting, Apr. 16-20, 2005, 1 page.
Harding et al., "Preclinical Efficacy of FP-1039 (FGFR1:Fc) in Endometrical Carcinoma Models with Activating Mutations in FGFR2," AACR 101st Annual Meeting Poster (Apr. 17-21, 2010).
Hoda et al., Evaluation of the fibroblast growth factor receptor axis as potential therapy target in malignant pleural mesothelioma. J.Thoracic Oncology, 6, Suppl. 2, pp. S931. Abstract No. P2.020, Meeting Info: 14th World Conference on Lung Cancer. Amsterdam, Netherlands. Jul. 3, 2011-Jul. 7, 2011, ISSN: 1556-0864.
Ibrahimi et al., "Analysis of Mutations in Fibroblast Growth Factor (FGF) and a Pathogenic Mutation in FGF Receptor (FGFR) Provides Direct Evidence for the Symmetric Two-End Model for FGFR Dimerization," Mol. Cell. Biol., 25(2): 671-684 (2005).
Ibrahimi et al., "Proline to arginine mutations in FGF receptors 1 and 3 result in Pfeiffer and Muenke craniosynostosis syndromes through enhancement of FGF binding affinity," Hum. Mol. Genet., 13: 69-78 (2004).
Ibrahimi et al., "Biochemical analysis of pathogenic ligand-dependent FGFR2mutations suggests distinct pathophysiological mechanisms for craniofacial and limb abnormalities," Human Molecular Genetics, 2004, 13(19): 2313-2324.
Ibrahimi et al., "Structural basis for fibroblast growth factor receptor 2 activation inApert syndrome," PNAS, 2001, 98(13): 7182-7187.
International Preliminary Report on Patentability, dated Jan. 22, 2008, for International Application No. PCT/US2006/028597, 14 pages.
International Search Report and Written Opinion dated Apr. 1, 2013 for PCT/US2012/064772, 16 pages.
International Search Report and written Opinion dated Mar. 8, 2010 for PCT/US2009/052704, filed Aug. 4, 2009.
International Search Report and Written Opinion dated Nov. 4, 2014 for PCT/US2014/036140, 25 pages.
International Search Report and Written Opinion of the International Searching Authority, dated Apr. 12, 2012, for International Application No. PCT/US2011/060666, 20 pages.
International Search Report and Written Opinion of the International Searching Authority, dated Jan. 31, 2012, for International Application No. PCT/US2011/060661, 16 pages.
International Search Report and Written Opinion of the International Searching Authority, dated Sep. 18, 2007, or International Application No. PCT/US2006/028597, 23 pages.
International Search Report and Written Opinion, dated Feb. 4, 2011, for International Patent Application PCT/US2010/056627, 15 pages.
Invitation to Pay Additional Fees and, Where Applicable, Protest Fee, dated Dec. 31, 2012, in international Application No. PCT/US2012/64772, 2 pages.
Jang et al., "FGFR1 is amplified during the progression of in situ to invasive breast carcinoma," Breast Cancer Research, 2012, 14:R115, pp. 1-12.
Johnson et al, "The human fibroblast growth factor receptor genes: a commonstructural arrangement underlies the mechanisms for generating receptor forms that differ in their third immunoglobulin domain" Molecular and Cellular Biology, vol. 11, No. 9, Sep. 1991, pp. 4627-4634.
Johnson et al., "Diverse forms of a receptor for acidic and basic fibroblast growthfactors" Molecular and Cellular Biology, vol. 10, No. 9, Sep. 1990, pp. 4728-4736.
Kallioniemi et al., ErbB2 amplification in breast cancer analyzed by fluorescence in situ hybridization. Proc. Natl. Acad. Sci.USA, 89, 5321-5325, 1992.

(56) References Cited

OTHER PUBLICATIONS

Kan et al., "Divalent cations and heparin-heparan sulfate cooperate to controlassembly and activity of the fibroblast growth factor receptor complex" J. Biol. Chem., vol. 271, No. 42, Oct. 18, 1996, pp. 26143-26148.
Katoh, "Cancer genomics and genetics of FGFR2 (Review)," International Journal ofOncology, 2008, 33:233-237.
Katoh, "FGFR2 Abnormalities Underlie a Spectrum of Bone, Skin, and CancerPathologies," Journal of Investigative Dermatology, 2009, 129:1861-1867.
Kaufman et al., "Characterization of ligand binding to immobilized biotinylatedextracellular domains of three growth factor receptors" Anal. Biochem., vol. 211, No. 2, Jun. 1993, pp. 261-266.
Keegan et al., "Isolation of an additional member of the fibroblast growth factor receptor family, FGFR-3," PNAS, 1991, 88:1095-1099.
Keer et al., "Enrolling a Rare Patient Population: Establishing Proof of Concept for FP-1039, an FGF 'Trap,' in Endometrial Cancer Patients with the S252W FGFR2 Mutation," American Society of Clinical Oncology 2010, Annual Meeting, Jun. 4-8, 2010, Chicago, IL.
Keifer et al., "Molecular cloning of a human basic fibroblast growth factor receptorcDNA and expression of a biologically active extracellular domain in a baculovirussystem" Growth Factors, vol. 5, 1991, pp. 115-127.
Kleeff et al., "Adenovirus-mediated transfer of a truncated fibroblast growth factor(FGF) type I receptor blocks FGF-2 signaling in multiple pancreatic cancer cell lines" Pancreas, vol. 28, No. 1, Jan. 2004, pp. 25-30.
Knights & Cook, "De-regulated FGF receptors as therapeutic targets in cancer," Pharmacol Ther, 2010, 125(1):105-117.
Koudelakova et al., "Frequency of chromosome 17 polysomy in relation to CEP17 copy number in a large breast cancer cohort", Genes, Chromos. Cancer, 55, 409-417, 2016.
Kwabi-Addo et al., "The role of fibroblast growth factors and their receptors in prostate cancer" Endocrine-Related Cancer, vol. 11, No. 4, Dec. 2004, pp. 709-724.
Lazar et al., "Transforming Growth Factor alpha: Mutation of Aspartic Acid 47 and Leucine 48 Results Different Biological Activities," Mol Cell Biol, 1988, 8(3):1247-1252.
Lee et al., "Purification and complementary DNA cloning of a receptor for basicfibroblast growth factor" Science, vol. 245, No. 4913, Jul. 7, 1989, pp. 57-60.
Lee et al., "Molecular profiles of EGFR, K-ras, c-met, and FGFR in pulmonary pleomorphic carcinoma, a rare lung malignancy," J. Cancer Res. Clin. Oncol., May 28, 2011, 9 pages.
Lee et al., c-Myc copy-number gain is an independent prognostic factor in patients with colorectal cancer. PLOS One, 10, e0139727, 2015.
Levi et al., "Matrix metalloproteinase 2 releases active soluble ectodomain offibroblast growth factor receptor 1", XP-002413740, Proc. Natl. Acad. Sci., USA, vol. 93, pp. 7069-7074, (Jul. 1996).
Li et al., "Cell transformation by fibroblast growth factors can be suppressed bytruncated fibroblast growth factor receptors" Molecular and Cellular Biology, vol. 14, No. 11, Nov. 1994, pp. 7660-7669.
Adam et al., "Toward optimized front-line therapeutic strategies in patients with metastatic colorectal cancer—an expert review from the International Congress on Anti-cancer Treatment (ICACT) 2009," Annals of Oncology, 21: 1579-1584 (2010).
Akimoto et al., "Fibroblast growth factor 2 promotes microvessel formation from mouse embryonic aorta" Am. J. Physiol. Cell Physiol., vol. 284, No. 2, 2003, pp. C371-C377.
Anderson et al., "Apert syndrome mutations in fibroblast growth factor receptor 2exhibit increased affinity for FGF ligand" Human Molecular Genetics, vol. 7, No. 9,1998, pp. 1475-1483.
Andre et al., "Molecular Characterization of Breast Cancer with High-ResolutionOligonucleotide Comparative Genomic Hybridization Array," Clin Cancer Res, 2009,15(2): 441-451.
Auguste et al., "Inhibition of fibroblast growth factor-fibroblast growth factor receptor activity in glioma cells impedes tumor growth by both angiogenesis-dependent and -independent mechanisms" Cancer Research, vol. 61, Feb. 15, 2001, pp. 1717-1726.
Baker et al., "Metabolic control of recombinant protein N-glycan processing in NSOand CHO cells" Biotechnology and Bioengineering, vol. 73, No. 3, May 5, 2001, pp. 188-202.
Ballinger et al., "Semirational design of a potent, artificial agonist of fibroblastgrowth factor receptors" Nature Biotechnology, vol. 17, Dec. 1999, pp. 1199-1204.
Bansal et al., "The Molecular Biology of Endometrial Cancers and the Implicationsfor Pathogenesis, Classification, and Targeted Therapies," Cancer Control, 2009,16(1): 8-13.
Bass et al., "SOX2 is an Amplified Lineage Survival Oncogene in Lung and Esophageal Squamous Cell Carcinomas," Nat. Genet., 2009, 41(11): 1238-1242, including supplemental information (15 pages).
Beroukhim et al., "The landscape of somatic copy-number alteration across human cancers," Nature, 2010, 463: 899-905.
Bjornsson et al., Pharmacokinetics of Heparin. II. Studies of Time Dependence in Rats, the Journal of Pharmacology and Experimental Therapeutics, vol. 210, No. 2, Apr. 1979, pp. 243-246.
Byron and Pollock, "FGFR2 as a molecular target in endometrial cancer," FutureOncol, 2009, 5(1):27-32.
Byron et al., "FGFR2 mutations are rare across histologic subtypes of ovariancancer," Gynecologic Oncology, 2010, 117(1): 125-129.
Byron et al., "Inhibition of Activated Fibroblast Growth Factor Receptor 2 inEndometrial Cancer Cells Induces Cell Death Despite PTEN Abrogation," Cancer Res,2008, 68(17):6902-6907.
Celli et al., "Soluble dominant-negative receptor uncovers essential roles forfibroblast growth factors in multi-organ induction and patterning" The EMBO Journal, vol. 17, No. 6, Mar. 16, 1998, pp. 1642-1655.
Chellaiah et al., "Mapping ligand binding domains in chimeric fibroblast growthfactor receptor molecules" J. Biol. Chem., vol. 274, No. 49, Dec. 3, 1999, pp. 34785-34794.
Cheon et al., "High-affinity binding sites for related fibroblast growth factor ligandsreside within different receptor immunoglobulin-like domains" Proc. Natl. Acad. Sci.,vol. 91, Feb. 1994, pp. 989-993.
Choo et al., "SPdb—a Signal Peptide Database," BMC Bioinformatics, vol. 6, No. 249, Oct. 2005, pp. 1-8.
Compagni et al., "Fibroblast growth factors are required for efficient tumorangiogenesis" Cancer Research, vol. 60, Dec. 15, 2000, pp. 7163-7169.
Coughlin et al., "Acidic and basic fibroblast growth factors stimulate tyrosine kinase activity in vivo" J. Biol. Chem., vol. 263, No. 2, Jan. 15, 1988, pp. 988-993.
Courjal et al., "Comparative Genomic Hybridization Analysis of Breast Tumors withPredetermined Profiles of DNA Amplification," Cancer Res. 1997, 57(19): 4368-77.
Cuny et al., "Relating genotype and phenotype in breast cancer: an analysis of the prognostic significance of amplification at eight different genes or loci and of p53 mutations," Cancer Res. 2000; 60(4):1077-83.
Dutt et al., "Drug-sensitive FGFR2 mutations in endometrial carcinoma," PNAS,2008, 105(25): 8713-8717.
Dutt et al., "Inhibitor-Sensitive FGFR1 Amplification in Human Non-Small Cell LungCancer," 2011, PLoS One, 6(6): e20351, 10 pages.
Elbauomy Elsheikh et al., "FGFR1 amplification in breast carcinomas: achromogenic in situ hybridisation analysis," Breast Cancer Research, 2007, 9:R23, 12 pages.
European Search Report, dated Jun. 5, 2009, in European Application No. 09075061.3, 2 pages.
European Search Report, dated May 2, 2013, in European Patent Application No. 10817774.2, 8 pages.
Ezzat et al., "A soluble dominant negative fibroblast growth factor receptor 4 isoform in human MCF-7 breast cancer cells" Biochem. Biophys. Res. Comm., vol. 287, No. 1, 2001, pp. 60-65.
Feige et al., "Glycosylation of the basic fibroblast growth factor receptor" J. Biol.Chem., vol. 263, No. 28, Oct. 5, 1988, pp. 14023-14029.
File History for U.S. Appl. No. 14/185,086, filed Feb. 20, 2014.
File History for U.S. Appl. No. 11/791,889, filed May 30, 2007.

(56) References Cited

OTHER PUBLICATIONS

File History for U.S. Appl. No. 12/535,479, filed Aug. 4, 2009.
File History for U.S. Appl. No. 12/652,720, filed Jan. 5, 2010.
File History for U.S. Appl. No. 13/157,712, filed Jun. 10, 2011.
File history for U.S. Appl. No. 13/227,398, filed Sep. 7, 2011.
File History for U.S. Appl. No. 13/296,161, filed Nov. 14, 2011.
File History for U.S. Appl. No. 13/296,168, filed Nov. 14, 2011.
File History for U.S. Appl. No. 13/438,638, filed Apr. 3, 2012.
File History for U.S. Appl. No. 13/496,182, filed Mar. 14, 2012.
File History for U.S. Appl. No. 13/509,068, filed Jun. 13, 2012.
File History for U.S. Appl. No. 13/515,429, filed Nov. 21, 2012.
File History for U.S. Appl. No. 13/612,044, filed Sep. 12, 2012.
File History for U.S. Appl. No. 13/675,255, filed Nov. 13, 2012.
File History for U.S. Appl. No. 13/905,042, filed May 29, 2013.
File History for U.S. Appl. No. 13/913,292, filed Jun. 7, 2013.
File History for U.S. Appl. No. 14/048,841, filed Oct. 8, 2013.
File History for U.S. Appl. No. 14/079,742, filed Nov. 14, 2013.
File History for U.S. Appl. No. 14/357,336, filed May 9, 2014.
Freireich et al., "Equivalent Surface Area Dosage Conversion Factors Representative Surface Area to Weight Ratios [km] for Varios Species," retrived from https://ncifrederick.cancer.gov/Lasp/Acuc/Frederick/Media/Documents/ACUC42.pdf, retrived Oct. 24, 2014, 1 page.
Garcia-Caballero et al., Determination of HER2 amplification in primary breast cancer using dual-color chromogenic in situ hybridization is comparable to fluorescence in situ hybridization: a European multicentre study involving 168 specimens, Histopathology, 472-480, 2010.
Trueb et al., "Characterization of FGFRL 1, a novel fibroblast growth factor (FGF)receptor preferentially expressed in skeletal tissues" J. Biol. Chem., vol. 278, No. 36,Sep. 5, 2003, pp. 33857-33865.
Tucker et al., "A novel approach for inhibiting growth factor signalling in murine tooth development" Eur. J. Oral Sci., vol. 106 (suppl. 1), 1998, pp. 122-125.
Tuominen et al., "Expression and glycosylation studies of human FGF Receptor 4" Protein Expression and Purification, vol. 21, Mar. 2001, pp. 275-285.
Turner et al., "A Therapeutic Target for Smoking-Associated Lung Cancer," 2010, Science Trans. Med. 2(62):62ps56, 4 pages.
Turner et al., "FGFR1 Amplification Drives Endocrine Therapy Resistance and is a Therapeutic Target in Breast Cancer," 2010, 70(5): 2085-2094.
Ueno et al., "A truncated form of fibroblast growth factor receptor 1 inhibits signaltransduction by multiple types of Fibroblast growth factor receptor" J. Biol. Chem., vol. 267, No. 3, Jan. 25, 1992, pp. 1470-1476.
Van Den Nieuwenhof et al., "Recombinant glycodelin carrying the same type ofglycan structures as contraceptive glycodelin-A can be produced in human kidney 293 cells but not in Chinese hamster ovary cells" Eur. J. Biochem., vol. 267, Aug. 2000, pp. 4753-4762.
Voortman et al., "Array comparative genomic hybridization-based characterization of genetic alterations in pulmonary neuroendocrine tumors," 2010, PNAS, 107(29): 13040-13045.
Wagner et al., "Suppression of fibroblast growth factor receptor signaling inhibitspancreatic cancer growth in vitro and in vivo" Gastroenterology, vol. 114, Apr. 1998, pp. 798-807.
Wang et al., "Alternately Spliced NH2-terminalImmunoglobulin-like Loop I in the Ectodomain of the Fibroblast Growth Factor (FGF) Receptor 1 Lowers Affinity for both Heparin and FGF-1," J. Biol. Chem, 270(17): 10231-10235 (1995).
Wang et al., "A natural kinase-deficient variant of fibroblast growth factor receptor 1" Biochemistry, Vo. 35, 1996, pp. 10134-10142.
Wang et al., "Purification and characterization of a functional soluble fibroblast growth factor receptor 1" Biochem. Biophys. Res. Comm., vol. 203, No. 3, Sep. 30, 1994, pp. 1781-1788.
Weiss et al., "Frequent and Focal FGFR1 Amplification Associates withTherapeutically Tractable FGFR1 Dependency in Squamous Cell Lung Cancer,"Science Trans. Med., 2010, 2(62): 62ra93, 8 pages.

Wells, "Additivity of Mutational Effects in Proteins," Biochemistry, 1990, 29(37):8509-8517.
Werner et al., "Differential splicing in the extracellular region of fibroblast growthfactor receptor 1 generates receptor variants with different ligand-binding specificities" Molecular and Cellular Biology, vol. 12, No. 1, Jan. 1992, pp. 82-88.
Williams et al., "Activation of the FGF receptor underlies neurite outgrowthstimulated by L 1, N-CAM, and N-Cadherin" Neuron, vol. 13, Sep. 1994, pp. 583-594.
Xuan et al., Quantitative assessment of HER2 amplification in HER2-positive breast cancer: its association with clinical outcomes. Breast Ca. Res. Treat. 150, 581-588, 2015.
Ye et al., "FGF and Shh signals control dopaminergic and serotonergic cell fate in theanterior neural plate" Cell, vol. 93, May 29, 1998, pp. 755-766.
Yoo et al., "Docetaxel Associated Pathways in Cisplatin Resistant Head and Neck Squamous Cell Carcinoma: A Pilot Study," Laryngoscope, 115: 1938-1946 (2005).
Yu et al., "Loss of fibroblast growth factor receptor 2 ligand-binding specificity in Apert syndrome," PNAS, 2000, 97(26):14536-14541.
Zhang et al., "FP-1039 (FGFR1:Fc), A Soluble FGFR1 Receptor Antagonist, Inhibits Tumor Growth and Angiogenesis," AACR-NCI-EORTC International Conference, Oct. 22-26, 2007, San Francisco, CA.
Zhang et al., "FP-1039 (FGFR1:Fc), A Soluble FGFR1 Receptor Antagonist, Inhibits Tumor Growth and Angiogenesis," Abstract B55, AACR Meeting Abstracts, AACR-NCI-EORTC International Conference Molecular Targets and Cancer Therapeutics (Oct. 22-26, 2007), 2 pages.
Zhang et al., Receptor Specificity of the Fibroblast Growth Factor Family: The Complete Mammalian FGF Family, The Journal of Biological Chemistry, vol. 281, No. 23, Jun. 9, 2006, pp. 15694-15700.
Zheng et al. "Enhanced efficacy in anti-tumour activity by combined therapy ofrecombinant FGFR-1 related angiogenesis and low-dose cytotoxic agent," EuropeanJournal of Cancer, vol. 43, No. 14, Sep. 14, 2007, pp. 2134-2139.
Zytovision GmbH, Catalogue 2011, 1st Edition, 84 pages.
Liu et al, "Utilization of Unlabeled Probes for the Detection of Fibroblast Growth Factor Receptor 2 Exons 7 and 12 Mutations in Endometrial Carcinoma," Appl Immunohistochem Mol Morphol, 2011, 19(4):341-346.
Liuzzo et al., "Human leukemia cell lines bind basic fibroblast growth factor (FGF) on FGF receptors and heparin sulfates: downmodulation of FGF receptors by phorbol ester" Blood, vol. 87, No. 1, Jan. 1, 1996, pp. 245-255.
Long et al. "Abstract #2789: Antitumor efficacy of FP-1039, a soluble FGF receptor 1:Fc conjugate, as a single agent or in combination with anticancer drugs," Proceedings of the American Association for Cancer Research, Apr. 18-22, 2009 Denver, CO.
Long et al. "Preclinical antitumor efficacy of FP-1039, a soluble FGF receptor 1:Fc conjugate, as a single agent or in combination with anticancer drugs," Proceedings of the American association for Cancer Research, Apr. 17-22, 2009 Denver, CO.
Loo et al., "Production and characterization of the extracellular domain of recombinant human fibroblast growth factor receptor 4," Intl. J. Biochem. Cell Biol., 32: 489-497 (2000).
Lopez et al., "A novel type I fibroblast growth factor receptor activates mitogenicsignaling in the absence of detectable tyrosine phosphorylation of FRS2" J. Biol.Chem., vol. 275, No. 21, May 26, 2000, pp. 15933-15939.
Lundin et al., "Selectively desulfated heparin inhibits fibroblast growth factor-induced mitogenicity and angiogenesis" J. Biol. Chem., vol. 275, No. 32, Aug. 11, 2000, pp. 24653-24660.
Ma et al., "Combination of antiangiogenesis with chemotherapy for more effective cancer treatment," Mol Cancer Ther, 7: 3670-3684 (2008).
Mansukhani et al., "A murine fibroblast growth factor (FGF) receptor expressed inCHO cells is activated by basic FGF and Kaposi FGF" Proc. Natl. Acad. Sci., vol. 87,Jun. 1990, pp. 4378-4382.
Marics et al., FGFR4 signaling is a necessary step in limb muscle differentiation,?Development, 2002, 129:4559-4569.

(56) References Cited

OTHER PUBLICATIONS

Marshall et al., "Fibroblast Growth Factor Receptors Are Components of Autocrine Signaling Networks in Head and Neck Squamous Cell Carcinoma Cells," 2011, 17(15): 5016-5025.
Mayer et al., "Ratiometric dosing of anticancer drug combinations: Controlling drug ratios after systemic administration regulates therapeutic activity in tumor-bearing mice," Mol Cancer Ther, 5(7): 1854-1863 (2006).
Meijer et al., "Fibroblast Growth Factor Receptor 4 Predicts Failure on TamoxifenTherapy in Patients with Recurrent Breast Cancer," Endocrine-Related Cancer, vol. 15,2008, pp. 101-111.
Moloney et al., "Exclusive paternal origin of new mutations in Apert syndrome," Nature Genetics, 1996, 13:48-53.
Murphy et al. "Low-level TOP2A amplification in prostate cancer is associated with HER2 duplication, androgen resistance, and decreased survival", Cancer Res., 67, 2893-2898, 2003.
Ogawa et al., "Anti-tumor angiogenesis therapy using soluble receptors: enhancedinhibition of tumor growth when soluble fibroblast growth factor receptor-1 is used with soluble vascular endothelial growth factor receptor" Cancer Gene Therapy, vol. 9, Aug. 2002, pp. 633-640.
Olsen et al., "Insights into the molecular basis for fibroblast growth factor receptorautoinhibition and ligand-binding promiscuity" Proc. Natl. Acad. Sci., vol. 101, No. 4 Jan. 27, 2004, pp. 935-940.
Ornitz et al., "Heparin is required for cell-free binding of basic fibroblast growthfactor to a soluble receptor and for mitogenesis in whole cells" Molecular and Cellular Biology, vol. 12, Jan. 1992, pp. 240-247.
Ornitz et al., "Receptor specificity of the fibroblast growth factor family" J. Biol.Chem., vol. 271, No. 25, Jun. 21, 1996, pp. 15292-15297.
Otto et al., "Sialylated complex-type N-glycans enhance the signaling activity ofsoluble intercellular adhesion molecule-1 in mouse astrocytes" J. Biol. Chem., vol. 279, No. 34, Aug. 20, 2004, pp. 35201-35209.
Pasquale et al., "Identification of a developmentally regulated protein-tyrosinekinase by using anti-phosphotyrosine antibodies to screen a cDNA expression library" Proc. Natl. Acad. Sci., vol. 86, Jul. 1989, pp. 5449-5453.
Pellegrini et al., "Crystal structure of fibroblast growth factor receptor ectodomain bound to ligand and heparin," Nature, 407: 1029-1034 (2000).
Plotnikov et al., "Crystal structures of two FGF-FGFR complexes reveal thedeterminants of ligand-receptor specificity" Cell, vol. 101, May 12, 2000, pp. 413-424.
Plotnikov et al., "Structural basis for FGF receptor dimerization and activation" Cell, vol. 98, Sep. 3, 1999, pp. 641-650.
Pollock et al., "Frequent activating FGFR2 mutations in endometrial carcinomasparallel germline mutations associated with craniosynostosis and skeletal dysplasiasyndromes," Oncogene, 2007, 26:7158-7162.
Powell et al., "Fibroblast growth factor receptors 1 and 2 interact differently withheparin-heparan sulfate" J. Biol. Chem., vol. 277, No. 32, Aug. 9, 2002, pp. 28554-28563.
Powers et al., "Fibroblast growth factors, their receptors and signaling", XP-002165147, Endocrine-Related Cancer, 7, pp. 165-197, (2000).
Rang et al, "Cancer chemotherapy," Rang and Dale's Pharmacology, Churchill Linvingston Elsevier, 2008, pp. 718-735.
Rets-Filho et al., "FGFR1Emerges as a PotentialTherapeuticTarget for Lobular Breast Carcinomas," 2006, Clin. Cancer Res. 12(22): 6652-6662.
Reynolds et al., "Evaluating Response to Antineoplastic Drug Combinations in Tissue Culture Models," from Methods in Molecular Medicine, vol. 110: Chemosensitivity: vol. 1: In Vitro Assays, Edited by R.D. Blumenthal, Humana Press Inc., Totowa, NJ, pp. 173-183, 2005.
Robertson et al., "Activating mutations in the extracellular domain of the fibroblast growth factor receptor 2 function by disruption of the disulfide bond in the third immunoglobulin-like domain," Proc. Natl. Acad. Sci., USA, 95: 4567-4572 (1998).
Roghani et al., "Heparin increases the affinity of basic fibroblast growth factor for its receptor but is not required for binding" J. Biol. Chem., vol. 269, No. 6, Feb. 11, 1994, pp. 3976-3984.
Ruta et al., "A novel protein tyrosine kinase gene whose expression is modulatedduring endothelial cell differentiation" Oncogene, 1988, vol. 3, pp. 9-15.
Sahadevan et al., "Selective Over-expression of Fibroblast Growth FactorReceptors 1 and 4 in Clinical Prostate Cancer," Journal of Pathology, vol. 213, Jul. 2007, pp. 82-90.
Sanchez-Heras et al., "The fibroblast growth factor receptor acid box is essentialfor interactions with N-cadherin and all of the major isoforms of neural cell adhesion molecules," J Biol Chem, 2006, 281(46):35208-16.
Saramaki et al. "The gene for polycomb group protein enhancer of Zeste Homolog 2 (EZH2) is amplified in late-stage prostate cancer", Genes, Chromos. & Cancer, 45, 639-645, 2006.
Schlessinger et al., "Crystal Structure of the Ternary FGF-FGFR-Herparin Complex Reveals a Dual Role for Heparin in FGFR Binding and Dimerization," Molecular Cell, 6: 743-750 (2000).
Seshacharyulu et al., "Targeting the EGFR signaling pathway in cancer therapy," Expert Opin Ther Targets, 16(1 ): 15-31 (2012).
Shamim et al., "Sequential roles for Fgf4, En1 and Fgf8 in specification andregionalization of the mid brain" Development, vol. 126, Feb. 1999, pp. 945-959.
Smith et al., "The asparagine-linked oligosaccharides on tissue factor pathway inhibitor terminate with SO4-4GalNAc?1,4GlcNAc?1,2Man?" J. Biol. Chem., vol. 267, No. 27, Sep. 25, 1992, pp. 19140-19146.
St. Bernard et al., "Fibroblast growth factor receptors as molecular targets inthyroid carcinoma" Endocrinology, vol. 146, No. 3, 2005, pp. 1145-1153.
St. Bernard et al., "Fibroblast growth factor receptors as molecular targets in thyroid carcinoma" Endocrinology, vol. 10, Nov. 24, 2004, pp. 1-26 and 6 pgs. figures.
Stauber et al., "Structural interaction of fibroblast growth factor receptor with its ligands," Proc. Natl. Acad. Sci., USA, 97(1): 49-54 (2000).
Sugiura et al., "Co-expression of aFGF and FGFR-1 is predictive of a poorprognosis in patients with esophageal squamous cell carcinoma," Oncology Reports,2007, 17: 557-564.
Tacer et al., "Research Resource: Comprehensive Expression Atlas of the Fibroblast Growth Factor System in Adult Mouse," Mol Endocrinol., 2010, 24(10):2050-2064, incl Supplemental Files, 23 pages total.
Taraboletti et al., "Potential Antagonism of Tubulin-Binding Anticancer Agents inCombination Therapies," Clin Cancer Res 11 (7): 2720-2726 (2005).
Tolcher et al., "Preliminary results of a dose escalation study of the Fibroblast Growth Factor (FGF) "trap" FP-1039 (FGFR1:Fc) in patients with advanced malignancies," European Journal of Cancer, Supplement, 8(7): 121, Abstract No. 381 (Nov. 18, 2010).
Tolcher et al., "Preliminary Results of a Dose Escalation Study of the Fibroblast Growth Factor (FGF) "trap" FP-1039 (FGFR1:Fc) In Patients With Advanced Malignancies," 22nd EORTC-NCI-AACR Symposium on Molecular Targets and Cancer Therapeutics Poster (Nov. 16-19, 2010).
Tolcher et al., "Preliminary Results of a Phase 1 Study of FP-1039 (FGFR1:Fc), A Novel Antagonist of Multiple Fibroblast Growth Factor (FGF) Ligands, In Patients With Advanced Malignancies," 2009 AACR-EORTC-NCI Molecular Targets and Cancer Therapeutics Conference Poster (Nov. 15-18, 2009).
Tomlinson et al., "Alternative splicing of fibroblast growth factor receptor 3 produces a secreted isoform that inhibits fibroblast growth factor-induced proliferation and is repressed in urothelial carcinoma cell lines" Cancer Research, vol. 65, No. 22, Nov. 15, 2005, pp. 10441-10449.

\* cited by examiner

*p = 0.0069, Mann Whitney t-test*

METHODS OF TREATING LUNG CANCER

This application is a divisional of U.S. patent application Ser. No. 14/357,336, filed May 9, 2014, which is a 371 application of PCT/US2012/064772 filed Nov. 13, 2012, which claims the benefit of U.S. Provisional Application No. 61/559,259, filed Nov. 14, 2011; and U.S. Provisional Application No. 61/616,761, filed Mar. 28, 2012, which are incorporated herein by reference in their entireties for any purpose.

BACKGROUND

Soluble forms of Fibroblast Growth Factor Receptor 1 (FGFR1) have been shown to inhibit tumor cell growth in vitro and in vivo. See, e.g., U.S. Pat. No. 7,678,890. The efficacy of anti-cancer therapies is, in some instances, dependent on the genetic makeup of the cancer being targeted.

SUMMARY OF THE INVENTION

The inventors have demonstrated that certain cancers that comprise FGFR1 gene amplification are, in some embodiments, more responsive to therapies involving administration of a fibroblast growth factor receptor 1 (FGFR1) extracellular domain (ECD) or FGFR1 ECD fusion molecule, than cancers that do not comprise an FGFR1 gene amplification. In some embodiments, cancers that have FGFR1 overexpression are more responsive to therapies involving administration of FGFR1 ECD or FGFR1 ECD fusion molecules, than cancers that do not have FGFR1 overexpression. In some embodiments, FGFR1 is FGFR1IIIc. In some embodiments, cancers that have fibroblast growth factor receptor 3 isoform IIIc (FGFR3IIIc) overexpression are more responsive to therapies involving administration of FGFR1 ECD or FGFR1 ECD fusion molecules, than cancers that do not have FGFR3IIIc overexpression. In some embodiments, cancers that have fibroblast growth factor 2 (FGF2) overexpression are more responsive to therapies involving administration of FGFR1 ECD or FGFR1 ECD fusion molecules, than cancers that do not have FGF2 overexpression. In some embodiments, cancers that have dickkopf-related protein 3 (DKK3) overexpression are more responsive to therapies involving administration of FGFR1 ECD or FGFR1 ECD fusion molecules, than cancers that do not have DKK3 overexpression. In some embodiments, cancers that have ETS translocation variant 4 (ETV4) overexpression are more responsive to therapies involving administration of FGFR1 ECD or FGFR1 ECD fusion molecules, than cancers that do not have ETV4 overexpression. In some embodiments, cancers that have FGF18 overexpression are more responsive to therapies involving administration of FGFR1 ECD or FGFR1 ECD fusion molecules, than cancers that do not have FGF18 overexpression.

In some embodiments, methods of treating a cancer having an FGFR1 gene amplification, wherein an FGFR1 gene amplification is indicative of therapeutic responsiveness by the cancer to a fibroblast growth factor receptor 1 (FGFR1) extracellular domain (ECD) or an FGFR1 ECD fusion molecule, comprise administering a therapeutically effective amount of an FGFR1 ECD or an FGFR1 ECD fusion molecule to the subject. In some embodiments, methods of treating cancer in a subject comprise administering a therapeutically effective amount of a fibroblast growth factor receptor 1 (FGFR1) extracellular domain (ECD) or an FGFR1 ECD fusion molecule to the subject, wherein, prior to administration of the FGFR1 ECD or FGFR1 ECD fusion molecule, at least a portion of the cells of the cancer have been determined to have an FGFR1 gene amplification, and wherein an FGFR1 gene amplification in a cancer is indicative of therapeutic responsiveness of the cancer to an FGFR1 ECD or FGFR1 ECD fusion molecule.

In some embodiments, methods of treating a lung cancer having an FGFR1 gene amplification, wherein an FGFR1 gene amplification is indicative of therapeutic responsiveness by the lung cancer to a fibroblast growth factor receptor 1 (FGFR1) extracellular domain (ECD) or an FGFR1 ECD fusion molecule, comprise administering a therapeutically effective amount of an FGFR1 ECD or an FGFR1 ECD fusion molecule to the subject. In some embodiments, methods of treating lung cancer in a subject comprise administering a therapeutically effective amount of a fibroblast growth factor receptor 1 (FGFR1) extracellular domain (ECD) or an FGFR1 ECD fusion molecule to the subject, wherein, prior to administration of the FGFR1 ECD or FGFR1 ECD fusion molecule, at least a portion of the cells of the lung cancer have been determined to have an FGFR1 gene amplification, and wherein an FGFR1 gene amplification in a cancer is indicative of therapeutic responsiveness of the lung cancer to an FGFR1 ECD or FGFR1 ECD fusion molecule. In some embodiments, the lung cancer is small cell lung cancer. In some embodiments, the lung cancer is non-small cell lung cancer.

In some embodiments, at least a portion of the cells of the cancer comprise at least three, at least four, at least five, at least six, at least eight, or at least ten copies of the FGFR1 gene. In some embodiments, at least a portion of the cells of the cancer have a ratio of FGFR1 gene to chromosome 8 centromere of at least 1.5, at least 2, at least 2.5, at least 3, at least 3.5, or at least 4.

In some embodiments, including any of the foregoing embodiments, the cancer may overexpress at least one, at least two, at least three, at least four, or at least five markers selected from FGFR1, FGFR3IIIc, FGF2, DKK3, FGF18, and ETV4. In some embodiments, the cancer may overexpress at least one, at least two, at least three, at least four, or five markers selected from FGFR1, FGFR3IIIc, FGF2, DKK3, and FGF18. In some embodiments, the cancer may overexpress ETV4. In some embodiments, including any of the foregoing embodiments, the cancer may overexpress Gene 1 and Gene 2 from any line in Table 10 below, or any combination thereof. In some embodiments, FGFR1 is FGFR1IIIc. In some embodiments, including any of the foregoing embodiments, the FGFR1 gene may be amplified.

In some embodiments, methods of treating a cancer that overexpress at least one, at least two, at least three, or at least four markers selected from FGFR1, FGFR3IIIc, FGF2, DKK3, FGF18, and ETV4 are provided. In some embodiments, overexpression of at least one, at least two, at least three, or at least four markers selected from FGFR1, FGFR3IIIc, FGF2, DKK3, FGF18, and ETV4 is indicative of therapeutic responsiveness by the cancer to a fibroblast growth factor receptor 1 (FGFR1) extracellular domain (ECD) or an FGFR1 ECD fusion molecule. In some embodiments, a method comprises administering a therapeutically effective amount of an FGFR1 ECD or an FGFR1 ECD fusion molecule to a subject with cancer that overexpress at least one, at least two, at least three, or at least four markers selected from FGFR1, FGFR3IIIc, FGF2, DKK3, FGF18, and ETV4. In some embodiments, methods of treating cancer in a subject comprise administering a therapeutically effective amount of an FGFR1 ECD or an FGFR1 ECD fusion molecule to the subject, wherein, prior to administration of the FGFR1 ECD or FGFR1 ECD fusion molecule, at least a portion of the cells of the cancer have been determined to overexpress at least one, at least two, at least three, or at least four markers selected from FGFR1, FGFR3IIIc, FGF2, DKK3, FGF18, and ETV4, and wherein overexpression of at least one, at least two, at least three, or at least four markers selected from FGFR1, FGFR3IIIc, FGF2, DKK3, FGF18, and ETV4 in a cancer is indicative of therapeutic responsiveness of the cancer to an FGFR1 ECD or FGFR1 ECD fusion molecule. In some embodiments, the cancer also has an FGFR1 gene amplification. In some embodiments, at least a portion of the cells of the cancer having an FGFR1 gene amplification comprise at least three, at least four, at least five, at least six, at least seven, or at least eight copies of the FGFR1 gene. In some embodiments, the overexpression is mRNA overexpression. In some embodiments, mRNA overexpression is determined by quantitative RT-PCR. In some embodiments, the overexpression is protein overexpression. In some embodiments, protein overexpression is determined by immunohistochemistry. In some embodiments, FGFR1 is FGFR1IIIc.

In some embodiments, methods of treating a cancer having FGFR1 overexpression, wherein FGFR1 overexpression is indicative of therapeutic responsiveness by the cancer to a fibroblast growth factor receptor 1 (FGFR1) extracellular domain (ECD) or an FGFR1 ECD fusion molecule, comprise administering a therapeutically effective amount of an FGFR1 ECD or an FGFR1 ECD fusion molecule to the subject. In some embodiments, methods of treating cancer in a subject comprise administering a therapeutically effective amount of an FGFR1 ECD or an FGFR1 ECD fusion molecule to the subject, wherein, prior to administration of the FGFR1 ECD or FGFR1 ECD fusion molecule, at least a portion of the cells of the cancer have been determined to have FGFR1 overexpression, and wherein FGFR1 overexpression in a cancer is indicative of therapeutic responsiveness of the cancer to an FGFR1 ECD or FGFR1 ECD fusion molecule. In some embodiments, the cancer does not have an FGFR1 gene amplification. In some embodiments, the FGFR1 overexpression is mRNA overexpression. In some embodiments, FGFR1 mRNA overexpression is determined by quantitative RT-PCR. In some embodiments, the FGFR1 overexpression is protein overexpression. In some embodiments, FGFR1 protein overexpression is determined by immunohistochemistry. In some embodiments, FGFR1 is FGFR1IIIc.

In some embodiments, methods of treating a cancer having FGFR3IIIc overexpression, wherein FGFR3IIIc overexpression is indicative of therapeutic responsiveness by the cancer to a fibroblast growth factor receptor 1 (FGFR1) extracellular domain (ECD) or an FGFR1 ECD fusion molecule, comprise administering a therapeutically effective amount of an FGFR1 ECD or an FGFR1 ECD fusion molecule to the subject. In some embodiments, methods of treating cancer in a subject comprise administering a therapeutically effective amount of an FGFR1 ECD or an FGFR1 ECD fusion molecule to the subject, wherein, prior to administration of the FGFR1 ECD or FGFR1 ECD fusion molecule, at least a portion of the cells of the cancer have been determined to have FGFR3IIIc overexpression, and wherein FGFR3IIIc overexpression in a cancer is indicative of therapeutic responsiveness of the cancer to an FGFR1 ECD or FGFR1 ECD fusion molecule. In some embodiments, the cancer does not have an FGFR1 gene amplification. In some embodiments, the FGFR3IIIc overexpression is mRNA overexpression. In some embodiments, FGFR3IIIc mRNA overexpression is determined by quantitative RT-PCR. In some embodiments, the FGFR3IIIc overexpression is protein overexpression. In some embodiments, FGFR3IIIc protein overexpression is determined by immunohistochemistry. In some embodiments, the cancer having FGFR3IIIc overexpression is selected from bladder cancer, renal cell carcinoma, head-and-neck squamous carcinoma, and colorectal cancer.

In some embodiments, methods of treating a cancer having FGF2 overexpression, wherein FGF2 overexpression is indicative of therapeutic responsiveness by the cancer to a fibroblast growth factor receptor 1 (FGFR1) extracellular domain (ECD) or an FGFR1 ECD fusion molecule, comprise administering a therapeutically effective amount of an FGFR1 ECD or an FGFR1 ECD fusion molecule to the subject. In some embodiments, methods of treating cancer in a subject comprise administering a therapeutically effective amount of an FGFR1 ECD or an FGFR1 ECD fusion molecule to the subject, wherein, prior to administration of the FGFR1 ECD or FGFR1 ECD fusion molecule, at least a portion of the cells of the cancer have been determined to have FGF2 overexpression, and wherein FGF2 overexpression in a cancer is indicative of therapeutic responsiveness of the cancer to an FGFR1 ECD or FGFR1 ECD fusion molecule. In some embodiments, the cancer does not have an FGFR1 gene amplification. In some embodiments, the FGF2 overexpression is mRNA overexpression. In some embodiments, FGF2 mRNA overexpression is determined by quantitative RT-PCR. In some embodiments, the FGF2 overexpression is protein overexpression. In some embodiments, FGF2 protein overexpression is determined by immunohistochemistry. In some embodiments, the cancer having FGF2 overexpression is selected from glioblastoma, renal cell carcinoma, and hepatocellular carcinoma.

In some embodiments, methods of treating a cancer having DKK3 overexpression, wherein DKK3 overexpression is indicative of therapeutic responsiveness by the cancer to a fibroblast growth factor receptor 1 (FGFR1) extracellular domain (ECD) or an FGFR1 ECD fusion molecule, comprise administering a therapeutically effective amount of an FGFR1 ECD or an FGFR1 ECD fusion molecule to the subject. In some embodiments, methods of treating cancer in a subject comprise administering a therapeutically effective amount of an FGFR1 ECD or an FGFR1 ECD fusion molecule to the subject, wherein, prior to administration of the FGFR1 ECD or FGFR1 ECD fusion molecule, at least a portion of the cells of the cancer have been determined to have DKK3 overexpression, and wherein DKK3 overexpression in a cancer is indicative of therapeutic responsiveness of the cancer to an FGFR1 ECD or FGFR1 ECD fusion molecule. In some embodiments, the DKK3 overexpression is mRNA overexpression. In some embodiments, DKK3 mRNA overexpression is determined by quantitative RT-PCR. In some embodiments, the DKK3 overexpression is protein overexpression. In some embodiments, DKK3 protein overexpression is determined by immunohistochemistry. In some embodiments, the cancer having DKK3 overexpression is selected from pancreatic cancer, prostate cancer, renal cell carcinoma, lung adenocarcinoma, hepatocellular cancer, and colorectal cancer.

In some embodiments, methods of treating a cancer having FGF18 overexpression, wherein FGF18 overexpression is indicative of therapeutic responsiveness by the cancer to a fibroblast growth factor receptor 1 (FGFR1) extracellular domain (ECD) or an FGFR1 ECD fusion molecule, comprise administering a therapeutically effective amount of an FGFR1 ECD or an FGFR1 ECD fusion molecule to the subject. In some embodiments, methods of treating cancer in a subject comprise administering a therapeutically effective amount of an FGFR1 ECD or an FGFR1 ECD fusion molecule to the subject, wherein, prior to administration of the FGFR1 ECD or FGFR1 ECD fusion molecule, at least a portion of the cells of the cancer have been determined to have FGF18 overexpression, and wherein FGF18 overexpression in a cancer is indicative of therapeutic responsiveness of the cancer to an FGFR1 ECD or FGFR1 ECD fusion molecule. In some embodiments, the FGF18 overexpression is mRNA overexpression. In some embodiments, FGF18 mRNA overexpression is determined by quantitative RT-PCR. In some embodiments, the FGF18 overexpression is protein overexpression. In some embodiments, FGF18 protein overexpression is determined by immunohistochemistry.

In some embodiments, methods of treating a cancer having ETV4 overexpression, wherein ETV4 overexpression is indicative of therapeutic responsiveness by the cancer to a fibroblast growth factor receptor 1 (FGFR1) extracellular domain (ECD) or an FGFR1 ECD fusion molecule, comprise administering a therapeutically effective amount of an FGFR1 ECD or an FGFR1 ECD fusion molecule to the subject. In some embodiments, methods of treating cancer in a subject comprise administering a therapeutically effective amount of an FGFR1 ECD or an FGFR1 ECD fusion molecule to the subject, wherein, prior to administration of the FGFR1 ECD or FGFR1 ECD fusion molecule, at least a portion of the cells of the cancer have been determined to have ETV4 overexpression, and wherein ETV4 overexpression in a cancer is indicative of therapeutic responsiveness of the cancer to an FGFR1 ECD or FGFR1 ECD fusion molecule. In some embodiments, the ETV4 overexpression is mRNA overexpression. In some embodiments, ETV4 mRNA overexpression is determined by quantitative RT-PCR. In some embodiments, the ETV4 overexpression is protein overexpression. In some embodiments, ETV4 protein overexpression is determined by immunohistochemistry.

In some embodiments, methods of treating a lung cancer having FGFR1 overexpression, wherein FGFR1 overexpression is indicative of therapeutic responsiveness by the lung cancer to a fibroblast growth factor receptor 1 (FGFR1) extracellular domain (ECD) or an FGFR1 ECD fusion molecule, comprise administering a therapeutically effective amount of an FGFR1 ECD or an FGFR1 ECD fusion molecule to the subject. In some embodiments, methods of treating lung cancer in a subject comprise administering a therapeutically effective amount of an FGFR1 ECD or an FGFR1 ECD fusion molecule to the subject, wherein, prior to administration of the FGFR1 ECD or FGFR1 ECD fusion molecule, at least a portion of the cells of the lung cancer have been determined to have FGFR1 overexpression, and wherein FGFR1 overexpression in a cancer is indicative of therapeutic responsiveness of the lung cancer to an FGFR1 ECD or FGFR1 ECD fusion molecule. In some embodiments, the cancer does not have an FGFR1 gene amplification. In some embodiments, the lung cancer is small cell lung cancer. In some embodiments, the lung cancer is non-small cell lung cancer. In some embodiments, FGFR1 is FGFR1IIIc.

In some embodiments, methods of treating a lung cancer having FGF2 overexpression, wherein FGF2 overexpression is indicative of therapeutic responsiveness by the lung cancer to a fibroblast growth factor receptor 1 (FGFR1) extracellular domain (ECD) or an FGFR1 ECD fusion molecule, comprise administering a therapeutically effective amount of an FGFR1 ECD or an FGFR1 ECD fusion molecule to the subject. In some embodiments, methods of treating lung cancer in a subject comprise administering a therapeutically effective amount of an FGFR1 ECD or an FGFR1 ECD fusion molecule to the subject, wherein, prior to administration of the FGFR1 ECD or FGFR1 ECD fusion molecule, at least a portion of the cells of the lung cancer have been determined to have FGF2 overexpression, and wherein FGF2 overexpression in a cancer is indicative of therapeutic responsiveness of the lung cancer to an FGFR1 ECD or FGFR1 ECD fusion molecule. In some embodiments, the cancer does not have an FGFR1 gene amplification. In some embodiments, the lung cancer is small cell lung cancer. In some embodiments, the lung cancer is non-small cell lung cancer. In some embodiments, the lung cancer does not have an FGFR1 gene amplification.

In some embodiments, a method of treating a cancer having an FGFR1 gene amplification comprises administering an FGFR1 ECD or FGFR1 ECD fusion molecule and at least one additional therapeutic agent. In some embodiments, a method of treating a cancer that overexpresses at least one, at least two, at least three, or at least four markers selected from FGFR1, FGFR3IIIc, FGF2, DKK3, FGF18, and ETV4 comprises administering an FGFR1 ECD or FGFR1 ECD fusion molecule and at least one additional therapeutic agent. In some embodiments, at least one additional therapeutic agent is selected from docetaxel, paclitaxel, vincristine, carboplatin, cisplatin, oxaliplatin, doxorubicin, 5-fluorouracil (5-FU), leucovorin, pemetrexed, etoposide, topotecan, sorafenib, a VEGF antagonist, a VEGF trap, an anti-VEGF antibody, and bevacizumab. In some embodiments, the at least one additional therapeutic agent is docetaxel. In some embodiments, the cancer is non-small cell lung cancer. In some embodiments, the FGFR1 is FGFR1IIIc.

In some embodiments, a method of treating a cancer having an FGFR1 gene amplification comprises administering an FGFR1 ECD or FGFR1 ECD fusion molecule and at least two additional therapeutic agents. In some embodiments, a method of treating a cancer that overexpresses at least one, at least two, at least three, or at least four markers selected from FGFR1, FGFR3IIIc, FGF2, DKK3, FGF18, and ETV4 comprises administering an FGFR1 ECD or FGFR1 ECD fusion molecule and at least two additional therapeutic agents. In some embodiments, at least two additional therapeutic agents are selected from docetaxel, paclitaxel, vincristine, carboplatin, cisplatin, oxaliplatin, doxorubicin, 5-fluorouracil (5-FU), leucovorin, pemetrexed, etoposide, topotecan, sorafenib, a VEGF antagonist, a VEGF trap, an anti-VEGF antibody, and bevacizumab. In some embodiments, the two additional therapeutic agents are paclitaxel and carboplatin. In some embodiments, the two additional therapeutic agents are doxorubicin and paclitaxel. In some embodiments, the two additional therapeutic agents are cisplatin and etoposide. In some embodiments, the two additional therapeutic agents are oxaliplatin and 5-FU. In some embodiments, the two additional therapeutic agents are 5-FU and leucovorin. In some embodiments, the two additional therapeutic agents are 5-FU and bevacizumab. In some embodiments, the two additional therapeutic agents are paclitaxel and bevacizumab. In some embodiments, the cancer is non-small cell lung cancer.

In some embodiments, a method of treating a cancer having an FGFR1 gene amplification comprises administering an FGFR1 ECD or FGFR1 ECD fusion molecule and at least three additional therapeutic agents. In some embodiments, a method of treating a cancer that overexpresses at least one, at least two, at least three, or at least four markers selected from FGFR1, FGFR3IIIc, FGF2, DKK3, FGF18, and ETV4 comprises administering an FGFR1 ECD or FGFR1 ECD fusion molecule and at least three additional therapeutic agents. In some embodiments, at least three additional therapeutic agents are selected from docetaxel, paclitaxel, vincristine, carboplatin, cisplatin, oxaliplatin, doxorubicin, 5-fluorouracil (5-FU), leucovorin, pemetrexed, etoposide, topotecan, sorafenib, a VEGF antagonist, a VEGF trap, an anti-VEGF antibody, and bevacizumab. In some embodiments, the three additional therapeutic agents are oxaliplatin, 5-FU and leucovorin. In some embodiments, the three additional therapeutic agents are bevacizumab, 5-FU and leucovorin.

In some embodiments, methods of treating a cancer having an FGFR1 gene amplification and/or that overexpresses at least one, at least two, at least three, or at least four markers selected from FGFR1, FGFR3IIIc, FGF2, DKK3, FGF18, and ETV4 comprise administering an FGFR1 ECD. In some such embodiments, the FGFR1 ECD comprises an amino acid sequence selected from SEQ ID NOs: 1 to 4. In some embodiments, methods of treating a cancer having an FGFR1 gene amplification and/or FGFR1 overexpression and/or FGF2 overexpression and/or DKK3 overexpression and/or FGF18 overexpression and/or ETV4 overexpression comprise administering an FGFR1 ECD fusion molecule, wherein the FGFR1 ECD fusion molecule comprises an FGFR1 ECD and at least one fusion partner. In some embodiments, at least one fusion partner is selected from an Fc, albumin, and polyethylene glycol. In some embodiments, at least one fusion partner is an Fc. In some embodiments, the Fc comprises an amino acid sequence selected from SEQ ID NOs: 8 to 10. In some embodiments, the FGFR1 ECD fusion molecule comprises a sequence selected from SEQ ID NO: 5 and SEQ ID NO: 6. In some embodiments, the at least one fusion partner is an Fc and polyethylene glycol. In some embodiments, the at least one fusion partners is polyethylene glycol. In some embodiments, the fusion molecule comprises a linker between the FGFR1 ECD and one or more fusion partners. In some embodiments, the FGFR1 ECD fusion molecule is FGFR1 ECD.339-Fc.

In some embodiments, an FGFR1 ECD or FGFR1 ECD fusion molecule is glycosylated and/or sialylated. In some embodiments, an FGFR1 ECD or the polypeptide portion of the FGFR1 ECD fusion molecule is expressed in Chinese hamster ovary (CHO) cells. In some embodiments, an FGFR1 ECD comprises an amino acid sequence selected from SEQ ID NO: 1 and SEQ ID NO: 3.

In some embodiments, the FGFR1 ECD or FGFR1 ECD fusion molecule is an amount in the range of about 0.5 mg/kg body weight to about 30 mg/kg body weight, such as an amount in the range of about 8 to about 16 mg/kg body weight. In some embodiments, the therapeutically effective amount of the FGFR1 ECD or FGFR1 ECD fusion molecule is a dose of about 8 mg/kg body weight. In some embodiments, the therapeutically effective amount of the FGFR1 ECD or FGFR1 ECD fusion molecule is a dose of about 16 mg/kg body weight. In some embodiments, the therapeutically effective amount of the FGFR1 ECD or FGFR1 ECD fusion molecule is a dose of about 20 mg/kg body weight. In some embodiments, dosages may be administered twice a week, weekly, every other week, at a frequency between weekly and every other week, every three weeks, every four weeks, or every month.

In certain embodiments, the cancer is prostate cancer, breast cancer, colorectal cancer, lung cancer, brain cancer, ovarian cancer, endometrial cancer, esophageal cancer, head and neck cancer, laryngeal cancer, liver cancer, renal cancer, glioblastoma, or pancreatic cancer. In certain embodiments, the cancer is breast cancer, esophageal cancer, renal cancer, head and neck cancer, or lung cancer. In certain embodiments, the cancer is lung cancer. In some embodiments, the lung cancer is non-small cell lung cancer. In some embodiments, the lung cancer is small cell lung cancer. In some embodiments, the lung cancer is squamous cell carcinoma. In some embodiments, the cancer is head and neck cancer. In some embodiments, the head and neck cancer is squamous cell carcinoma of the head and neck.

In some embodiments, methods of identifying a subject with cancer who may benefit from administration of an FGFR1 ECD or FGFR1 ECD fusion molecule are provided. In some embodiments, a method comprises determining whether at least a portion of the cancer cells in a sample obtained from the subject comprise an FGFR1 gene amplification, wherein FGFR1 gene amplification is indicative of therapeutic responsiveness by the cancer to an FGFR1 ECD or FGFR1 ECD fusion molecule. In some embodiments, FGFR1 gene amplification is determined by a method selected from fluorescence in situ hybridization, array comparative genomic hybridization, DNA microarray, spectral karyotyping, quantitative PCR, southern blotting, or sequencing.

In some embodiments, methods of identifying a subject with cancer who may benefit from administration of an FGFR1 ECD or FGFR1 ECD fusion molecule are provided. In some embodiments, a method comprises determining whether at least a portion of the cancer cells in a sample obtained from the subject overexpress at least one, at least two, at least three, at least four, or at least five markers selected from FGFR1, FGFR3IIIc, FGF2, DKK3, FGF18, and ETV4, wherein overexpression is indicative of therapeutic responsiveness by the cancer to an FGFR1 ECD or FGFR1 ECD fusion molecule. In some embodiments, the method comprises determining whether at least a portion of the cancer cells in a sample obtained from the subject overexpress at least one, at least two, at least three, or at least four markers selected from FGFR1, FGFR3IIIc, FGF2, DKK3, and FGF18. In some embodiments, the method comprises determining whether at least a portion of the cancer cells in a sample obtained from the subject overexpress ETV4. In some embodiments, including any of the foregoing embodiments, the method comprises determining whether at least a portion of the cancer cells in a sample obtained from the subject overexpress Gene 1 and Gene 2 from any line in Table 10 below, or any combination thereof. In some embodiments, FGFR1 is FGFR1IIIc. In some embodiments, the overexpression is mRNA overexpression. In some embodiments, mRNA overexpression is determined by quantitative RT-PCR. In some embodiments, the overexpression is protein overexpression. In some embodiments, protein overexpression is determined by immunohistochemistry. In some embodiments, including any of the foregoing embodiments, the method comprises determining whether at least a portion of the cancer cells in a sample obtained from the subject have an FGFR1 gene amplification.

In some embodiments, methods of identifying a subject with cancer who may benefit from administration of an FGFR1 ECD or FGFR1 ECD fusion molecule are provided. In some embodiments, a method comprises determining whether at least a portion of the cancer cells in a sample obtained from the subject overexpress FGF2, wherein overexpression is indicative of therapeutic responsiveness by the cancer to an FGFR1 ECD or FGFR1 ECD fusion molecule.

In some embodiments, the overexpression is mRNA overexpression. In some embodiments, mRNA overexpression is determined by quantitative RT-PCR. In some embodiments, the overexpression is protein overexpression. In some embodiments, protein overexpression is determined by immunohistochemistry. In some embodiments, the cancer is determined not to have an FGFR1 gene amplification. In some embodiments, the cancer is lung cancer. In some embodiments, the cancer is non-small cell lung cancer or small cell lung cancer.

Any embodiment described herein or any combination thereof applies to any and all methods of the invention described herein.

DETAILED DESCRIPTION

Figure 1:
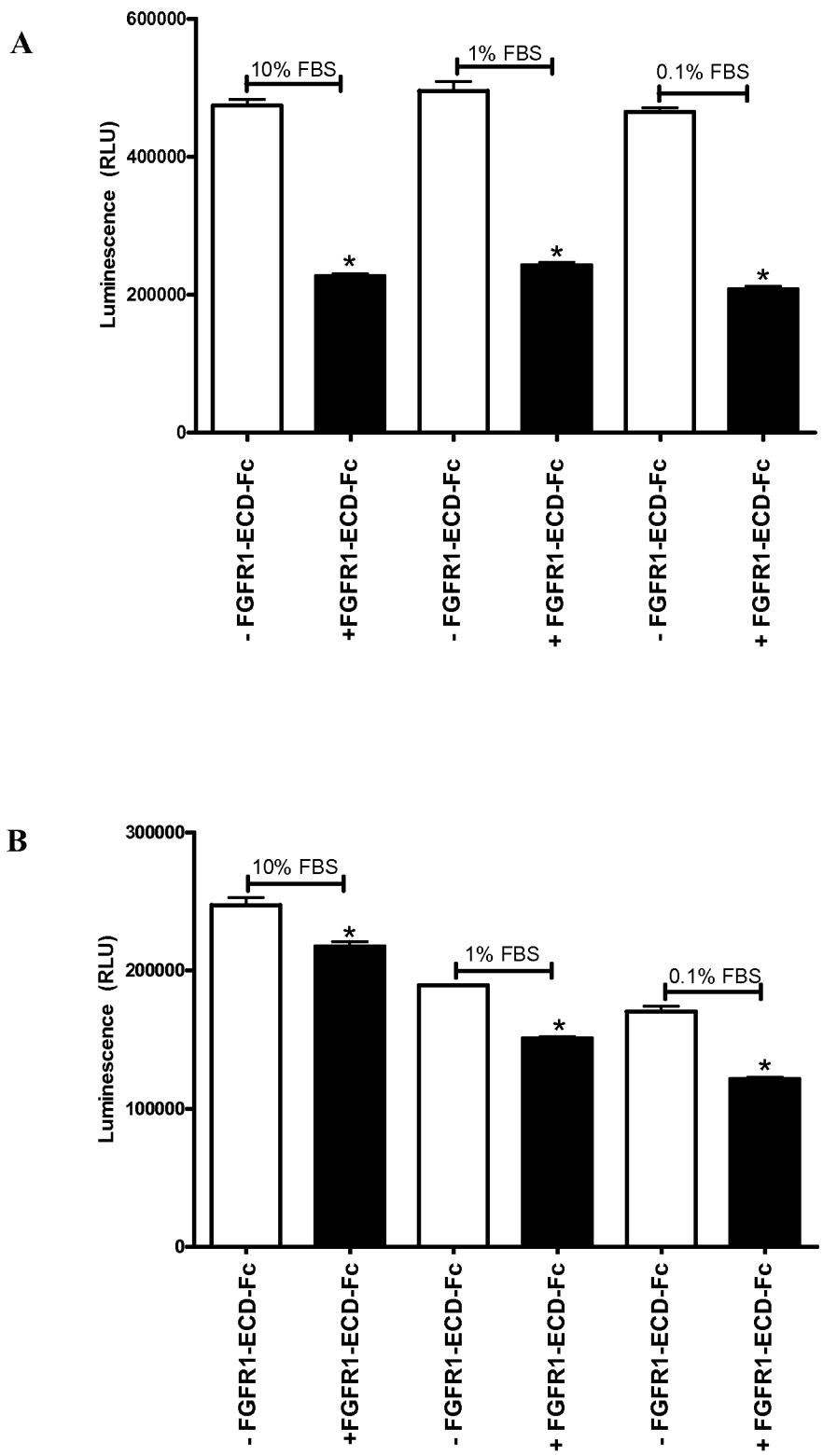
FIG. 1 shows cell number in a culture of (A) NCI-H1581, (B) NCI-H520, (C) DMS53, and (D) DMS114 tumor cells grown in the presence or absence of FGFR1-ECD.339-Fc, with varying amounts of serum, as described in Example 1.
Figure 1:
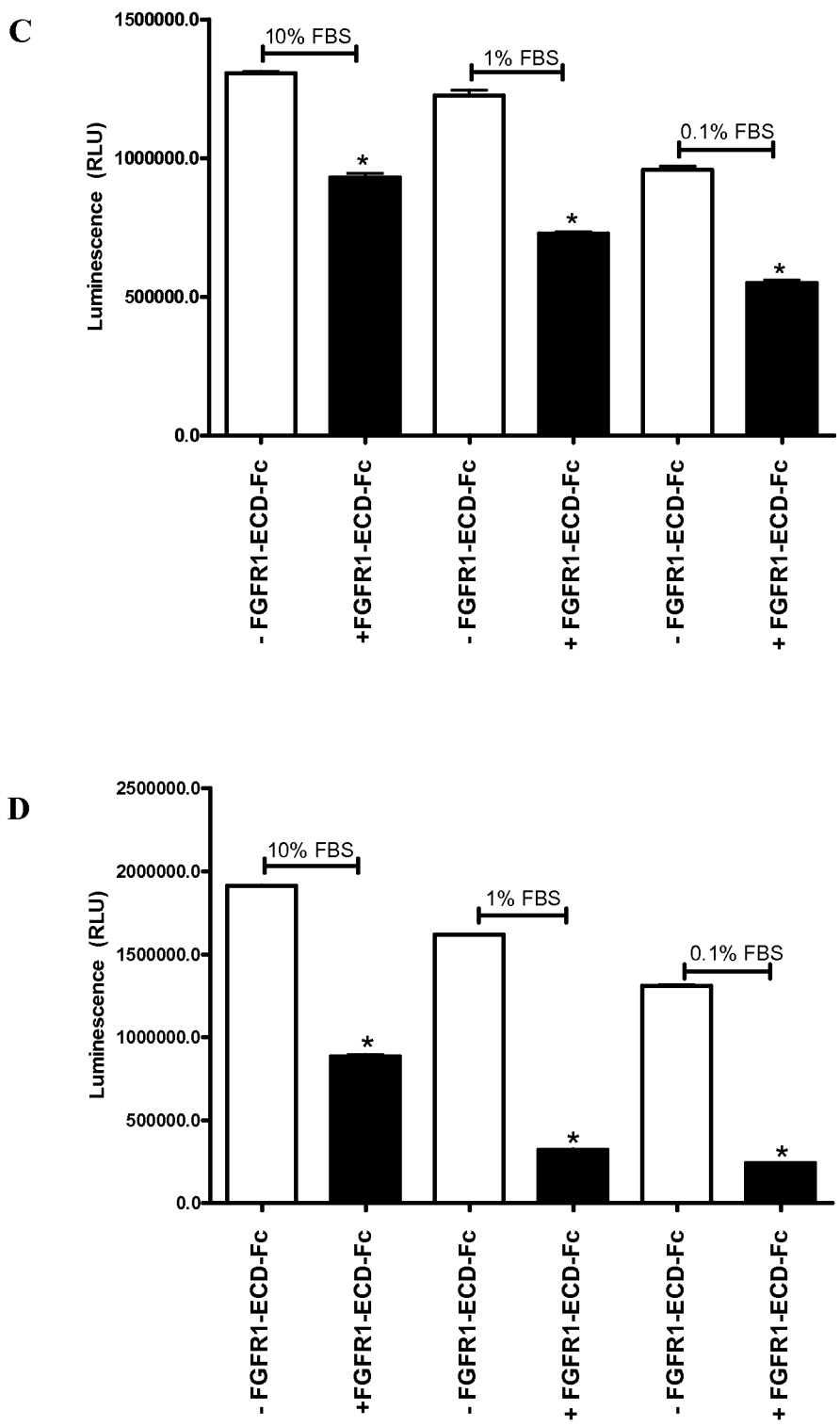

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Certain techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, certain techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As used herein, all numbers are approximate, and may be varied to account for measurement error and the rounding of significant digits. The use of "about" before certain measured quantities includes variations due to sample impurities, measurement error, human error, and statistical variation, as well as the rounding of significant digits.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification. When a polypeptide "consists of" a particular amino acid sequence, it may still contain post-translational modifications, such as glycosylation and sialylation.

The term "FGFR1 extracellular domain" ("FGFR1 ECD") includes full-length FGFR1 ECDs, FGFR1 ECD fragments, and FGFR1 ECD variants. As used herein, the term "FGFR1 ECD" refers to an FGFR1 polypeptide that lacks the intracellular and transmembrane domains, with or without a signal peptide. In some embodiment, the FGFR1 ECD is a human full-length FGFR1 ECD having an amino acid sequence selected from SEQ ID NOs: 1 and 2. The term "full-length FGFR1 ECD", as used herein, refers to an FGFR1 ECD that extends to the last amino acid of the extracellular domain, and may or may not include an N-terminal signal peptide. As defined herein, the last amino acid of the full-length FGFR1 ECD is at position 353. Thus, a human full-length FGFR1 ECD may consist of the amino acid sequence corresponding to SEQ ID NO.: 2 (mature form) or to SEQ ID NO.: 1 (with the signal peptide). As used herein, the term "FGFR1 ECD fragment" refers to an FGFR1 ECD having one or more residues deleted from the N and/or C terminus of the full-length ECD and that retains the ability to bind to FGF-2. The FGFR1 ECD fragment may or may not include an N-terminal signal peptide. In some embodiments, the FGFR1 ECD fragment is a human FGFR1 ECD fragment having an amino acid sequence corresponding to SEQ ID NO.: 4 (mature form) or to SEQ ID NO.: 3 (with the signal peptide).

As used herein, the term "FGFR1 ECD variants" refers to FGFR1 ECDs that contain amino acid additions, deletions, and substitutions and that remain capable of binding to FGF-2. Such variants may be at least 90%, 92%, 95%, 97%, 98%, or 99% identical to the parent FGFR1 ECD. The % identity of two polypeptides can be measured by a similarity score determined by comparing the amino acid sequences of the two polypeptides using the Bestfit program with the default settings for determining similarity. Bestfit uses the local homology algorithm of Smith and Waterman, *Advances in Applied Mathematics* 2:482-489 (1981) to find the best segment of similarity between two sequences. In some embodiments, an FGFR1 ECD variant is at least 95% identical to the sequence of SEQ ID NO: 4.

A polypeptide having an amino acid sequence at least, for example, 95% identical to a reference amino acid sequence of an FGFR1 ECD polypeptide is one in which the amino acid sequence of the polypeptide is identical to the reference sequence except that the polypeptide sequence may include up to five amino acid alterations per each 100 amino acids of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids, up to 5% of the total amino acid residues in the reference sequence, may be inserted into the reference sequence. These alterations of the reference sequence may occur at the N- or C-terminal positions of the reference amino acid sequence or anywhere between those terminal positions, interspersed either individually among residues in the reference sequence, or in one or more contiguous groups within the reference sequence.

As a practical matter, whether any particular polypeptide is at least 70%, 80%, 90%, or 95% identical to, for instance, an amino acid sequence or to a polypeptide sequence encoded by a nucleic acid sequence set forth in the Sequence Listing can be determined conventionally using known computer programs, such the Bestfit program. When using Bestfit or other sequence alignment program to determine whether a particular sequence is, for instance, 95% identical to a reference sequence according to the present invention, the parameters are set, of course, that the percentage of identity is calculated over the full length of the reference amino acid sequence and that gaps in homology of up to 5% of the total number of amino acid residues in the reference sequence are allowed.

As used herein, the terms "hFGFR1-ECD.353" and "hFGFR1.353" may be used interchangeably to refer to the full-length human FGFR1 ECD corresponding to SEQ ID NO: 1 (with signal peptide) or to SEQ ID NO: 2 (without signal peptide; mature form).

As used herein, the terms "hFGFR1-ECD.339" and "hFGFR1.339" may be used interchangeably to refer to the human FGFR1 ECD corresponding to SEQ ID NO: 3 (with signal peptide) or to SEQ ID NO: 4 (without signal peptide; mature form).

Additional hFGFR1 ECDs are described, for example, in U.S. Pat. No. 7,678,890, which is incorporated by reference herein in its entirety for any purpose.

The term "FGFR1 ECD fusion molecule" refers to a molecule comprising an FGFR1 ECD, and one or more "fusion partners." In some embodiments, the FGFR1 ECD and the fusion partner are covalently linked ("fused"). If the fusion partner is also a polypeptide ("the fusion partner polypeptide"), the FGFR1 ECD and the fusion partner polypeptide may be part of a continuous amino acid sequence, and the fusion partner polypeptide may be linked to either the N terminus or the C terminus of the FGFR1 ECD. In such cases, the FGFR1 ECD and the fusion partner polypeptide may be translated as a single polypeptide from a coding sequence that encodes both the FGFR1 ECD and the fusion partner polypeptide (the "FGFR1 ECD fusion protein"). In some embodiments, the FGFR1 ECD and the fusion partner are covalently linked through other means, such as, for example, a chemical linkage other than a peptide bond. Many known methods of covalently linking polypeptides to other molecules (for example, fusion partners) may be used. In other embodiments, the FGFR1 ECD and the fusion partner may be fused through a "linker," which is comprised of at least one amino acid or chemical moiety.

In some embodiments, the FGFR1 ECD polypeptide and the fusion partner are noncovalently linked. In some such embodiments, they may be linked, for example, using binding pairs. Exemplary binding pairs include, but are not limited to, biotin and avidin or streptavidin, an antibody and its antigen, etc.

Exemplary fusion partners include, but are not limited to, an immunoglobulin Fc domain, albumin, and polyethylene glycol. The amino acid sequences of some exemplary Fc domains are shown in SEQ ID NOs: 8 to 10. In some embodiments, an FGFR1 ECD fused to an Fc is referred to as an "hFGFR1 ECD-Fc." In some embodiments, the Fc domain is selected from an IgG1 Fc, an IgG2 Fc, an IgG3 Fc, and an IgG4 Fc.

As used herein, the terms "hFGFR1-ECD.339-Fc" and "hFGFR1.339-Fc" may be used interchangeably to refer to an amino acid sequence selected from SEQ ID NO: 6 (without signal peptide, mature form) and SEQ ID NO: 5 (with signal peptide). Nonlimiting exemplary cancers that may be treated with hFGFR1-ECD.339-Fc include, but are not limited to, lung cancer, colon cancer, breast cancer, gastric cancer, head and neck cancer, prostate cancer, endometrial cancer, sarcoma, small cell lung cancer, ovarian cancer, Kaposi's sarcoma, Hodgkin's disease, leukemia, non-Hodgkin's lymphoma, neuroblastoma (brain cancer), rhabdomyosarcoma, Wilms' tumor, acute lymphoblastic leukemia, acute lymphoblastic leukemia, bladder cancer, testicular cancer, lymphomas, germ cell tumors, cancers of the colon and rectum, gastrointestinal cancers, thyroid cancer, multiple myeloma, pancreatic cancer, mesothelioma, malignant pleural mesothelioma, hematological/lymphatic cancers, malignant peritoneal mesothelioma, esophageal cancer, renal cell carcinoma, glioblastoma multiforme, and liver cancer.

The term "signal peptide" refers to a sequence of amino acid residues located at the N terminus of a polypeptide that facilitates secretion of a polypeptide from a mammalian cell. A signal peptide may be cleaved upon export of the polypeptide from the mammalian cell, forming a mature protein. Signal peptides may be natural or synthetic, and they may be heterologous or homologous to the protein to which they are attached. Exemplary signal peptides include, but are not limited to, FGFR1 signal peptides, such as, for example, the amino acid sequence of SEQ ID NO: 7. Exemplary signal peptides also include signal peptides from heterologous proteins. A "signal sequence" refers to a polynucleotide sequence that encodes a signal peptide. In some embodiments, an FGFR1 ECD lacks a signal peptide. In some embodiments, an FGFR1 ECD includes at least one signal peptide, which may be a native FGFR1 signal peptide or a heterologous signal peptide.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells; plant cells; and insect cells. Exemplary mammalian cells include, but are not limited to, 293 and CHO cells, and their derivatives, such as 293-6E and DG44 cells, respectively.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "anti-neoplastic composition" refers to a composition useful in treating cancer comprising at least one active therapeutic agent, e.g., an "anti-cancer agent." Examples of therapeutic agents (anti-cancer agents) include, but are not limited to, e.g., chemotherapeutic agents, growth inhibitory agents, cytotoxic agents, agents used in radiation therapy, anti-angiogenic agents, apoptotic agents, anti-tubulin agents, and other agents to treat cancer, such as anti-VEGF antibodies (e.g., bevacizumab, AVASTIN®), anti-HER-2 antibodies (e.g., trastuzumab, HERCEPTIN®) anti-CD20 antibodies (e.g., rituximab, RITUXAN®), an epidermal growth factor receptor (EGFR) antagonist (e.g., a tyrosine kinase inhibitor), HER1/EGFR inhibitors (e.g., erlotinib, TARCEVA®), platelet derived growth factor inhibitors (e.g., GLEEVEC®, imatinib mesylate)), COX-2 inhibitors (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

A "chemotherapeutic agent" refers to a chemical compound useful in the treatment of cancer. Examples of chemotherapeutic agents include alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMP- TOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e. g., calicheamicin, especially calicheamicin gammall and calicheamicin omegall (see, e.g., Nicolaou et al., *Angew. Chem Intl. Ed. Engl.,* 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), pegylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), pemetrexed (ALIMTA®); tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib, NEXAVAR®; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN®) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestins such as megestrol acetate and medroxyprogesterone acetate, estrogens such as diethylstilbestrol and premarin, and androgens/retinoids such as fluoxymesterone, all transretinoic acid and fenretinide; onapristone; anti-progesterones; estrogen receptor down-regulators (ERDs);

anti-androgens such as flutamide, nilutamide and bicalutamide; and pharmaceutically acceptable salts, acids or derivatives of any of the above; as well as combinations of two or more of the above.

An "angiogenic factor or agent" refers to a growth factor which stimulates the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family (VEGF-B, VEGF-C and VEGF-D), PlGF, PDGF family, fibroblast growth factor family (FGFs), TIE ligands (Angiopoietins), ephrins, delta-like ligand 4 (DLL4), del-1, fibroblast growth factors: acidic (aFGF) and basic (bFGF), follistatin, granulocyte colony-stimulating factor (G-CSF), hepatocyte growth factor (HGF)/scatter factor (SF), interleukin-8 (IL-8), leptin, midkine, neuropilins, placental growth factor, platelet-derived endothelial cell growth factor (PD-ECGF), platelet-derived growth factor, especially PDGF-BB or PDGFR-beta, pleiotrophin (PTN), progranulin, proliferin, transforming growth factor-alpha (TGF-alpha), transforming growth factor-beta (TGF-beta), tumor necrosis factor-alpha (TNF-alpha), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12):1359-1364; Tonini et al. (2003) *Oncogene* 22:6549-6556 (e.g., Table 1 listing known angiogenic factors); and, Sato (2003) *Int. J. Clin. Oncol.* 8:200-206.

An "anti-angiogenic agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenic agent includes those agents that bind and block the angiogenic activity of the angiogenic factor or its receptor. For example, an anti-angiogenic agent is an antibody or other antagonist to an angiogenic agent as defined above, e.g., fusion proteins that binds to VEGF-A such as ZALTRAP™ (Aflibercept), antibodies to VEGF-A such as AVASTIN® (bevacizumab) or to the VEGF-A receptor (e.g., KDR receptor or Flt-1 receptor), anti-PDGFR inhibitors such as GLEEVEC® (Imatinib Mesylate), small molecules that block VEGF receptor signaling (e.g., PTK787/ZK2284, SU6668, SUTENT®/SU11248 (sunitinib malate), AMG706, or those described in, e.g., international patent application WO 2004/113304). Anti-angiogenic agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known anti-angiogenic factors); and, Sato (2003) *Int. J. Clin. dOncol.* 8:200-206 (e.g., Table 1 listing anti-angiogenic agents used in clinical trials).

The term "VEGF" or "VEGF-A" as used herein refers to the 165-amino acid human vascular endothelial cell growth factor and related 121-, 189-, and 206-amino acid human vascular endothelial cell growth factors, as described by Leung et al. (1989) *Science* 246:1306, and Houck et al. (1991) *Mol. Endocrin,* 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)," "VEGF-$A_{109}$" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

A "VEGF antagonist" refers to a molecule capable of neutralizing, blocking, inhibiting, abrogating, reducing or interfering with VEGF activities including, but not limited to, its binding to one or more VEGF receptors. VEGF antagonists include, without limitation, anti-VEGF antibodies and antigen-binding fragments thereof, receptor molecules and derivatives which bind specifically to VEGF thereby sequestering its binding to one or more receptors, anti-VEGF receptor antibodies, VEGF receptor antagonists such as small molecule inhibitors of the VEGFR tyrosine kinases (e.g., pazopanib) and immunoadhesins that binds to VEGF such as VEGF trap (e.g., aflibercept). The term "VEGF antagonist," as used herein, specifically includes molecules, including antibodies, antibody fragments, other binding polypeptides, peptides, and non-peptide small molecules, that bind to VEGF and are capable of neutralizing, blocking, inhibiting, abrogating, reducing or interfering with VEGF activities. Thus, the term "VEGF activities" specifically includes VEGF mediated biological activities of VEGF.

The term "VEGF trap" as used herein means a protein, such as a fusion molecule, that binds to VEGF and is capable of neutralizing, blocking, inhibiting, abrogating, reducing or interfering with VEGF activities. An example of a VEGF trap is aflibercept.

The term "anti-VEGF antibody" or "an antibody that binds to VEGF" refers to an antibody that is capable of binding to VEGF with sufficient affinity and specificity that the antibody is useful as a diagnostic and/or therapeutic agent in targeting VEGF. Anti-VEGF neutralizing antibodies suppress the growth of a variety of human tumor cell lines in nude mice (Kim et al., *Nature* 362:841-844 (1993); Warren et al., *J. Clin. Invest.* 95:1789-1797 (1995); Borgström et al., *Cancer Res.* 56:4032-4039 (1996); Melnyk et al., *Cancer Res.* 56:921-924 (1996)) and also inhibit intraocular angiogenesis in models of ischemic retinal disorders. Adamis et al., *Arch. Ophthalmol.* 114:66-71 (1996). For example, the anti-VEGF antibody can be used as a therapeutic agent in targeting and interfering with diseases or conditions wherein the VEGF activity is involved. See, e.g., U.S. Pat. Nos. 6,582,959, 6,703,020; WO98/45332; WO 96/30046; WO94/10202, WO2005/044853; EP 0666868B1; US Patent Applications 20030206899, 20030190317, 20030203409, 20050112126, 20050186208, and 20050112126; Popkov et al., *Journal of Immunological Methods* 288:149-164 (2004); and WO2005012359. The antibody selected will normally have a sufficiently strong binding affinity for VEGF. For example, the antibody may bind hVEGF with a $K_d$ value of between 100 nM-1 pM.

Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. The antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B, VEGF-C, VEGF-D or VEGF-E, nor other growth factors such as PlGF, PDGF or bFGF.

In one embodiment, anti-VEGF antibodies include a monoclonal antibody that binds to the same epitope as the monoclonal anti-VEGF antibody A4.6.1 produced by hybridoma ATCC HB 10709; a recombinant humanized anti-VEGF monoclonal antibody (see Presta et al. (1997) *Cancer Res.* 57:4593-4599), including but not limited to the antibody known as "bevacizumab" also known as "rhuMAb VEGF" or "AVASTIN®." AVASTIN® is presently commercially available. Nonlimiting exemplary cancers that may be treated with bevacizumab include non-small cell lung cancer, colorectal cancer, breast cancer, renal cancer, ovarian cancer, glioblastoma multiforme, pediatric osteosarcoma, gastric cancer and pancreatic cancer. Bevacizumab comprises mutated human IgG$_1$ framework regions and antigen-binding complementarity-determining regions from the murine antibody A.4.6.1 that blocks binding of human VEGF to its receptors. Bevacizumab and other humanized anti-VEGF antibodies are further described in U.S. Pat. Nos. 6,884,879, and 7,169,901. Additional anti-VEGF antibodies are described in PCT Application Publication Nos. WO2005/012359 and WO2009/073160; U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004).

The terms "subject" and "patient" are used interchangeably herein to refer to a mammal. In some embodiments, the subject or patient is a human. In other embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The term "sample" or "patient sample" as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", or "reference tissue", as used herein, refers to a sample, cell or tissue obtained from a source known, or believed, not to be afflicted with the disease or condition for which a method or composition of the invention is being used to identify. In some embodiments, a reference sample, reference cell or reference tissue is obtained from a healthy part of the body of the same subject or patient in whom a disease or condition is being identified using a composition or method of the invention. In some embodiments, a reference sample, reference cell or reference tissue is obtained from a healthy part of the body of one or more individuals who are not the subject or patient in whom a disease or condition is being identified using a composition or method of the invention.

"Cancer" and "tumor," as used herein, are interchangeable terms that refer to any abnormal cell or tissue growth or proliferation in an animal. As used herein, the terms "cancer" and "tumor" encompass solid and hematological/lymphatic cancers and also encompass malignant, pre-malignant, and benign growth, such as dysplasia. Examples of cancer include but are not limited to, carcinoma, lymphoma, blastoma, sarcoma, and leukemia. More particular non-limiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

The term "lung cancer," as used herein, refers to both small cell lung cancer and non-small cell lung cancers. Non-small cell lung cancer includes, but is not limited to, squamous cell lung cancer, adenocarcinoma, large-cell lung carcinoma, sarcomatoid carcinoma, carcinoid tumors, pulmonary pleomorphic carcinoma, and adenosquamous carcinoma and bronchioloalveolar carcinoma. Small cell lung cancer may, in some embodiments, be referred to as "oat-cell" cancer, and includes, but is not limited to, combined small-cell carcinoma, which comprises a mixture of small cell and non-small cell carcinomas.

A "cell with FGFR1 gene amplification" refers to a cell that comprises more than two copies of the FGFR1 gene. In some embodiments, a cell with FGFR1 gene amplification refers to a cell that has a ratio of FGFR1 gene to chromosome 8 centromere of greater than 1. In some embodiments, the ratio is determined by fluorescence in situ hybridization. "Cancer with FGFR1 gene amplification," as used herein, refers to a cancer in which at least a portion of the cancer cells have FGFR1 gene amplification. In some embodiments, a cancer with FGFR1 gene amplification refers to a cancer in which at least a portion of the cancer cells comprise at least four copies of the FGFR1 gene. In some embodiments, a cancer with FGFR1 gene amplification refers to a cancer in which at least a portion of the cancer cells have an FGFR1 gene:chromosome 8 centromere ratio of greater than 1. An exemplary FGFR1 gene sequence can be found, e.g., NCBI Reference Sequence: NG_007729.1 dated 25 Mar. 2012.

In some embodiments, a cell with FGFR1 gene amplification comprises at least 3 copies, at least 4 copies, at least 5 copies, at least 6 copies, at least 8 copies, or at least 10 copies of the FGFR1 gene. In some embodiments, a cell with FGFR1 gene amplification comprises at least 4 copies. In some embodiments, a cell with FGFR1 gene amplification has a ratio of FGFR1 gene:chromosome 8 centromere of at least 1.5, at least 2, at least 2.5, at least 3, at least 3.5, or at least 4. In some embodiments, a cell with FGFR1 gene amplification has a ratio of FGFR1 gene:chromosome 8 centromere of at least 2. In some embodiments, each copy of the FGFR1 gene in a cell with FGFR1 gene amplification need not be a complete copy of the FGFR1 gene. In some embodiments, a cell with FGFR1 gene amplification has elevated levels of FGFR1 (i.e., in some embodiments, a cell with FGFR1 gene amplification is also a cell with FGFR1 overexpression).

A "cell with FGFR1 overexpression" or a "cell that overexpresses FGFR1" refers to a cell that has at least a 2-fold greater level of FGFR1 mRNA or protein than a reference cell. A "cancer with FGFR1 overexpression" or a "cancer that overexpresses FGFR1" refers to a cancer in which at least a portion of the cells have at least a 2-fold greater level of FGFR1 mRNA or protein than a reference cell. In some embodiments, a cell with FGFR1 overexpression has at least 3-fold, at least 4-fold, at least 5-fold, at least 7-fold, or at least 10-fold greater level of FGFR1 mRNA or protein than a reference cell. The level of FGFR1 mRNA or protein can be determined by any suitable method including, but not limited to, the methods described herein. In some embodiments, FGFR1 is FGFR1IIIc. An exemplary human FGFR1 protein sequence can be found, e.g., at UniProtKB/Swiss-Prot Reference Sequence: P11362 (FGFR1_HUMAN) dated Mar. 21, 2012. An exemplary human FGFR1 mRNA sequence can be found, e.g., at NCBI Reference Sequence: NM_023110.2 dated 24 Mar. 2012. An exemplary human FGFR1IIIc protein sequence can be found, e.g., at NCBI Reference Sequence: NP_075598.2 dated 24 Mar. 2012. An exemplary human FGFR1IIIc mRNA sequence can be found, e.g., at NCBI Reference Sequence: NM_023110.2 dated 24 Mar. 2012.

A "cell with FGFR3IIIc overexpression" or a "cell that overexpresses FGFR3IIIc" refers to a cell that has at least a 2-fold greater level of FGFR3IIIc mRNA or protein than a reference cell. A "cancer with FGFR3IIIc overexpression" or a "cancer that overexpresses FGFR3IIIc" refers to a cancer in which at least a portion of the cells have at least a 2-fold greater level of FGFR3IIIc mRNA or protein than a reference cell. In some embodiments, a cell with FGFR3IIIc overexpression has at least 3-fold, at least 4-fold, at least 5-fold, at least 7-fold, or at least 10-fold greater level of FGFR3IIIc mRNA or protein than a reference cell. The level of FGFR3IIIc mRNA or protein can be determined by any suitable method including, but not limited to, the methods described herein. An exemplary human FGFR3IIIc protein sequence can be found, e.g., at NCBI Reference Sequence: NP_000133.1 dated 12 Feb. 2012. An exemplary human FGFR3IIIc mRNA sequence can be found, e.g., at NCBI Reference Sequence: NM_000142.4 dated 12 Feb. 2012.

A "cell with FGF2 overexpression" or a "cell that overexpresses FGF2" refers to a cell that has at least a 2-fold greater level of FGF2 mRNA or protein than a reference cell. A "cancer with FGF2 overexpression" or a "cancer that overexpresses FGF2" refers to a cancer in which at least a portion of the cells have at least a 2-fold greater level of FGF2 mRNA or protein than a reference cell. In some embodiments, a cell with FGF2 overexpression has at least 3-fold, at least 4-fold, at least 5-fold, at least 7-fold, or at least 10-fold greater level of FGF2 mRNA or protein than a reference cell. The level of FGF2 mRNA or protein can be determined by any suitable method including, but not limited to, the methods described herein. An exemplary human FGF2 protein sequence can be found, e.g., at NCBI Reference Sequence: NP_001997.5 dated 12 Feb. 2012. An exemplary human FGF2 mRNA sequence can be found, e.g., at NCBI Reference Sequence: NM_002006.4 dated 12 Feb. 2012.

A "cell with DKK3 overexpression" or a "cell that overexpresses DKK3" refers to a cell that has at least a 2-fold greater level of DKK3 mRNA or protein than a reference cell. A "cancer with DKK3 overexpression" or a "cancer that overexpresses DKK3" refers to a cancer in which at least a portion of the cells have at least a 2-fold greater level of DKK3 mRNA or protein than a reference cell. In some embodiments, a cell with DKK3 overexpression has at least 3-fold, at least 4-fold, at least 5-fold, at least 7-fold, or at least 10-fold greater level of DKK3 mRNA or protein than a reference cell. The level of DKK3 mRNA or protein can be determined by any suitable method including, but not limited to, the methods described herein. An exemplary human DKK3 protein sequence can be found, e.g., at NCBI Reference Sequence: NP_001018067.1 dated 22 Jan. 2012. An exemplary human DKK3 mRNA sequence can be found, e.g., at NCBI Reference Sequence: NM_001018057.1 dated 22 Jan. 2012.

A "cell with FGF18 overexpression" or a "cell that overexpresses FGF18" refers to a cell that has at least a 2-fold greater level of FGF18 mRNA or protein than a reference cell. A "cancer with FGF18 overexpression" or a "cancer that overexpresses FGF18" refers to a cancer in which at least a portion of the cells have at least a 2-fold greater level of FGF18 mRNA or protein than a reference cell. In some embodiments, a cell with FGF18 overexpression has at least 3-fold, at least 4-fold, at least 5-fold, at least 7-fold, or at least 10-fold greater level of FGF18 mRNA or protein than a reference cell. The level of FGF18 mRNA or protein can be determined by any suitable method including, but not limited to, the methods described herein. An exemplary human FGF18 protein sequence can be found, e.g., at NCBI Reference Sequence: NP_003853 dated 27 Jun. 2012. An exemplary human FGF18 mRNA sequence can be found, e.g., at NCBI Reference Sequence: NM_003862.2 dated 27 Jun. 2012.

A "cell with ETV4 overexpression" or a "cell that overexpresses ETV4" refers to a cell that has at least a 2-fold greater level of ETV4 mRNA or protein than a reference cell. A "cancer with ETV4 overexpression" or a "cancer that overexpresses ETV4" refers to a cancer in which at least a portion of the cells have at least a 2-fold greater level of ETV4 mRNA or protein than a reference cell. In some embodiments, a cell with ETV4 overexpression has at least 3-fold, at least 4-fold, at least 5-fold, at least 7-fold, or at least 10-fold greater level of ETV4 mRNA or protein than a reference cell. The level of ETV4 mRNA or protein can be determined by any suitable method including, but not limited to, the methods described herein. An exemplary human ETV4 protein sequence can be found, e.g., at NCBI Reference Sequence: NP_001977.1 dated 8 Sep. 2012. An exemplary human ETV4 mRNA sequence can be found, e.g., at NCBI Reference Sequence: NM_001986.2 dated 8 Sep. 2012.

"Treatment," as used herein, includes any administration or application of a therapeutic for condition in a mammal, including a human, and includes inhibiting the condition or progression of the condition, inhibiting or slowing the condition or its progression, arresting its development, partially or fully relieving the condition, or curing the condition, for example, by causing regression, or restoring or repairing a lost, missing, or defective function; or stimulating an inefficient process. In some embodiments, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

An "effective amount" or "therapeutically effective amount" of a molecule or a combination of molecules means an amount that is sufficient to treat a condition and/or to inhibit growth of tumor cells in at least a subset of subjects when given alone or in combination with other treatments. In certain embodiments, a therapeutically effective amount refers to an amount effective, at dosages and for periods of time necessary, to achieve the desired therapeutic or prophylactic result. A therapeutically effective amount of FGFR1 fusion protein of the invention may vary according to factors such as the disease state, age, sex, and weight of the individual, and the ability of FGFR1 fusion protein to elicit a desired response in the individual. A therapeutically effective amount is also one in which any toxic or detrimental effects of the FGFR1 fusion proteins are outweighed by the therapeutically beneficial effects. In the case of cancer, the effective amount of the drug may reduce the number of cancer cells; reduce the tumor size; inhibit (i.e., slow to some extent and typically stop) cancer cell infiltration into peripheral organs; inhibit (i.e., slow to some extent and typically stop) tumor metastasis; inhibit, to some extent, tumor growth; allow for treatment of the tumor, and/or relieve to some extent one or more of the symptoms associated with the disorder. To the extent the drug may prevent growth and/or kill existing cancer cells, it may be cytostatic and/or cytotoxic.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "inhibition" or "inhibit" refer to a decrease or cessation of any phenotypic characteristic or to the decrease or cessation in the incidence, degree, or likelihood of that characteristic. Nonlimiting exemplary inhibition includes inhibition of tumor growth.

The terms "benefit", "clinical benefit", "responsiveness", and "therapeutic responsiveness" as used herein in the context of benefiting from or responding to administration of a therapeutic agent, can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

Administration "in combination with" one or more further therapeutic agents includes concurrent (including simultaneous) and consecutive (i.e., sequential) administration in any order.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Therapeutic Compositions and Methods

Methods of Treating Cancer Having FGFR1 Gene Amplifications Using FGFR1 ECDs and/or FGFR1 ECD Fusion Molecules In some embodiments, the invention provides methods of treating cancers in which at least a portion of the cancer cells have FGFR1 gene amplification. Such cancers have been found, in some embodiments, to be particularly responsive to treatment with a fibroblast growth factor receptor 1 (FGFR1) extracellular domain (ECD) or FGFR1 ECD fusion molecule. Accordingly, in some embodiments, a method of treating cancer having an FGFR1 gene amplification comprises administering a therapeutically effective amount of an FGFR1 ECD or an FGFR1 ECD fusion molecule to the subject. In some embodiments, a method of treating cancer in a subject comprises administering a therapeutically effective amount of a fibroblast growth factor receptor 1 (FGFR1) extracellular domain (ECD) or an FGFR1 ECD fusion molecule to the subject, wherein, prior to administration of the FGFR1 ECD or FGFR1 ECD fusion molecule, at least a portion of the cells of the cancer have been determined to have an FGFR1 gene amplification. In such methods, an FGFR1 gene amplification in a cancer is indicative of therapeutic responsiveness by the cancer to an FGFR1 ECD or FGFR1 ECD fusion molecule.

In some embodiments, the invention provides methods of treating cancers in which at least a portion of the cancer cells have overexpression of at least one, at least two, at least three, or at least four markers selected from FGFR1, FGFR3IIIc, FGF2, DKK3, FGF18, and ETV4. In some embodiments, FGFR1 is FGFR1IIIc. In some embodiments, the overexpression is mRNA overexpression. In some embodiments, the overexpression is protein overexpression. In some embodiments, a method of treating cancer that overexpresses at least marker selected from FGFR1, FGFR3IIIc, FGF2, DKK3, FGF18, and ETV4 comprises administering a therapeutically effective amount of an FGFR1 ECD or an FGFR1 ECD fusion molecule to the subject. In some embodiments, a method of treating cancer in a subject comprises administering a therapeutically effective amount of a fibroblast growth factor receptor 1 (FGFR1) extracellular domain (ECD) or an FGFR1 ECD fusion molecule to the subject, wherein, prior to administration of the FGFR1 ECD or FGFR1 ECD fusion molecule, at least a portion of the cells of the cancer have been determined to have overexpression of at least marker selected from FGFR1, FGFR3IIIc, FGF2, DKK3, FGF18, and ETV4. In such methods, FGFR1, FGFR3IIIc, FGF2, DKK3, FGF18, and/or ETV4 overexpression in a cancer is indicative of therapeutic responsiveness by the cancer to an FGFR1 ECD or FGFR1 ECD fusion molecule. In some embodiments, FGFR1 is FGFR1IIIc.

In some embodiments, in a cancer with an FGFR1 gene amplification, at least a portion of the cancer cells comprise at least four copies of the FGFR1 gene. In some embodiments, in a cancer with an FGFR1 gene amplification, at least a portion of the cancer cells comprise at least five, at least six, at least 8, or at least 10 copies of the FGFR1 gene. Determination of the FGFR1 gene copy number can be carried out by any suitable method in the art. Certain nonlimiting exemplary methods are discussed herein. In some embodiments, in a cancer with an FGFR1 gene amplification, at least a portion of the cancer cells have a ratio of FGFR1 gene to chromosome 8 centromere of at least 2. In some embodiments, in a cancer with an FGFR1 gene amplification, at least a portion of the cancer cells have a ratio of FGFR1 gene to chromosome 8 centromere of at least 2.5, at least 3, at least 3.5, or at least 4. Determination of such a ratio can be carried out by any suitable method in the art. Certain nonlimiting exemplary methods are discussed herein.

In some embodiments, the cancer is selected from prostate cancer, breast cancer, colorectal cancer, lung cancer, brain cancer, ovarian cancer, endometrial cancer, head and neck cancer, laryngeal cancer, liver cancer, renal cancer, glioblastoma, and pancreatic cancer. In certain embodiments, the cancer is selected from breast cancer, esophageal cancer, and lung cancer. In some embodiments, the cancer is lung cancer. In some embodiments, the lung cancer is selected from non-small cell lung cancer and small cell lung cancer. In some embodiments, the lung cancer is squamous cell carcinoma. In some embodiments, the cancer is head and neck cancer. In some embodiments, the head and neck cancer is squamous cell carcinoma of the head and neck.

In some embodiments, the FGFR1 ECD has an amino acid sequence selected from SEQ ID NOs: 1 to 4. In some embodiments, the FGFR1 ECD has an amino acid sequence selected from SEQ ID NOs: 2 and 4. In some embodiments, the FGFR1 ECD fusion molecule has an amino acid sequence selected from SEQ ID NOs: 5 and 6. In some embodiments, the FGFR1 ECD fusion molecule is FGFR1 ECD.339-Fc with an amino acid sequence of SEQ ID NO: 6.

In some embodiments, an FGFR1 ECD or FGFR1 ECD fusion molecule is administered with one or more additional anti-cancer therapies. Examples of the additional anti-cancer therapies include, without limitation, surgery, radiation therapy (radiotherapy), biotherapy, immunotherapy, and chemotherapy or a combination of these therapies. In addition, cytotoxic agents, anti-angiogenic and anti-proliferative agents can be used in combination with the FGFR1 ECD or FGFR1 ECD fusion molecule. In certain aspects of any of the methods and uses, the invention provides treating cancer in which at least a portion of the cancer cells comprise an FGFR1 gene amplification and/or overexpress at least one, at least two, at least three, or at least four markers selected from FGFR1, FGFR3IIIc, FGF2, DKK3, FGF18, and ETV4, by administering therapeutically effective amounts of an FGFR1 ECD and/or FGFR1 ECD fusion molecule and one or more chemotherapeutic agents to a subject. In some embodiments, the subject's cancer has not previously been treated. A variety of chemotherapeutic agents may be used in the combined treatment methods and uses of the invention. An exemplary and non-limiting list of chemotherapeutic agents contemplated is provided herein under "Definitions" and in the "Summary of the Invention." In some embodiments, the invention provides methods of treating cancer, by administering therapeutically effective amounts of an FGFR1 ECD and/or FGFR1 ECD fusion molecule and one or more anti-angiogenic agent(s) to a subject. In some embodiments, the invention provides treating cancer, by administering therapeutically effective amounts of an FGFR1 ECD and/or FGFR1 ECD fusion molecule and one or more VEGF antagonists to a subject. In some embodiments, the invention provides treating cancer, by administering therapeutically effective amounts of an FGFR1 ECD and/or FGFR1 ECD fusion molecule and one or more VEGF antagonists in combination with one or more chemotherapeutic agents to a subject. In some embodiments, the one or more VEGF antagonists are anti-VEGF antibodies and/or VEGF traps.

In some embodiments, methods of treating cancer comprising administering to a subject an FGFR1 ECD and/or FGFR1 ECD fusion molecule in combination with at least one additional therapeutic agent selected from docetaxel, paclitaxel, vincristine, carboplatin, cisplatin, oxaliplatin, doxorubicin, 5-fluorouracil (5-FU), leucovorin, pemetrexed, sorafenib, etoposide, topotecan, a VEGF antagonist, an anti-VEGF antibody, a VEGF trap, and bevacizumab are provided. In another example, methods of treating cancer comprising administering to a subject an FGFR1-ECD.339-Fc in combination with at least one additional therapeutic agent selected from docetaxel, paclitaxel, vincristine, carboplatin, cisplatin, oxaliplatin, doxorubicin, 5-fluorouracil (5-FU), leucovorin, pemetrexed, sorafenib, etoposide, topotecan, a VEGF antagonist, an anti-VEGF antibody, a VEGF trap, and bevacizumab are provided. In some embodiments, methods of treating cancer comprising administering to a subject an FGFR1-ECD.339-Fc and docetaxel are provided.

Pharmaceutical compositions comprising FGFR1 ECD and/or FGFR1 ECD fusion molecules (e.g., FGFR1-ECD.339-Fc) are administered in a therapeutically effective amount for the specific indication. The therapeutically effective amount is typically dependent on the weight of the subject being treated, his or her physical or health condition, the extensiveness of the condition to be treated, and/or the age of the subject being treated. In general, an FGFR1 ECD and/or FGFR1 ECD fusion molecule (e.g., FGFR1-ECD.339-Fc) is to be administered in an amount in the range of about 50 µg/kg body weight to about 100 mg/kg body weight per dose. Optionally, the FGFR1 ECD and/or FGFR1 ECD fusion molecule (e.g., FGFR1-ECD.339-Fc) can be administered in an amount in the range of about 100 µg/kg body weight to about 30 mg/kg body weight per dose. Further optionally, the FGFR1 ECD and/or FGFR1 ECD fusion molecule (e.g., FGFR1-ECD.339-Fc) can be administered in an amount in the range of about 0.5 mg/kg body weight to about 20 mg/kg body weight per dose. In certain embodiments, the FGFR1 ECD and/or FGFR1 ECD fusion molecule (e.g., FGFR1-ECD.339-Fc) is administered at a dose of about 8 mg/kg body weight to about 20 mg/kg body weight. In some embodiments, the FGFR1 ECD and/or FGFR1 ECD fusion molecule (e.g., FGFR1-ECD.339-Fc) is administered at a dose of about 8 mg/kg body weight to about 16 mg/kg body weight (or about 10 mg/kg body weight to about 20 mg/kg body weight when calculated using an extinction coefficient of 1.11 mL/mg*cm). In some embodiments, the FGFR1 ECD and/or FGFR1 ECD fusion molecule (e.g., FGFR1-ECD.339-Fc) is administered at a dose of about 8 mg/kg body weight, about 10 mg/kg body weight, about 11 mg/kg body weight, about 12 mg/kg body weight, about 13 mg/kg body weight, about 14 mg/kg body weight, about 15 mg/kg body weight, about 16 mg/kg body weight, about 17 mg/kg body weight, about 18 mg/kg body weight, about 19 mg/kg body weight, or about 20 mg/kg body weight. In some embodiments, the FGFR1 fusion protein is administered at a dose of about 10 mg/kg body weight as calculated using an extinction coefficient of 1.11 mL/mg*cm. In other embodiments, the FGFR1 fusion protein is administered at a dose of about 20 mg/kg body weight as calculated using an extinction coefficient of 1.11 mL/mg*cm. The FGFR1 ECD and/or FGFR1 ECD fusion molecules may also be administered at ranges from one of the above doses to another. In some embodiments, dosages may be administered twice a week, weekly, every other week, at a frequency between weekly and every other week, every three weeks, every four weeks, or every month.

In certain embodiments, dosages of the FGFR1 ECD and/or FGFR1 ECD fusion molecules can be calculated in two ways depending on the extinction coefficient (EC) used. The extinction coefficient differs depending on whether the glycosylation of the proteins is taken into account. In one embodiment, the extinction coefficient based on the amino acid composition of FGFR1-ECD.339-Fc, for example, is 1.42 mL/mg*cm. In another embodiment, when the carbohydrate portion as well as the amino acid portion of FGFR1-ECD.339-Fc is accounted for, the extinction coefficient is 1.11 mL/mg*cm. Calculation of the FGFR1-ECD.339-Fc dose using an EC of 1.11 mL/mg*cm increases the calculated dose by 28%, as shown in Table 1. Although the doses calculated using the two extinction coefficients are different, the molar concentrations, or the actual amounts of drug administered, are identical. Unless otherwise noted, the doses disclosed herein are each calculated using the extinction coefficient that does not take account of glycosylation. How these dosages compare to those calculated using the extinction coefficient that takes account of glycosylation for FGFR1-ECD.339-Fc is shown in Table 1. As can be seen from Table 1, a dosage of about 8 mg/kg (e.g., 7.8 and 8.0) using an EC of 1.42 mL/mg*cm herein corresponds to a dosage of about 10 mg/kg (e.g. 10.0 and 10.2) when calculated using an EC of 1.11 mL/mg*cm. A dosage of about 16 mg/kg (e.g. 15.6 and 16.0 mg/kg) using an EC of 1.42 mL/mg*cm herein corresponds to a dosage of about 20 mg/kg (e.g. 20.0 and 20.5) when calculated using an EC of 1.11 mL/mg*cm. As noted in the "Definitions" section above, measured numbers provided herein are approximate and encompass values having additional significant digits that are rounded off. For instance, 8 mg/kg encompasses values with two significant digits such as 7.6, 7.8, 8.0, 8.2, 8.4, and 8.45, each of which round to 8. Likewise, a value such as 16 mg/kg encompasses values with three significant digits that round to 16, such as, for example 15.6 and 16.0.

TABLE 1

Conversion of FGFR1-ECD.339-FC Dose

| Dose$^a$ EC = 1.42 mL/mg * cm | Dose$^a$ EC = 1.11 mL/mg * cm |
|---|---|
| 0.5 | 0.6 |
| 0.75 | 1.0 |
| 1.0 | 1.3 |
| 2.0 | 2.6 |
| 3.0 | 3.8 |
| 4.0 | 5.1 |
| 5.0 | 6.4 |
| 6.0 | 7.7 |
| 7.0 | 9.0 |
| 7.8 | 10.0 |
| 8.0 | 10.2 |
| 9.0 | 11.5 |
| 10.0 | 12.8 |
| 11.0 | 14.1 |
| 12.0 | 15.4 |
| 13.0 | 16.6 |
| 14.0 | 17.9 |
| 15.0 | 19.2 |
| 15.6 | 20.0 |
| 16.0 | 20.5 |
| 17.0 | 21.8 |
| 18.0 | 23.0 |
| 19.0 | 24.3 |
| 20.0 | 25.6 |
| 30.0 | 38.4 |

$^a$Doses shown in mg/kg.

The pharmaceutical compositions comprising FGFR1 ECDs, FGFR1 ECD fusion molecules, and/or at least one additional therapeutic agent can be administered as needed to subjects. In certain embodiments, an effective dose of a therapeutic molecule is administered to a subject one or more times. In various embodiments, an effective dose of a therapeutic molecule is administered to the subject at least once every two months, at least once a month, at least twice a month, once a week, twice a week, or three times a week. In various embodiments, an effective dose of a therapeutic molecule is administered to the subject for at least a week, at least a month, at least three months, at least six months, or at least a year.

In certain embodiments, the combined administration of an FGFR1 ECDs, FGFR1 ECD fusion molecule and at least one additional therapeutic agent includes concurrent administration, including simultaneous administration, using separate formulations or a single pharmaceutical formulation, as well as consecutive administration in any order. Optionally there is a time period while both (or all) active agents simultaneously exert their biological activities. Therapeutically effective amounts of therapeutic agents administered in combination with the FGFR1 ECD and/or FGFR1 ECD fusion molecule (e.g., FGFR1-ECD.339-Fc) will be at the physician's or veterinarian's discretion. Dosage administration and adjustment is done to achieve maximal management of the conditions to be treated. The dose will additionally depend on such factors as the type of therapeutic agent to be used, the specific patient being treated, the stage of the disease, and the desired aggressiveness of the treatment regime.

In certain embodiments, a patient is treated with a combination of the FGFR1 ECD and/or FGFR1 ECD fusion molecule (e.g., FGFR1-ECD.339-Fc) and a VEGF antagonist. In some embodiments, the VEGF antagonist is a VEGF trap (e.g., aflibercept). In some embodiments, the VEGF antagonist is a tyrosine kinase inhibitor (e.g., pazopanib). In some embodiments, the VEGF antagonist is an anti-VEGF antibody. In some embodiments, the VEGF antibody is bevacizumab. One exemplary dosage of bevacizumab is in the range from about 0.05 mg/kg to about 20 mg/kg. Thus, one or more doses of about 0.5 mg/kg, 2.0 mg/kg, 4.0 mg/kg, 7.5 mg/kg, 10 mg/kg or 15 mg/kg (or any combination thereof) may be administered to the patient. Such doses may be administered intermittently, e.g., every week, every two, or every three weeks.

In some embodiments, the FGFR1 ECD and/or FGFR1 ECD fusion molecule (e.g., FGFR1-ECD.339-Fc) is administered in combination with another therapeutic agent, such as chemotherapeutic agent or anti-angiogenic agent, at the recommended or prescribed dosage and/or frequency of the therapeutic agent.

In some embodiments, an additional therapeutic agent is administered at a dosage approved by an agency responsible for approving therapeutic treatments, such as the Food and Drug Administration, or at the manufacturer's recommended dosage.

Routes of Administration and Carriers

In some embodiments, an FGFR1 ECD and/or FGFR1 ECD fusion molecule can be administered intravenously and/or subcutaneously. In some embodiments, an FGFR1 ECD and/or FGFR1 ECD fusion molecule can be administered by another route, such as intra-arterial, parenteral, intranasal, intramuscular, intracardiac, intraventricular, intratracheal, buccal, rectal, intraperitoneal, intradermal, topical, transdermal, or intrathecal, or otherwise by implantation or inhalation. In various embodiments, at least one additional therapeutic agent can be administered in vivo by a variety of routes, including intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. Each of the subject compositions can be formulated alone or in combination into preparations in solid, semi-solid, liquid, or gaseous forms, such as tablets, capsules, powders, granules, ointments, solutions, suppositories, enemas, injections, inhalants, and aerosols.

In various embodiments, compositions comprising an FGFR1 ECD, FGFR1 ECD fusion molecule, and/or at least one additional therapeutic agent are provided in formulation with pharmaceutically acceptable carriers, a wide variety of which are known in the art (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, carriers, and diluents, are available to the public. Moreover, various pharmaceutically acceptable auxiliary substances, such as pH adjusting and buffering agents, tonicity adjusting agents, stabilizers, wetting agents and the like, are also available to the public. Certain non-limiting exemplary carriers include saline, buffered saline, dextrose, water, glycerol, ethanol, and combinations thereof. In some embodiments, a therapeutic agent is formulated as the brand-name drug indicated above in the Definitions section, or a generic equivalent. In some embodiments, docetaxel is formulated as Taxotere® (Sanofi Aventis) or a generic equivalent.

In various embodiments, compositions comprising FGFR1 ECDs, FGFR1 ECD fusion molecules, and/or at least one additional therapeutic agent can be formulated for injection by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical dosage packs comprising one or more containers, each containing one or more doses of an FGFR1 ECD, an FGFR1 ECD fusion molecule, and/or at least one additional therapeutic agent are also provided. In certain embodiments, a unit dosage is provided wherein the unit dosage contains a predetermined amount of a composition comprising an FGFR1 ECD, an FGFR1 ECD fusion molecule, and/or at least one additional therapeutic agent with or without one or more additional agents. In certain embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that can be reconstituted upon addition of an appropriate liquid, for example, sterile water. In certain embodiments, a composition comprises one or more substances that inhibit protein aggregation, including, but not limited to, sucrose and arginine. In certain embodiments, a composition of the invention comprises heparin and/or a proteoglycan.

In some embodiments, a dosage pack comprises instructions to determine whether a cancer comprises an FGFR1 gene amplification and/or overexpresses at least one, at least two, at least three, or at least four markers selected from FGFR1, FGFR3IIIc, FGF2, DKK3, FGF18, and ETV4 prior to administering an FGFR1 ECD and/or an FGFR1 ECD fusion molecule. In some embodiments, FGFR1 is FGFR1IIIc. In some such embodiments, the instructions indicate that the presence of an FGFR1 gene amplification and/or overexpression of at least one, at least two, at least three, or at least four markers selected from FGFR1, FGFR3IIIc, FGF2, DKK3, FGF18, and ETV4 in at least a portion of the cancer cells is indicative of therapeutic responsiveness to an FGFR1 ECD and/or an FGFR1 ECD fusion molecule. In some embodiments, the instructions indicate that the presence of at least four copies of an FGFR1 gene in at least a portion of the cancer cells is indicative of therapeutic responsiveness to an FGFR1 ECD and/or an FGFR1 ECD fusion molecule. In some embodiments, the instructions indicate that the presence of at least four, at least six, at least eight, or at least ten copies of an FGFR1 gene in at least a portion of the cancer cells is indicative of therapeutic responsiveness to an FGFR1 ECD and/or an FGFR1 ECD fusion molecule. In some embodiments, the instructions indicate that a ratio of FGFR1 gene to chromosome 8 centromere of at least 2 in at least a portion of the cancer cells is indicative of therapeutic responsiveness to an FGFR1 ECD and/or an FGFR1 ECD fusion molecule. In some embodiments, the instructions indicate that a ratio of FGFR1 gene to chromosome 8 centromere of at least 2.5, at least 3, at least 3.5, or at least 4 in at least a portion of the lung cancer cells is indicative of therapeutic responsiveness to an FGFR1 ECD and/or an FGFR1 ECD fusion molecule.

In some embodiments, a dosage pack comprises instructions to determine whether a lung cancer comprises an FGFR1 gene amplification and/or overexpresses at least one, at least two, at least three, or at least four markers selected from FGFR1, FGFR3IIIc, FGF2, DKK3, FGF18, and ETV4 prior to administering an FGFR1 ECD and/or an FGFR1 ECD fusion molecule. In some embodiments, FGFR1 is FGFR1IIIc. In some such embodiments, the instructions indicate that the presence of an FGFR1 gene amplification and/or overexpression of at least one, at least two, at least three, or at least four markers selected from FGFR1, FGFR3IIIc, FGF2, DKK3, FGF18, and ETV4 in at least a portion of the lung cancer cells is indicative of therapeutic responsiveness to an FGFR1 ECD and/or an FGFR1 ECD fusion molecule. In some embodiments, the instructions indicate that the presence of at least four copies of an FGFR1 gene in at least a portion of the lung cancer cells is indicative of therapeutic responsiveness to an FGFR1 ECD and/or an FGFR1 ECD fusion molecule. In some embodiments, the instructions indicate that the presence of at least four, at least six, at least eight, or at least ten copies of an FGFR1 gene in at least a portion of the lung cancer cells is indicative of therapeutic responsiveness to an FGFR1 ECD and/or an FGFR1 ECD fusion molecule. In some embodiments, the instructions indicate that a ratio of FGFR1 gene to chromosome 8 centromere of at least 2 in at least a portion of the lung cancer cells is indicative of therapeutic responsiveness to an FGFR1 ECD and/or an FGFR1 ECD fusion molecule. In some embodiments, the instructions indicate that a ratio of FGFR1 gene to chromosome 8 centromere of at least 2.5, at least 3, at least 3.5, or at least 4 in at least a portion of the lung cancer cells is indicative of therapeutic responsiveness to an FGFR1 ECD and/or an FGFR1 ECD fusion molecule.

The term "instructions," as used herein includes, but is not limited to, labels, package inserts, instructions available in electronic form such as on a computer readable medium (e.g., a diskette, compact disk, or DVD), instructions available remotely such as over the internet, etc. A dosage pack is considered to include the instructions when the dosage pack provides access to the instructions, a link to the instructions (such as a uniform resource locator, or url), or other mechanism for obtaining a copy of the instructions (such as a return reply card, a physical address from which instructions may be requested, an e-mail address from which instructions may be requested, a phone number that may be called to obtain instructions, etc.).

FGFR1 ECDs and FGFR1 ECD Fusion Molecules

Nonlimiting exemplary FGFR1 ECDs include full-length FGFR1 ECDs, FGFR1 ECD fragments, and FGFR1 ECD variants. FGFR1 ECDs may include or lack a signal peptide. Exemplary FGFR1 ECDs include, but are not limited to, FGFR1 ECDs having amino acid sequences selected from SEQ ID NOs.: 1, 2, 3, and 4.

Non-limiting exemplary FGFR1 ECD fragments include human FGFR1 ECD ending at amino acid 339 (counting from the first amino acid of the mature form, without the signal peptide). In some embodiments, an FGFR1 ECD fragment ends at an amino acid between amino acid 339 and amino acid 360 (counting from the first amino acid of the mature form, without the signal peptide). Exemplary FGFR1 ECD fragments include, but are not limited to, FGFR1 ECD fragments having amino acid sequences selected from SEQ ID NOs.: 3 and 4.

In some embodiments, an FGFR1 ECD comprises a sequence selected from SEQ ID NOs: 1 to 4. In some embodiments, an FGFR1 ECD consists of a sequence selected from SEQ ID NOs: 1 to 4. When an FGFR1 ECD "consists of" a sequence selected from SEQ ID NOs: 1 to 4, the FGFR1 ECD may or may not contain various post-translational modifications, such as glycosylation and sialylation. In other words, when an FGFR1 ECD consists of a particular amino acid sequence, it does not contain additional amino acids in the contiguous amino acid sequence, but may contain modifications to amino acid side chains, the N-terminal amino group, and/or the C-terminal carboxy group.

In some embodiments, an FGFR1 ECD fusion molecule comprises a signal peptide. In some embodiments, an FGFR1 ECD fusion molecule lacks a signal peptide. In some embodiments, the FGFR1 ECD portion of an FGFR1 ECD fusion molecule comprises a sequence selected from SEQ ID NOs: 1 to 4. In some embodiments, the FGFR1 ECD portion of an FGFR1 ECD fusion molecule consists of a sequence selected from SEQ ID NOs: 1 to 4. When an FGFR1 ECD portion of an FGFR1 ECD fusion molecule "consists of" a sequence selected from SEQ ID NOs: 1 to 4, the FGFR1 ECD portion of an FGFR1 ECD fusion molecule may or may not contain various post-translational modifications, such as glycosylation and sialylation. In other words, when an FGFR1 ECD portion of an FGFR1 ECD fusion molecule consists of a particular amino acid sequence, it does not contain additional amino acids from FGFR1 in the contiguous amino acid sequence, but may contain modifications to amino acid side chains, the N-terminal amino group, and/or the C-terminal carboxy group. Further, because the FGFR1 ECD is linked to a fusion molecule, there may be additional amino acids at the N- and/or C-terminus of the FGFR1 ECD, but those amino acids are not from the FGFR1 sequence, but may be from, for example, a linker sequence, or a fusion partner sequence.

In some embodiments, the fusion partner portion of an FGFR1 ECD fusion molecule is selected from Fc, albumin, and polyethylene glycol. Nonlimiting exemplary fusion partners are discussed herein.

The inventors have found that administration of an FGFR1 ECD and/or an FGFR1 ECD fusion molecule and at least one additional therapeutic agent selected from docetaxel, paclitaxel, vincristine, carboplatin, cisplatin, oxaliplatin, doxorubicin, 5-fluorouracil (5-FU), leucovorin, pemetrexed, sorafenib, etoposide, topotecan, a VEGF antagonist, pazopanib, an anti-VEGF antibody, a VEGF trap, and bevacizumab is useful for treating cancers in which at least a portion of the cancer cells have FGFR1 gene amplification and/or overexpress at least one, at least two, at least three, or at least four markers selected from FGFR1, FGFR3IIIc, FGF2, DKK3, FGF18, and ETV4. In some embodiments, FGFR1 is FGFR1IIIc. In some embodiments, an FGFR1 ECD and/or an FGFR1 ECD fusion molecule is administered with docetaxel.

Fusion Partners and Conjugates

As discussed herein, an FGFR1 ECD may be combined with at least one fusion partner, resulting in an FGFR1 ECD fusion molecule. These fusion partners may facilitate purification, and the FGFR1 ECD fusion molecules may show an increased half-life in vivo. Suitable fusion partners of an FGFR1 ECD include, for example, polymers, such as water soluble polymers, the constant domain of immunoglobulins;

all or part of human serum albumin (HSA); fetuin A; fetuin B; a leucine zipper domain; a tetranectin trimerization domain; mannose binding protein (also known as mannose binding lectin), for example, mannose binding protein 1; and an Fc region, as described herein and further described in U.S. Pat. No. 6,686,179. Nonlimiting exemplary FGFR1 ECD fusion molecules are described, e.g., in U.S. Pat. No. 7,678,890.

An FGFR1 ECD fusion molecule may be prepared by attaching polyaminoacids or branch point amino acids to the FGFR1 ECD. For example, the polyaminoacid may be a carrier protein that serves to increase the circulation half life of the FGFR1 ECD (in addition to the advantages achieved via a fusion molecule). For the therapeutic purpose of the present invention, such polyaminoacids should ideally be those that have or do not create neutralizing antigenic responses, or other adverse responses. Such polyaminoacids may be chosen from serum albumin (such as HSA), an additional antibody or portion thereof, for example the Fc region, fetuin A, fetuin B, leucine zipper nuclear factor erythroid derivative-2 (NFE2), neuroretinal leucine zipper, tetranectin, or other polyaminoacids, for example, lysines. As described herein, the location of attachment of the polyaminoacid may be at the N terminus or C terminus, or other places in between, and also may be connected by a chemical linker moiety to the selected molecule.

Polymers

Polymers, for example, water soluble polymers, may be useful as fusion partners to reduce precipitation of the FGFR1 ECD fusion molecule in an aqueous environment, such as typically found in a physiological environment. Polymers employed in the invention will be pharmaceutically acceptable for the preparation of a therapeutic product or composition.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3, 6-trioxane, ethylene/maleic anhydride copolymer, poly (β-amino acids) (either homopolymers or random copolymers), poly(n-vinyl pyrrolidone) polyethylene glycol, polypropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll, or dextran and mixtures thereof.

As used herein, polyethylene glycol (PEG) is meant to encompass any of the forms that have been used to derivatize other proteins, such as mono-($C_1$-$C_{10}$) alkoxy- or aryloxy-polyethylene glycol. Polyethylene glycol propionaldehyde may have advantages in manufacturing due to its stability in water.

Polymers used herein, for example water soluble polymers, may be of any molecular weight and may be branched or unbranched. In some embodiments, the polymers have an average molecular weight of between about 2 kDa to about 100 kDa (the term "about" indicating that in preparations of a polymer, some molecules will weigh more, some less, than the stated molecular weight). The average molecular weight of each polymer may be between about 5 kDa and about 50 kDa, or between about 12 kDa and about 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on an FGFR1 ECD.

Polymers employed in the present invention are typically attached to an FGFR1 ECD with consideration of effects on functional or antigenic domains of the polypeptide. In general, chemical derivatization may be performed under any suitable condition used to react a protein with an activated polymer molecule. Activating groups which can be used to link the polymer to the active moieties include sulfone, maleimide, sulfhydryl, thiol, triflate, tresylate, azidirine, oxirane, and 5-pyridyl.

Polymers of the invention are typically attached to a heterologous polypeptide at the alpha (α) or epsilon (ε) amino groups of amino acids or a reactive thiol group, but it is also contemplated that a polymer group could be attached to any reactive group of the protein that is sufficiently reactive to become attached to a polymer group under suitable reaction conditions. Thus, a polymer may be covalently bound to an FGFR1 ECD via a reactive group, such as a free amino or carboxyl group. The amino acid residues having a free amino group may include lysine residues and the N-terminal amino acid residue. Those having a free carboxyl group may include aspartic acid residues, glutamic acid residues, and the C-terminal amino acid residue. Those having a reactive thiol group include cysteine residues.

Methods for preparing fusion molecules conjugated with polymers, such as water soluble polymers, will each generally involve (a) reacting an FGFR1 ECD with a polymer under conditions whereby the polypeptide becomes attached to one or more polymers and (b) obtaining the reaction product. Reaction conditions for each conjugation may be selected from any of those known in the art or those subsequently developed, but should be selected to avoid or limit exposure to reaction conditions such as temperatures, solvents, and pH levels that would inactivate the protein to be modified. In general, the optimal reaction conditions for the reactions will be determined case-by-case based on known parameters and the desired result. For example, the larger the ratio of polymer:polypeptide conjugate, the greater the percentage of conjugated product. The optimum ratio (in terms of efficiency of reaction in that there is no excess unreacted polypeptide or polymer) may be determined by factors such as the desired degree of derivatization (e.g., mono-, di-, tri-, etc.), the molecular weight of the polymer selected, whether the polymer is branched or unbranched and the reaction conditions used. The ratio of polymer (for example, PEG) to a polypeptide will generally range from 1:1 to 100:1. One or more purified conjugates may be prepared from each mixture by standard purification techniques, including among others, dialysis, salting-out, ultrafiltration, ion-exchange chromatography, gel filtration chromatography, and electrophoresis.

One may specifically desire an N-terminal chemically modified FGFR1 ECD. One may select a polymer by molecular weight, branching, etc., the proportion of polymers to FGFR1 ECD molecules in the reaction mix, the type of reaction to be performed, and the method of obtaining the selected N-terminal chemically modified FGFR1 ECD. The method of obtaining the N-terminal chemically modified FGFR1 ECD preparation (separating this moiety from other monoderivatized moieties if necessary) may be by purification of the N-terminal chemically modified FGFR1 ECD material from a population of chemically modified protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N terminus with a carbonyl group-containing polymer is achieved. For example, one may selectively attach a polymer to the N terminus of the protein by performing the reaction at a pH that allows one to take advantage of the pKa differences between the ε-amino group of the lysine residues and that of the α-amino group of the N-terminal residue of the protein. By such selective derivatization, attachment of a polymer to a protein is controlled: the conjugation with the polymer takes place predominantly at the N terminus of the protein and no significant modification of other reactive groups, such as the lysine side chain amino groups, occurs. Using reductive alkylation, the polymer may be of the type described above and should have a single reactive aldehyde for coupling to the protein. Polyethylene glycol propionaldehyde, containing a single reactive aldehyde, may also be used.

In one embodiment, the present invention contemplates the chemically derivatized FGFR1 ECD to include mono- or poly- (e.g., 2-4) PEG moieties. Pegylation may be carried out by any of the pegylation reactions available. Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions will be determined case by case based on known parameters and the desired result.

There are a number of PEG attachment methods known in the art. See, for example, EP 0 401 384; Malik et al., *Exp. Hematol.,* 20:1028-1035 (1992); Francis, *Focus on Growth Factors,* 3(2):4-10 (1992); EP 0 154 316; EP 0 401 384; WO 92/16221; WO 95/34326; and the other publications cited herein that relate to pegylation.

Pegylation may be carried out, e.g., via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (for example, those containing 2-6 or 2-5 PEG groups). The PEG groups are generally attached to the protein at the α- or ε-amino groups of amino acids, but it is also contemplated that the PEG groups could be attached to any amino group attached to the protein that is sufficiently reactive to become attached to a PEG group under suitable reaction conditions.

Pegylation by acylation generally involves reacting an active ester derivative of polyethylene glycol (PEG) with an FGFR1 ECD. For acylation reactions, the polymer(s) selected typically have a single reactive ester group. Any known or subsequently discovered reactive PEG molecule may be used to carry out the pegylation reaction. An example of a suitable activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like, see for example, Chamow, *Bioconjugate Chem.,* 5:133-140 (1994). Reaction conditions may be selected from any of those currently known or those subsequently developed, but should avoid conditions such as temperature, solvent, and pH that would inactivate the polypeptide to be modified.

Pegylation by acylation will generally result in a poly-pegylated protein. The connecting linkage may be an amide. The resulting product may be substantially only (e.g., >95%) mono-, di-, or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography, and electrophoresis.

Pegylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono $C_1$-$C_{10}$ alkoxy or aryloxy derivatives thereof, see for example, U.S. Pat. No. 5,252,714.

Markers

Moreover, FGFR1 ECDs of the present invention may be fused to marker sequences, such as a peptide that facilitates purification of the fused polypeptide. The marker amino acid sequence may be a hexa-histidine peptide such as the tag provided in a pQE vector (Qiagen, Mississauga, Ontario, Canada), among others, many of which are commercially available. As described in Gentz et al., *Proc. Natl. Acad. Sci.* 86:821-824 (1989), for instance, hexa-histidine provides for convenient purification of the fusion protein. Another peptide tag useful for purification, the hemagglutinin (HA) tag, corresponds to an epitope derived from the influenza HA protein. (Wilson et al., *Cell* 37:767 (1984)). Any of these above fusions may be engineered using the FGFR1 ECDs described herein.

Oligomerization Domain Fusion Partners

In various embodiments, oligomerization offers some functional advantages to a fusion protein, including, but not limited to, multivalency, increased binding strength, and the combined function of different domains. Accordingly, in some embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains; and certain immunoglobulin domains. Exemplary coiled-coil polypeptide fusion partners include, but are not limited to, the tetranectin coiled-coil domain; the coiled-coil domain of cartilage oligomeric matrix protein; angiopoietin coiled-coil domains; and leucine zipper domains. Exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that may be used as fusion partners are known in the art. In some embodiments, a fusion partner is an Fc immunoglobulin domain. An Fc fusion partner may be a wild-type Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Additional exemplary Fc fusion partners include, but are not limited to, human IgA and IgM. In some embodiments, an Fc fusion partner comprises a C237S mutation, for example, in an IgG1 (see, for example, SEQ ID NO: 8). In some embodiments, an Fc fusion partner comprises a hinge, CH2, and CH3 domains of human IgG2 with a P331S mutation, as described in U.S. Pat. No. 6,900,292. Certain exemplary Fc domain fusion partners are shown in SEQ ID NOs: 8 to 10.

Albumin Fusion Partners and Albumin-Binding Molecule Fusion Partners

In some embodiments, a fusion partner is an albumin. Exemplary albumins include, but are not limited to, human serum album (HSA) and fragments of HSA that are capable of increasing the serum half-life or bioavailability of the polypeptide to which they are fused. In some embodiments, a fusion partner is an albumin-binding molecule, such as, for example, a peptide that binds albumin or a molecule that conjugates with a lipid or other molecule that binds albumin. In some embodiments, a fusion molecule comprising HSA is prepared as described, e.g., in U.S. Pat. No. 6,686,179.

Exemplary Attachment of Fusion Partners

The fusion partner may be attached, either covalently or non-covalently, to the N terminus or the C terminus of the FGFR1 ECD. The attachment may also occur at a location within the FGFR1 ECD other than the N terminus or the C terminus, for example, through an amino acid side chain (such as, for example, the side chain of cysteine, lysine, serine, or threonine).

In either covalent or non-covalent attachment embodiments, a linker may be included between the fusion partner and the FGFR1 ECD. Such linkers may be comprised of at least one amino acid or chemical moiety. Exemplary methods of covalently attaching a fusion partner to an FGFR1 ECD include, but are not limited to, translation of the fusion partner and the FGFR1 ECD as a single amino acid sequence and chemical attachment of the fusion partner to the FGFR1 ECD. When the fusion partner and an FGFR1 ECD are translated as single amino acid sequence, additional amino acids may be included between the fusion partner and the FGFR1 ECD as a linker. In some embodiments, the linker is selected based on the polynucleotide sequence that encodes it, to facilitate cloning the fusion partner and/or FGFR1 ECD into a single expression construct (for example, a polynucleotide containing a particular restriction site may be placed between the polynucleotide encoding the fusion partner and the polynucleotide encoding the FGFR1 ECD, wherein the polynucleotide containing the restriction site encodes a short amino acid linker sequence). When the fusion partner and the FGFR1 ECD are covalently coupled by chemical means, linkers of various sizes may typically be included during the coupling reaction.

Exemplary methods of non-covalently attaching a fusion partner to an FGFR1 ECD include, but are not limited to, attachment through a binding pair. Exemplary binding pairs include, but are not limited to, biotin and avidin or streptavidin, an antibody and its antigen, etc.

Co-Translational and Post-Translational Modifications

The invention encompasses administration of FGFR1 ECDs and FGFR1 ECD fusion molecules that are differentially modified during or after translation, for example by glycosylation, acetylation, phosphorylation, amidation, derivatization by known protecting/blocking groups, proteolytic cleavage, or linkage to an antibody molecule or other cellular ligand. Any of numerous chemical modifications may be carried out by known techniques, including, but not limited to, specific chemical cleavage by cyanogen bromide, trypsin, chymotrypsin, papain, V8 protease; $NABH_4$; acetylation; formylation; oxidation; reduction; and/or metabolic synthesis in the presence of tunicamycin.

Additional post-translational modifications encompassed by the invention include, for example, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. A nonlimiting discussion of various post-translational modifications of FGFR1 ECDs and FGFR1 ECD fusion molecules can be found, e.g., in U.S. Pat. No. 7,678,890.

FGFR1 ECD and FGFR1 ECD Fusion Molecule Expression and Production Vectors

Vectors comprising polynucleotides that encode FGFR1 ECDs are provided. Vectors comprising polynucleotides that encode FGFR1 ECD fusion molecules are also provided. Such vectors include, but are not limited to, DNA vectors, phage vectors, viral vectors, retroviral vectors, etc.

In some embodiments, a vector is selected that is optimized for expression of polypeptides in CHO or CHO-derived cells. Exemplary such vectors are described, e.g., in Running Deer et al., *Biotechnol. Prog.* 20:880-889 (2004).

In some embodiments, a vector is chosen for in vivo expression of FGFR1 ECDs and/or FGFR1 ECD fusion molecules in animals, including humans. In some such embodiments, expression of the polypeptide is under the control of a promoter that functions in a tissue-specific manner. For example, liver-specific promoters are described, e.g., in PCT Publication No. WO 2006/076288. A nonlimiting discussion of various expression vectors can be found, e.g., in U.S. Pat. No. 7,678,890.

Host Cells

In various embodiments, FGFR1 ECDs or FGFR1 ECD fusion molecules may be expressed in prokaryotic cells, such as bacterial cells; or in eukaryotic cells, such as fungal cells, plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO—S and DG44 cells; and NSO cells. In some embodiments, a particular eukaryotic host cell is selected based on its ability to make certain desired post-translational modifications to the FGFR1 ECDs or FGFR1 ECD fusion molecules. For example, in some embodiments, CHO cells produce FGFR1 ECDs and/or FGFR1 ECD fusion molecules that have a higher level of sialylation than the same polypeptide produced in 293 cells.

Introduction of a nucleic acid into a desired host cell may be accomplished by any method known in the art, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., *Molecular Cloning, A Laboratory Manual*, $3^{rd}$ ed. Cold Spring Harbor Laboratory Press (2001). Nucleic acids may be transiently or stably transfected in the desired host cells, according to methods known in the art. A nonlimiting discussion of host cells and methods of polypeptides in host cells can be found, e.g., in U.S. Pat. No. 7,678,890.

In some embodiments, a polypeptide may be produced in vivo in an animal that has been engineered or transfected with a nucleic acid molecule encoding the polypeptide, according to methods known in the art.

Purification of FGFR1 ECD Polypeptides

FGFR1 ECDs or FGFR1 ECD fusion molecules may be purified by various methods known in the art. Such methods include, but are not limited to, the use of affinity matrices or hydrophobic interaction chromatography. Suitable affinity ligands include any ligands of the FGFR1 ECD or of the fusion partner. Suitable affinity ligands in the case of an antibody that binds FGFR1 include, but are not limited to, FGFR1 itself and fragments thereof. Further, a Protein A, Protein G, Protein A/G, or an antibody affinity column may be used to bind to an Fc fusion partner to purify an FGFR1 ECD fusion molecule. Antibodies to FGFR1 ECD may also be used to purify FGFR1 ECD or FGFR1 ECD fusion molecules. Hydrophobic interactive chromatography, for example, a butyl or phenyl column, may also suitable for purifying some polypeptides. Many methods of purifying polypeptides are known in the art. A nonlimiting discussion of various methods of purifying polypeptides can be found, e.g., in U.S. Pat. No. 7,678,890.

Methods of Identifying Patients Who would Benefit from FGFR1 ECDs and/or FGFR1 ECD Fusion Molecules In some embodiments, methods of identifying patients with cancer who may benefit from administration of an FGFR1 ECD or FGFR1 ECD fusion molecule are provided. In some such embodiments, the method comprises determining whether at least a portion of the cancer cells comprise an FGFR1 gene amplification in a sample obtained from the subject. In some embodiments, FGFR1 gene amplification is indicative of therapeutic responsiveness by the cancer to an FGFR1 ECD or FGFR1 ECD fusion molecule. In some embodiments, a sample is taken from a patient having or suspected of having cancer. A finding of FGFR1 gene amplification in at least a portion of the cancer cells indicates that the patient having or suspected of having cancer may benefit from an FGFR1 ECD or FGFR1 ECD fusion molecule therapy. In some embodiments, the patient has or is suspected of having lung cancer.

In some embodiments, the method comprises determining whether at least a portion of the cancer cells comprise overexpression of at least one, at least two, at least three, or at least four markers selected from FGFR1, FGFR3IIIc, FGF2, DKK3, FGF18, and ETV4 in a sample obtained from the subject. In some embodiments, the overexpression is mRNA overexpression. In some embodiments, the overexpression is protein overexpression. In some embodiments, FGFR1, FGFR3IIIc, FGF2, DKK3, FGF18, and/or ETV4 overexpression is indicative of therapeutic responsiveness by the cancer to an FGFR1 ECD or FGFR1 ECD fusion molecule. In some embodiments, a sample is taken from a patient having or suspected of having cancer. A finding of FGFR1, FGFR3IIIc, FGF2, DKK3, FGF18, and/or ETV4 overexpression in at least a portion of the cancer cells indicates that the patient having or suspected of having cancer may benefit from an FGFR1 ECD or FGFR1 ECD fusion molecule therapy. In some embodiments, FGFR1 is FGFR1IIIc. In some embodiments, the patient has or is suspected of having lung cancer.

In some embodiments, FGFR1 gene amplification and/or overexpression of at least one, at least two, at least three, or at least four markers selected from FGFR1, FGFR3IIIc, FGF2, DKK3, FGF18, and ETV4 is determined by a laboratory. A laboratory may be a hospital laboratory or a laboratory independent of a hospital. In some embodiments, following a determination of FGFR1 gene amplification and/or overexpression of at least one, at least two, at least three, or at least four markers selected from FGFR1, FGFR3IIIc, FGF2, DKK3, FGF18, and ETV4, the results of the determination are communicated to a medical professional. In some such embodiments, the results are communicated for the purpose of determining whether a patient should benefit from, or be responsive to, an FGFR1 ECD or FGFR1 ECD fusion molecule therapy. In some embodiments, medical professionals include, but are not limited to, doctors, nurses, hospital administration and staff, etc. In some embodiments, FGFR1 is FGFR1IIIc.

Any suitable method of determining FGFR1 gene amplification may be used. Nonlimiting exemplary such methods include fluorescence in situ hybridization (FISH; see, e.g., Monni et al. (2001) *PNAS* 98: 5711-5716), array comparative genomic hybridization (aCGH), DNA microarrays (see, e.g., Carter et al. (2007) *Nat. Genet.* 39: S16-21), spectral karyotyping (SKY; see, e.g. Liyanage et al. (1996) *Nat. Genet.* 14: 312-5), real-time quantitative PCR (see, e.g., Dhaene et al. (2010) *Methods* 50: 262-270), southern blotting, and sequencing, including, but not limited to, high-throughput sequencing (HTS; see, e.g. Medvedev et al. (2010) *Genome Res.* 20: 1613-22), and next generation sequencing technologies such as RNA-seq, also called "Whole Transcriptome Shotgun Sequencing" ("WTSS"), Applied Biosystems SOLiD™ System, Illumina (Solexa) sequencing, Ion semiconductor sequencing, DNA nanoball sequencing, Helioscope™ single molecule sequencing, Single Molecule SMRT™ sequencing, Single Molecule real time (RNAP) sequencing, Nanopore DNA sequencing, VisiGen Biotechnologies approach, and 454 pyrosequencing.

Fluorescence in situ hybridization (FISH) is a cytogenetic technique to detect and localize the presence or absence of specific DNA sequences on chromosomes. In some embodiments, FISH uses fluorescent probes to detect certain regions of chromosomes in a sequence-specific manner. Thus, in some embodiments, to detect gene amplification in cancer using FISH, in some embodiments, a fluorescent probe is developed that binds specifically to the gene of interest, such as the FGFR1 gene. In some such embodiments, this gene specific probe is hybridized to a cancer sample and the copy number determined by counting the number of fluorescent signals present per cell using fluorescence microscopy. For a normal diploid cell, the majority of genes will have a copy number of two (exceptions exist when the gene is present on one of the sex chromosomes rather than an autosome or the cell is undergoing division and the genome replicated). If more than two signals are detected in a cell, in certain instances, the gene may be amplified.

Dual color FISH may also be used for assessing gene amplification in cancer. In some embodiments, a reference probe that binds to the centromere region of the chromosome on which the gene of interest is located can be used as a control. In some instances, the centromere (CEN) region of a chromosome is considered to be genomically stable and is therefore assumed to be representative of the entire chromosome. CEN copy number can therefore, in some embodiments, assist in distinguishing focal gene amplification from increased gene copy number resulting from polysomy ($\geq 3$ copies of the chromosome centromere) of the chromosome. Gene amplification can be distinguished from polysomy, in some embodiments, by calculating the ratio the signal from the gene-of-interest probe/signal from the centromere probe. For a normal diploid cell, where the gene of interest in located on an autosome, this ratio is typically 1. In some embodiments, a ratio of $>1$ is indicative of gene amplification. In some embodiments, a probe to a chromosomal reference gene can be used in place of, or in addition to, a centromere probe (see, e.g., Tse et al. (2011) *J. Clin. Oncol.* 29: 4168-74). In some embodiments, the selected reference gene is also on chromosome 8. In some embodiments, the reference gene is located close to the centromere of chromosome 8. In some embodiments, the reference sequence comprises non-coding DNA on chromosome 8.

In some embodiments, FISH allows the determination of multiple parameters of gene amplification, including, but not limited to, the fraction of cells with an amplified gene, the amplification levels within various subpopulations of cells, and the amplification pattern within a cell (for example, a clustered signal versus multiple scattered signals). In some embodiments, the ratio of the copy number of the gene of interest to the centromere reference for each cancer cell is determined. In some such embodiments, the mean ratio for a particular sample or subset of cells in a sample is then calculated. A mean ratio of greater than two is generally considered to indicate gene amplification, whereas signals between 1.5 to 2 may indicate low-level amplification. In some embodiments, cells that have a greater copy number of the gene of interest than a reference control probe are considered amplified (see, e.g., Kobayashi et al. (2002) *Hum. Pathol.* 33: 21-8; and Kunitomo et al. (2002) *Pathol. Int.* 52: 451-7). In embodiments, single-color FISH is used to determine the copy number of a gene of interest without a chromosomal reference probe control. In some such embodiments, four or more copies of the gene per nucleus is considered to be gene amplification (see, e.g., Couturier et al. (2000) *Mod. Pathol.* 13: 1238-43; Jacobs et al. (1999) *J. Clin. Oncol.* 17: 1974-82; Wang et al. (2000) *J. Clin. Pathol.* 53: 374-81).

Any suitable method of determining protein overexpression (FGFR1, FGFR3IIIc, FGF2, DKK3, FGF18, and/or ETV4 overexpression) may be used. In certain embodiments, the expression of proteins in a sample is examined using immunohistochemistry ("IHC") and staining protocols. Immunohistochemical staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods.

The tissue sample may be fixed (i.e. preserved) by conventional methodology (See e.g., "Manual of Histological Staining Method of the Armed Forces Institute of Pathology," $3^{rd}$ edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C.). One of skill in the art will appreciate that the choice of a fixative is determined by the purpose for which the sample is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a sample.

Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

In some embodiments, subsequent to the sample preparation, a tissue section may be analyzed using IHC. IHC may be performed in combination with additional techniques such as morphological staining and/or fluorescence in-situ hybridization. Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories: (a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting. (b) Colloidal gold particles. (c) Fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in Current Protocols in Immunology, supra, for example. fluorescence can be quantified using a fluorimeter. (d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed. J. Langone & H. Van Vunakis), Academic press, New York, 73:147-166 (1981).

Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-Nitrophenyl phosphate as chromogenic substrate; and (iii) .beta.-D-galactosidase (.beta.-D-Gal) with a chromogenic substrate (e.g., p-nitrophenyl-.beta.-D-galactosidase) or fluorogenic substrate (e.g., 4-methylumbelliferyl-.beta.-D-galactosidase).

Numerous other enzyme-substrate combinations are available to those skilled in the art. For a general review of these, see U.S. Pat. Nos. 4,275,149 and 4,318,980. Sometimes, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired. For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. In some embodiments, the label is an enzymatic label (e.g. HRPO) which catalyzes a chemical alteration of the chromogenic substrate such as 3,3'-diaminobenzidine chromogen. In one embodiment, the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and cover-slipped. Slide evaluation is then determined, e.g., using a microscope, and staining intensity criteria, routinely used in the art, may be employed.

In some embodiments, when IHC is used, a tiered system of staining is used to determine whether a cell or collection of cells overexpresses FGFR1 protein. For example, in some embodiments, a four-tiered system is used in which the tiers are no staining, 1+, 2+, and 3+, where 1+, 2+, and 3+ indicate increasing levels of staining, respectively. In some such embodiments, greater than 1+, greater than 2+, or greater than 3+ may be used to indicate FGFR1 protein overexpression. As a nonlimiting example, if a particular cell type typically shows no staining for FGFR1 in an IHC assay, then any staining in that IHC assay (i.e., 1+, 2+, or 3+) may be indicative as protein overexpression. As a further nonlimiting example, if a particular cell type typically shows little to no staining for FGFR1 in an IHC assay, then any staining above 1+ in that IHC assay (i.e., 2+ or 3+) may be indicative as protein overexpression. One skilled in the art can determine the staining level that indicates protein overexpression depending on the particular IHC assay (including the particular antibody), the cell type, etc.

Any suitable method of determining mRNA overexpression (such as FGFR1 overexpression, and/or FGF2 overexpression, and/or DKK3 overexpression, and/or FGF18 overexpression, and/or ETV4 overexpression) may be used. Methods for the evaluation of mRNAs in cells are well known and include, for example, hybridization assays using complementary DNA probes (such as in situ hybridization using labeled riboprobes specific for FGFR1, FGF2, DKK3, FGF18, or ETV4 Northern blot and related techniques) and various nucleic acid amplification assays (such as RT-PCR using complementary primers specific for FGFR1, FGFR1IIIc, FGFR3IIIc, FGF2, DKK3, FGF18, or ETV4 and other amplification type detection methods, such as, for example, branched DNA, SISBA, TMA and the like).

Tissue or cell samples from mammals can be conveniently assayed for mRNAs using Northern, dot blot or PCR analysis. For example, RT-PCR assays such as quantitative PCR assays are well known in the art. In some embodiments, mRNA expression levels are levels quantified using real-time qRT-PCR. In some embodiments of the invention, a method for detecting a target mRNA in a biological sample comprises producing cDNA from the sample by reverse transcription using at least one primer; amplifying the cDNA so produced using a target polynucleotide as sense and antisense primers to amplify target cDNAs therein; and detecting the presence of the amplified target cDNA. In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods of the invention include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (see, for example, U.S. Pat. Nos. 5,700,637, 5,445,934, and 5,807,522, Lockart, *Nature Biotechnology*, 14:1675-1680 (1996); Cheung, V. G. et al., *Nature Genetics* 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ). In some embodiments, a DNA microarray is a single-nucleotide polymorphism (SNP) microarrays, e.g., Affymetrix® SNP Array 6.0.

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from Genbank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

EXAMPLES

The examples discussed below are intended to be purely exemplary of the invention and should not be considered to limit the invention in any way. The examples are not intended to represent that the experiments below are all or the only experiments performed. It is understood that various other embodiments may be practiced, given the general description provided above. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: FGFR1-ECD.339-Fc Inhibits Proliferation of FGFR1 Amplified Lung Cancer Cell Lines in Tissue Culture A panel of lung cancer cell lines displaying potential amplification of the FGFR1 gene was identified using CONAN (http://www.sanger.ac.uk/cgi-bin/genetics/CGP/conan/search.cgi) and Tumorscape (http://www.broadinstitute.org/tumorscape/pages/portalHomejsf). CONAN and Tumorscape represent public data mining tools to extract gene copy number information for predefined or user defined loci across the SNP6.0 dataset of cancer. Lung cancer cell lines DMS53, DMS114, NCI-H1581 and NCI-H520 were identified as having potential amplification of the FGFR1 gene (>4 copies/cell) and were selected for further analysis. Human small cell lung cancer (SCLC) cell lines DMS53 and DMS114 were purchased from ATCC (Manassas, Va.; Cat. No. CRL-2062; Cat. No. CRL-2066, respectfully). The cells were cultured in Waymouth's MB 752/1 medium+10% FBS+2 mM L-glutamine at 37° C. in a humidified atmosphere with 5% $CO_2$. Human non-small cell lung cancer (NSCLC) cell line NCI-H1581 was purchased from ATCC (Manassas, Va.; Cat. No. CRL-5878) and cultured in ACL-4 medium (serum-free). The base medium for NCI-H1581 is DMEM: F12 (50/50 mix) with the following components to the base medium: 0.02 mg/ml insulin, 0.01 mg/ml transferrin, 25 nM sodium selenite (final conc.), 50 nM Hydrocortisone (final conc.), 1 ng/ml Epidermal Growth Factor (final conc.), 0.01 mM ethanolamine (final conc.), 0.01 mM phosphorylethanolamine (final conc.), 100 pM triiodothyronine (final conc.), 0.5% (w/v) bovine serum albumin (final conc.), 0.5 mM sodium pyruvate (final conc.) and 4.5 mM L-glutamine. Cells were grown at 37° C. in a humidified atmosphere with 5% CO2. Human non-small cell lung cancer (NSCLC) cell line NCI-H520 was purchased from ATCC (Manassas, Va.; Cat. No. HTB-182). The cells were cultured in RPMI-1640 Medium+10% FBS+2 mM L-glutamine at 37° C. in a humidified atmosphere with 5% $CO_2$.

Amplification status of the FGFR1 gene in the cell lines was confirmed by QuantiGene® Plex DNA Assay (Panomics). The QuantiGene Plex DNA Assay is a hybridization-based assay using xMAP® Luminex® magnetic beads. Individual, bead-based, oligonucleotide probe sets (including capture, capture extenders, blockers, and label probes) specific for FGFR1 (NM_023110), ALB (NM_000477) and DCK (NM_000788) genes were designed to prevent cross-reactivity (Panomics, Affymetrix, Santa Clara, Calif.). ALB and DCK were used as reference genes for normalizing FGFR1 copy number. Cell samples were lysed to release DNA and incubated overnight with FGFR1 target specific probe sets. On the second day a signal amplification tree was built via sequential hybridization of PreAmplifier (PreAmp), Amplifier (Amp) and biotinylated Label Probe (LP). The signal was detected by adding phycoerythrin streptavidin (SAPE) substrate. SAPE fluorescence was detected at 575 nm for each capture bead using a Luminex 200 flow cytometer instrument (Luminex, Austin, Tex.). All data were normalized to the reference genes and expressed as a ratio (FGFR1/ALB). Data for the four cell lines is shown in Table 2.

TABLE 2

FGFR1 gene amplification in lung cancer cell lines

| Cell Line (Lung tumor subtype) | FGFR1 Gene Status (Copy number) | FGFR1-ECD.339-Fc Growth Inhibition In vitro | In vivo (% TGI)* |
|---|---|---|---|
| DMS53 (SCLC) | Amplified (5 copies/cell) | + | + (64%) |
| DMS114 (SCLC) | Amplified (10 copies/cell) | + | + (64%) |
| NCI-H1581 (NSCLC) | Amplified (6 copies/cell) | + | + (74%) |
| NCI-H520 (NSCLC) | Amplified (8 copies/cell) | + | + (47%) |

*TGI = tumor growth inhibition.

To determine the impact of FGFR1-ECD.339-Fc on lung cancer cell lines in tissue culture, cells were plated in a Microtest™ 96-well tissue culture plate (Becton Dickenson, Franklin Lakes, N.J.) at a density of $5 \times 10^3$ cells/well in medium containing 10%, 1% or 0.1% FBS in the presence or absence of 15 µg/ml FGFR1-ECD.339-Fc (SEQ ID NO: 6) or an unrelated ECD-Fc fusion protein (as a negative control). Plates were incubated at 37° C. at 5% $CO_2$ for 4 days and then assayed to determine the impact of FGFR1-ECD.339-Fc on cell number and proliferation.

To determine cell number the CellTiter-Glo® Luminescent Cell Viability Assay (Promega, Madison, Wis.) was employed. CellTiter-Glo® is a homogeneous method of determining the number of viable cells in culture based on quantitation of the ATP present, an indicator of metabolically active cells. In brief, CellTiter-Glo® Reagent was added to each well of the tissue culture plate at a volume equal to the volume of cell culture medium present in each well (100 µl), the contents mixed for 2 minutes on an orbital shaker to induce cell lysis and then the plate incubated for 10 minutes at room temperature. Luminescence was then determined on an EnVision™ Multilabel Plate Reader (PerkinElmer, Boston, Mass.) with a 0.2 second integration time. Results were expressed as relative light units (RLU)/well.

Results from the CellTiter-Glo® assay demonstrated that cell number was significantly (P=>0.01) reduced by FGFR1-ECD.339-Fc incubation in all four cell lines with FGFR1 amplification (FIG. 1A-D show NCI-H1581, NCI-H520, DMS53, and DMS114, respectively). P-values were determined using an unpaired t-test. See *Mathematical Statistics and Data Analysis,* 1988, Wadsworth & Brooks, Pacific Grove, Calif.

To determine the impact of FGFR1-ECD.339-Fc on cell proliferation the tritiated thymidine ([3H]-TdR) incorporation assay was employed. Following incubation of lung cancer cell lines with FGFR1-ECD.339-Fc or an unrelated ECD-Fc negative control, tritiated thymidine ([3H]-TdR; PerkinElmer, Boston, Mass.) was added at activity of 1 µCi/well. After 16-h exposure, tritiated thymidine incorporation was assessed. Cells were washed with Dulbecco's phosphate-buffered saline (DPBS; Mediatech, Inc.) and removed from cell culture surface by incubation with trypsin-EDTA (Mediatech, Inc.). The cell suspension (200 µl) was then removed from the tissue culture plate using a FilterMate harvester (PerkinElmer) and filtered through a UniFilter-96 GF/B (PerkinElmer) plate. Cells were lysed using 95% ethanol and 40 µl of Microscint 40 (PerkinElmer) scintillant fluid added per well. Thymidine incorporation was determined as counts per minute (cpm) on a Topcount NXT (PerkinElmer) scintillation counter. Results were expressed as cpm/well.

In the tritiated thymidine incorporation assay, FGFR1-ECD.339-Fc reduced NCI-H1581, NCI-H520, DMS53, and DMS114 cell proliferation by 85, 33, 52 and 81%, respectively (FIG. 2A-D, respectively). The control ECD-Fc demonstrated no impact on cell proliferation in any cell line. An additional lung tumor cell line, NCI-H1703 (NSCLC; FGFR1 gene copy number: 6 copies/cell) was also tested in the tritiated thymidine incorporation assay following incubation with FGFR1-ECD.339-Fc, as described above. FGFR1-ECD.339-Fc reduced NCI-H1703 proliferation by 15%.

Figure 2:
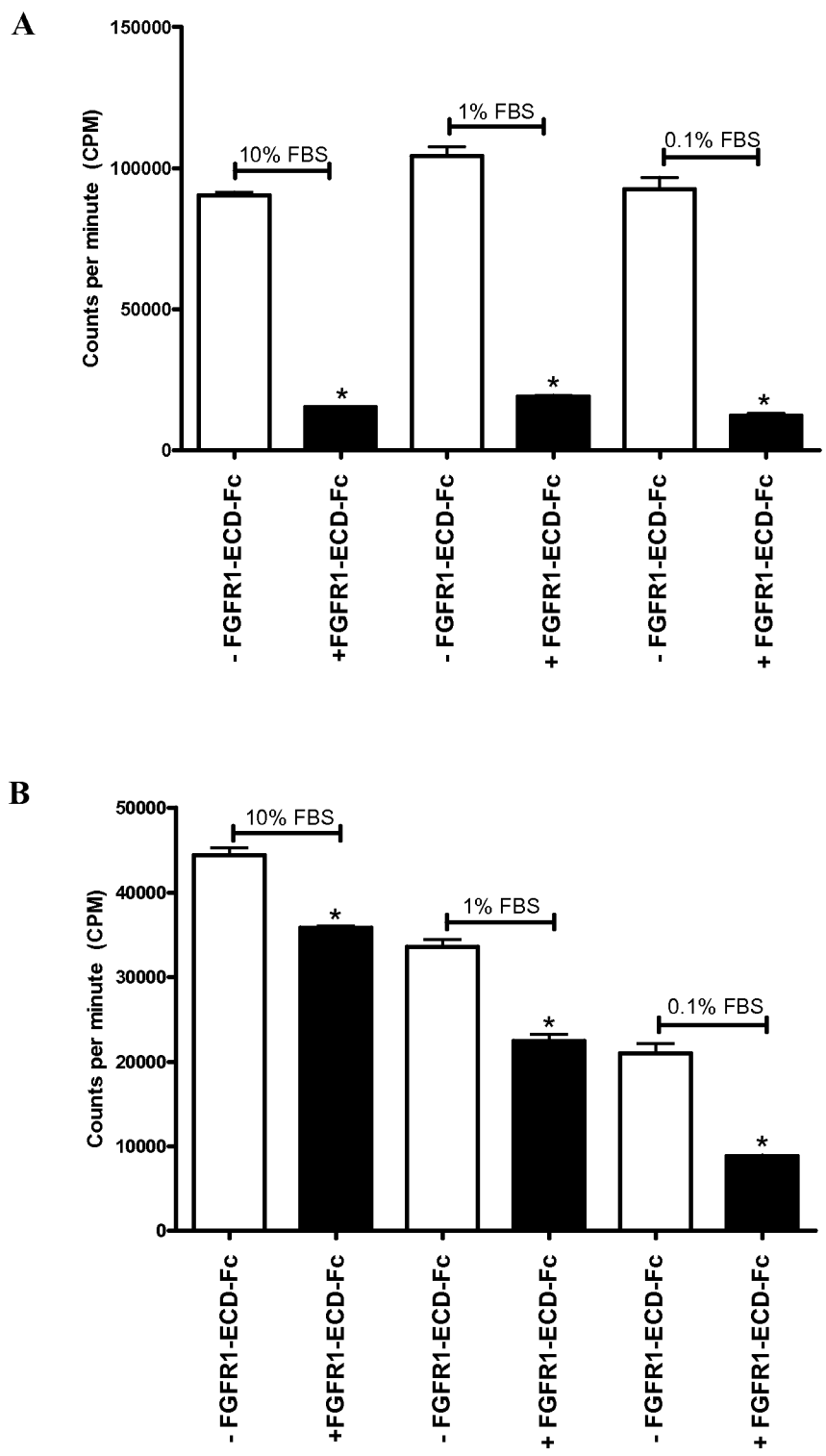
FIG. 2 shows thymidine incorporation by (A) NCI-H1581, (B) NCI-H520, (C) DMS53, and (D) DMS114 tumor cells grown in the presence or absence of FGFR1-ECD.339-Fc, with varying amounts of serum, as described in Example 1.
Figure 2:
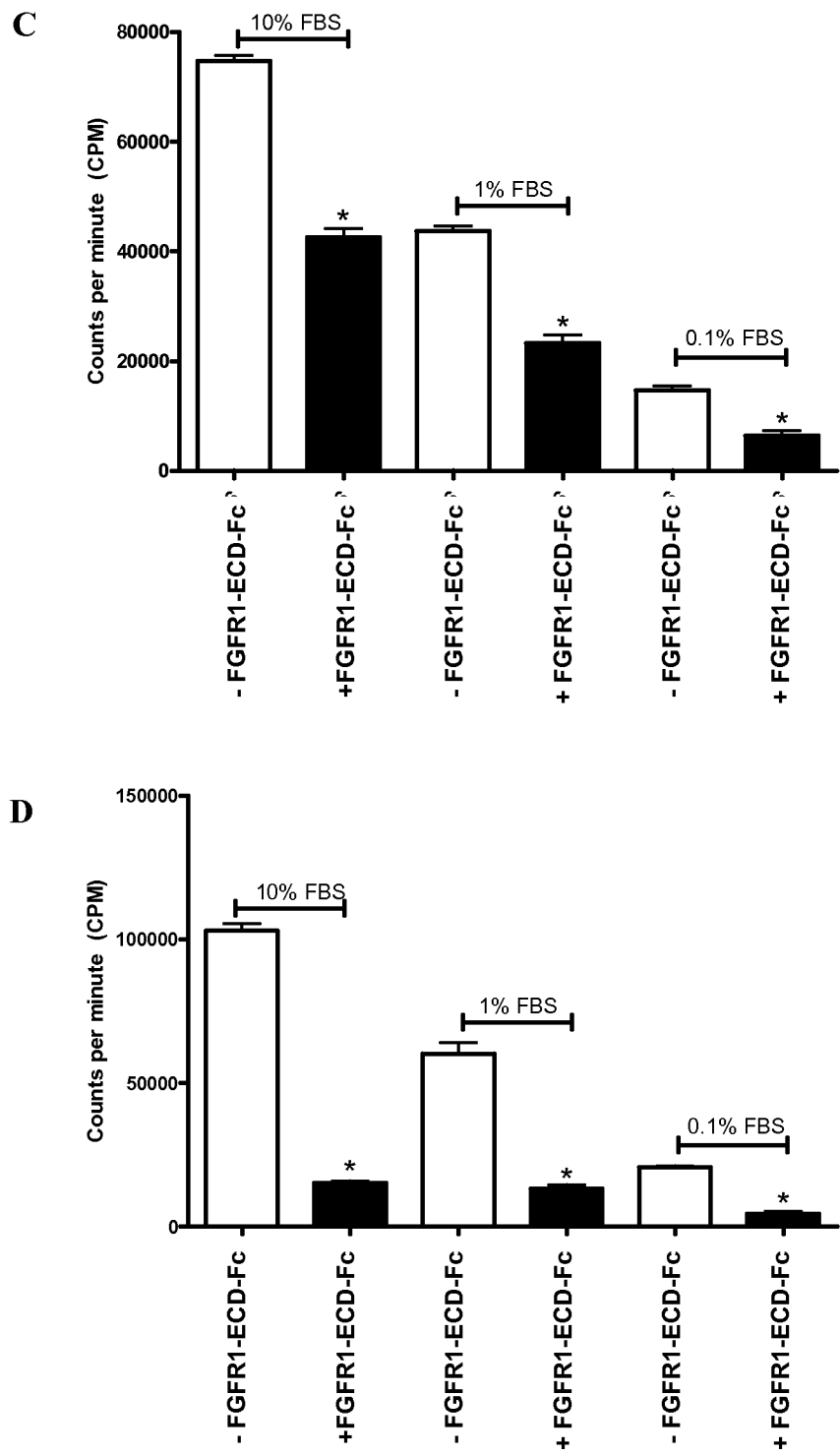

Results from the tritiated thymidine incorporation assay demonstrate that cell proliferation was significantly (* indicates P=>0.05) reduced by FGFR1-ECD.339-Fc incubation in all four cell lines with FGFR1 gene amplification (FIG. 2). P-values were determined using an unpaired t-test. See *Mathematical Statistics and Data Analysis,* 1988, Wadsworth & Brooks, Pacific Grove, Calif. The control ECD Fc had little no impact on cell proliferation in any cell line.

Figure 3:
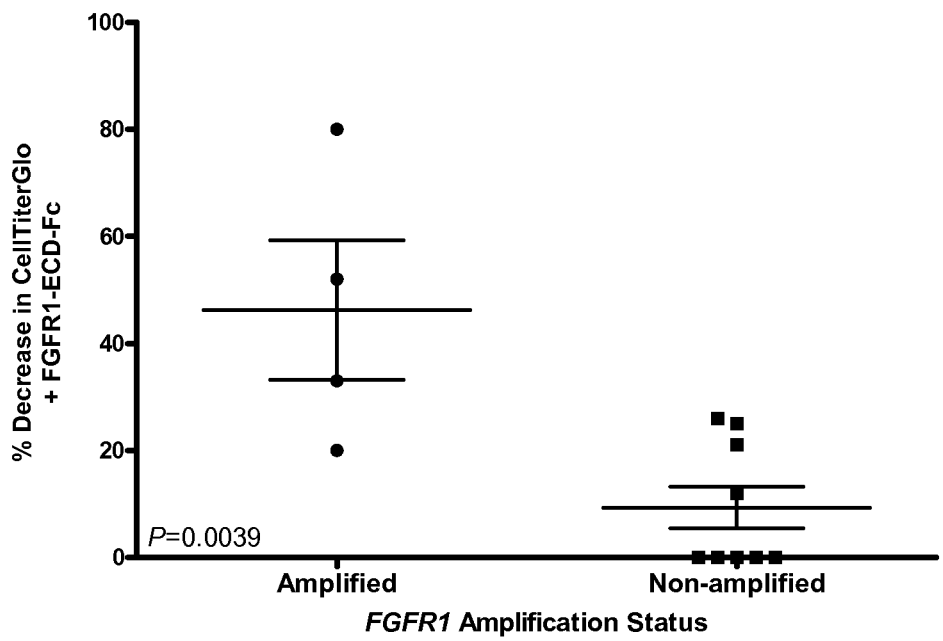
FIG. 3 shows a plot of average % decrease in cell number in various FGFR1 gene amplified lung cancer cell lines and various FGFR1 gene non-amplified lung cancer cell lines grown in the presence of FGFR1-ECD.339-Fc, as described in Example 1.

Percent reduction in CellTiterGlo relative light units (RLU) in the presence of FGFR1-ECD.339-Fc was averaged across all FBS concentrations examined for each of the four FGFR1 gene-amplified lung cancer cell lines and was compared to a panel of lung cancer cell lines without FGFR1 gene amplification (FIG. 3). Lung cancer cell lines without FGFR1 gene amplification examined in this experiment included NCI-H838, NCI-H1793, A549, Calu-1, NCI-H226, NCI-H441, NCI-H460, NCI-H522 and NCI-H2126. Non-amplified cell lines were purchased from ATTC (Manassas, Va.) and cultured according to supplier instructions. Lung cancer cell lines with FGFR1 gene amplification on average had a 46.25% reduction in cell number, as assessed by CellTiterGlo, with the addition of FGFR1-ECD.339-Fc compared to addition of control ECD-Fc. In comparison, lung cancer cell lines without FGFR1 gene amplification displayed on average a 9.33% decrease in cell number, as assessed by CellTiterGlo, on addition of FGFR1-ECD.339-Fc compared to addition of control ECD-Fc. This difference between the impact on cell number of FGFR1-ECD.339-Fc on FGFR1 gene amplified and non-amplified lung cancer cell lines was statistically significant (P=0.0039).

Figure 4:
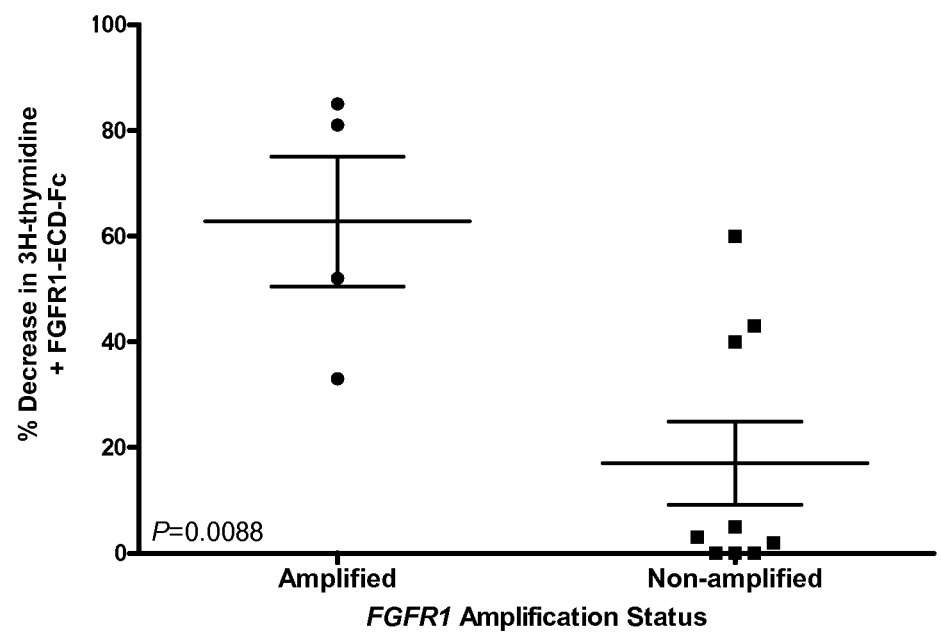
FIG. 4 shows a plot of average % reduction in 3H-thymidine incorporation in various FGFR1 gene amplified lung cancer cell lines and various FGFR1 gene non-amplified lung cancer cell lines grown in the presence of FGFR1-ECD.339-Fc, as described in Example 1.

The impact of FGFR1-ECD.339-Fc on cell proliferation as assessed by tritiated thymidine incorporation was also compared between FGFR1 gene amplified and non-amplified lung cancer cell lines (FIG. 4). An average percent reduction in cell proliferation with FGFR1-ECD.339-Fc addition was determined across all FBS concentrations examined for each FGFR1 gene amplified cell line and the panel of non-FGFR1 gene amplified cell lines indicated above. Lung cancer cell lines with FGFR1 gene amplification on average had a 62.75% reduction in CPM with the addition of FGFR1-ECD.339-Fc compared to addition of control ECD-Fc. In comparison, lung cancer cell lines without FGFR1 gene amplification displayed on average a 17.0% decrease in CPM, on addition of FGFR1-ECD.339-Fc compared to addition of control ECD-Fc. This difference between FGFR1 gene amplified and non-amplified lung cancer cell lines was statistically significant (P=0.0088).

Example 2: Administration of FGFR1-ECD.339-Fc Inhibits Tumor Growth in the DMS53 Small Cell Lung Cancer (SCLC) Xenograft Model Six week old female SCID mice were purchased from Charles River Laboratories (Wilmington, Mass.) and were acclimated for 1 week before the start of the study. Human small cell lung cancer (SCLC) cell line DMS53 was used as the tumor model and was purchased from ATCC (Manassas, Va.; Cat. No. CRL-2062). The cells were cultured for three passages in Waymouth's MB 752/1 medium+10% FBS+2 mM L-glutamine at 37° C. in a humidified atmosphere with 5% $CO_2$. When the cultured cells reached 85-90% confluence, cells were harvested and resuspended in cold $Ca^{2+}$ and $Mg^{2+}$ free phosphate buffered saline (PBS) containing 50% Matrigel at $5\times10^7$ cells per milliliter. The cells were implanted subcutaneously over the right flank of the mice at $5\times10^6$ cells/100 µl/mouse. One day following cell implantation mice were sorted and randomized (n=10) and treatment initiated according to Table 3, below.

FGFR1-ECD.339-Fc was formulated in PBS at 3 mg/ml and administered intraperitoneally (i.p.) at 15 mg/kg (300 µg/100 µl/mouse) twice a week for four weeks. Human albumin was purchased from Grifols USA (Los Angeles, Calif.; Cat. No. NDC 61953-0002-1), diluted to a working stock (3 mg/ml) with 0.9% sodium chloride, and was used as negative control at 300 µg/100 µl/mouse (15 mg/kg) administered twice a week for four weeks.

TABLE 3

Dosing groups

| Group | Number of Animals | Test Article and Dose (mg test article per weight mouse) | Dosing Route and Schedule |
|---|---|---|---|
| 1 | 10 | Albumin | Intraperitoneal, 2X/week |
| 2 | 10 | FGFR1-ECD.339-Fc, 5 mg/kg | Intraperitoneal, 2X/week |

Tumor sizes were measured in each mouse on days 7, 14, 21, 28, 35 and 39 following the day of tumor cell inoculation. The length and width of each tumor was measured using calipers and the tumor size calculated according to the formula:

Tumor size $(mm^3)$=(width (mm)×length $(mm))^2/2$

Mice were euthanized as a "cancer death" when the subcutaneous tumor volumes exceeded 2000 $mm^3$ or when the tumors became excessively necrotic.

Figure 5:
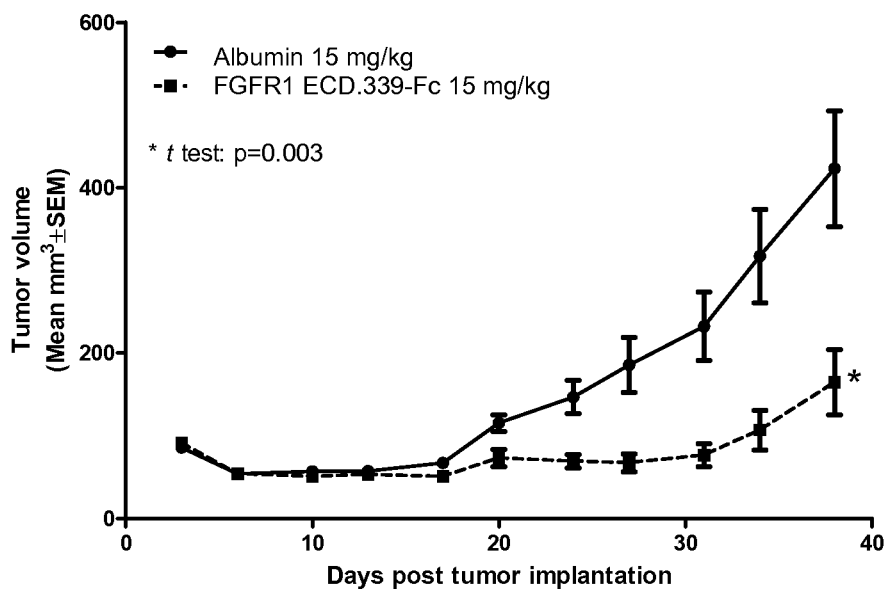
FIG. 5 shows mean tumor volume at various time points in mice implanted with DMS53 cells and treated with FGFR1-ECD.339-Fc or albumin, as described in Example 2.

FIG. 5 shows the results of this experiment. Mice that received FGFR1-ECD.339-Fc showed a 64% reduction of tumor growth compared to albumin-treated animals. Comparison of DMS 53 tumor volume at day 37 in the FGFR1-ECD.339-Fc treatment group and vehicle treated group indicated that this result was statistically significant (P=0.003). P-values were calculated using an ANOVA analysis. See, e.g., *Mathematical Statistics and Data Analysis,* 1988, Wadsworth & Brooks, Pacific Grove, Calif. This analysis demonstrated that FGFR1-ECD.339-Fc significantly reduced tumor growth in the lung cancer cell line DMS53, which has amplification of the gene encoding the FGFR1 receptor.

Example 3: Administration of FGFR1-ECD.339-Fc Inhibits Tumor Growth in the DMS114 Small Cell Lung Cancer (SCLC) Xenograft Model Six week old female SCID mice were purchased from Charles River Laboratories (Wilmington, Mass.) and were acclimated for 1 week before the start of the study. Human small cell lung cancer (SCLC) cell line DMS114 was used as the tumor model and was purchased from ATCC (Manassas, Va.; Cat. No. CRL-2066). The cells were cultured for three passages in Waymouth's MB 752/1 medium+10% FBS+2 mM L-glutamine at 37° C. in a humidified atmosphere with 5% $CO_2$. When the cultured cells reached 85-90% confluence, cells were harvested and resuspended in cold $Ca^{2+}$ and $Mg^{2+}$ free phosphate buffered saline (PBS) containing 50% Matrigel at $5\times10^7$ cells per milliliter. The cells were implanted subcutaneously over the right flank of the mice at $5\times10^6$ cells/100 µl/mouse. One day following cell implantation mice were sorted and randomized (n=10) and treatment initiated as described in Example 2, above.

Tumor sizes were measured in each mouse on days 3, 10, 16, 19, 24, 27, and 31 following the day of tumor cell inoculation. The length and width of each tumor was measured using calipers and the tumor size calculated according to the formula:

Tumor size $(mm^3)$=(width (mm)×length $(mm))^2/2$

Mice were euthanized as a "cancer death" when the subcutaneous tumor volumes exceeded 2000 $mm^3$ or when the tumors became excessively necrotic.

Figure 6:
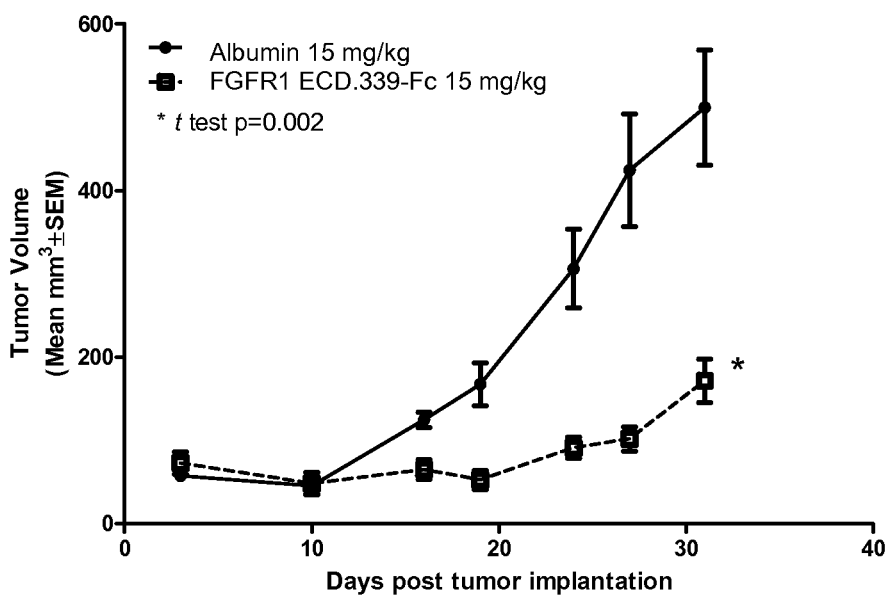
FIG. 6 shows mean tumor volume at various time points in mice implanted with DMS114 cells and treated with FGFR1-ECD.339-Fc or albumin, as described in Example 3.

FIG. 6 shows the results of this experiment. Mice that received FGFR1-ECD.339-Fc showed a 64% reduction of tumor growth compared to albumin-treated animals. Comparison of DMS 114 tumor volume at day 31 in the FGFR1-ECD.339-Fc treatment group and vehicle treated group indicated that this result was statistically significant (P=0.002). P-values were calculated using an ANOVA analysis. See, e.g., *Mathematical Statistics and Data Analysis,* 1988, Wadsworth & Brooks, Pacific Grove, Calif. This analysis demonstrated that FGFR1-ECD.339-Fc significantly reduced tumor growth in the lung cancer cell line DMS114, which has amplification of the gene encoding the FGFR1 receptor.

Example 4: Administration of FGFR1-ECD.339-Fc Inhibits Tumor Growth in the NCI-H1581 Non-Small Cell Lung Cancer (NSCLC) Xenograft Model Six week old female SCID mice were purchased from Charles River Laboratories (Wilmington, Mass.) and were acclimated for 1 week before the start of the study. Human non-small cell lung cancer (NSCLC) cell line NCI-H1581 was used as the tumor model and was purchased from ATCC (Manassas, Va.; Cat. No. CRL-5878). The cells were cultured for three passages in ACL-4 medium (serum-free). The base medium for this cell line is DMEM: F12 (50/50 mix) with the following components to the base medium: 0.02 mg/ml insulin, 0.01 mg/ml transferrin, 25 nM sodium selenite (final conc.), 50 nM Hydrocortisone (final conc.), 1 ng/ml Epidermal Growth Factor (final conc.), 0.01 mM ethanolamine (final conc.), 0.01 mM phosphorylethanolamine (final conc.), 100 pM triiodothyronine (final conc.), 0.5% (w/v) bovine serum albumin (final conc.), 0.5 mM sodium pyruvate (final conc.) and 4.5 mM L-glutamine. Cells were grown at 37° C. in a humidified atmosphere with 5% $CO_2$. When the cultured cells reached 85-90% confluence, cells were harvested and resuspended in cold $Ca^{2+}$ and $Mg^{2+}$ free phosphate buffered saline (PBS) containing 50% Matrigel at $5\times10^7$ cells per milliliter. The cells were implanted subcutaneously over the right flank of the mice at $5\times10^6$ cells/100 μl/mouse. One day following cell implantation mice were sorted and randomized (n=10) and treatment initiated as described in Example 2, above.

Tumor sizes were measured in each mouse on days 7, 10, 14, 17, 21, 25 and 31 following the day of tumor cell inoculation. The length and width of each tumor was measured using calipers and the tumor size calculated according to the formula:

Tumor size $(mm^3)$=(width (mm)×length $(mm))^2/2$

Mice were euthanized as a "cancer death" when the subcutaneous tumor volumes exceeded 2000 $mm^3$ or when the tumors became excessively necrotic.

Figure 7:
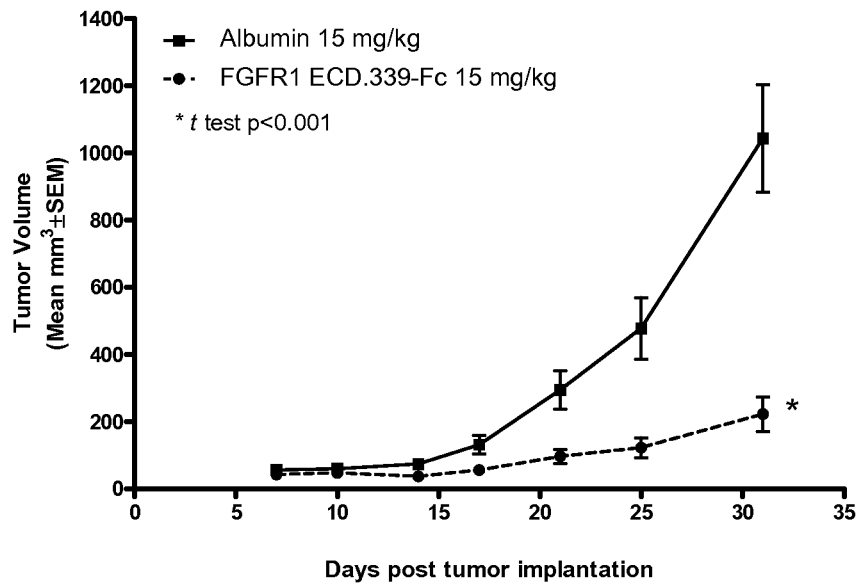
FIG. 7 shows mean tumor volume at various time points in mice implanted with NCI-H1581 cells and treated with FGFR1-ECD.339-Fc or albumin, as described in Example 4.

FIG. 7 shows the results of this experiment. Mice that received FGFR1-ECD.339-Fc showed a 74% reduction of tumor growth compared to albumin-treated animals. Comparison of NCI-H1581 tumor volume at day 31 in the FGFR1-ECD.339-Fc treatment group and vehicle treated group indicated that this result was statistically significant (P<0.001). P-values were calculated using an ANOVA analysis. See, e.g., *Mathematical Statistics and Data Analysis,* 1988, Wadsworth & Brooks, Pacific Grove, Calif. This analysis demonstrated that FGFR1-ECD.339-Fc significantly reduced tumor growth in the lung cancer cell line NCI-H1581, which has amplification of the gene encoding the FGFR1 receptor.

Example 5: Administration of FGFR1-ECD.339-Fc Inhibits Tumor Growth in the NCI-H520 Non-Small Cell Lung Cancer (NSCLC) Xenograft Model Six week old female SCID mice were purchased from Charles River Laboratories (Wilmington, Mass.) and were acclimated for 1 week before the start of the study. Human non-small cell lung cancer (NSCLC) cell line NCI-H520 was used as the tumor model and was purchased from ATCC (Manassas, Va.; Cat. No. HTB-182). The cells were cultured for three passages in RPMI-1640 Medium+10% FBS+2 mM L-glutamine at 37° C. in a humidified atmosphere with 5% $CO_2$. When the cultured cells reached 85-90% confluence, cells were harvested and resuspended in cold $Ca^{2+}$ and $Mg^{2+}$ free phosphate buffered saline (PBS) containing 50% Matrigel at $5\times10^7$ cells per milliliter. The cells were implanted subcutaneously over the right flank of the mice at $5\times10^6$ cells/100 μl/mouse. One day following cell implantation mice were sorted and randomized (n=10) and treatment initiated as described below.

FGFR1-ECD.339-Fc was formulated in PBS at 3 mg/ml and administered intraperitoneally (i.p.) at 20 mg/kg (400 μg/125 μl/mouse) twice a week for four weeks. Human albumin was purchased from Grifols USA (Los Angeles, Calif.; Cat. No. NDC 61953-0002-1), diluted to a working stock (3 mg/ml) with 0.9% sodium chloride, and was used as negative control at 400 μg/125 μl/mouse (20 mg/kg) administered twice a week for six weeks.

Tumor sizes were measured in each mouse on days 11, 18, 25, 32, 39 and 46 following the day of tumor cell inoculation. The length and width of each tumor was measured using calipers and the tumor size calculated according to the formula:

Tumor size $(mm^3)$=(width (mm)×length $(mm))^2/2$

Mice were euthanized as a "cancer death" when the subcutaneous tumor volumes exceeded 2000 $mm^3$ or when the tumors became excessively necrotic.

Figure 8:
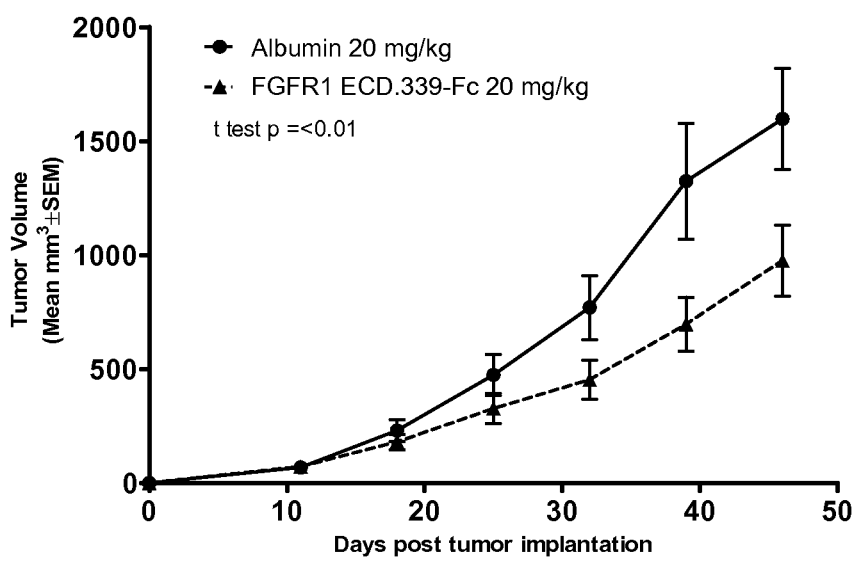
FIG. 8 shows mean tumor volume at various time points in mice implanted with NCI-H520 cells and treated with FGFR1-ECD.339-Fc or albumin, as described in Example 5.

FIG. 8 shows the results of this experiment. Mice that received FGFR1-ECD.339-Fc showed a 47% reduction of tumor growth compared to albumin-treated animals. Comparison of NCI-H520 tumor volume at day 46 in the FGFR1-ECD.339-Fc treatment group and vehicle treated group indicated that this result was statistically significant (P<0.01). P-values were calculated using an ANOVA analysis. See, e.g., *Mathematical Statistics and Data Analysis,* 1988, Wadsworth & Brooks, Pacific Grove, Calif. This analysis demonstrated that FGFR1-ECD.339-Fc significantly reduced tumor growth in the lung cancer cell line NCI-H520, which has amplification of the gene encoding the FGFR1 receptor.

Efficacy of FGFR1-ECD.339-Fc treatment in one additional xenograft model, using non-small cell lung cancer (NSCLC) cell line NCI-H1703, was tested in a similar manner as the SCLC and NSCLC cell lines described above. Mice that received FGFR1-ECD.339-Fc showed a 31% reduction of tumor growth compared to albumin-treated animals. It is noted that NCI-H1703 cell line contains a drug-sensitive PDGFRA/PDGFC genomic amplification in addition to FGFR1 amplification, which may be responsible for the modest efficacy observed.

Example 6: Certain Lung Cancer Xenograft Models with FGFR1 Gene Amplification were More Sensitive to FGFR1-ECD.339-Fc-Mediated Growth Inhibition than Certain Non-FGFR1 Gene Amplified Lung Cancer Xenograft Models The impact of FGFR1-ECD.339-Fc on tumor growth was compared between FGFR1 gene amplified and non-amplified lung cancer xenograft models. Lung cell lines without FGFR1-amplification examined in this experiment were as follows: A549, NCI-H460, NCI-H226, NCI-H2126, NCI-H441, NCI-H358, NCI-H522 and Colo699. Non-amplified cell lines were purchased from ATTC (Manassas, Va.) and cultured according to supplier instructions. Lung cancer xenograft models using non-FGFR1 gene amplified cell lines were carried out substantially as described in Example 2.

A panel of patient-derived xenograft (PDX) models of lung cancer without FGFR1-amplification was also examined for sensitivity to FGFR1-ECD.339-Fc. PDX xenografts have been transplanted directly from cancer patients into nude mice without in vitro tissue culture. The tumor xenografts retain most of the characteristics of the parental patient tumors including histology and sensitivity to anti-cancer drugs. Lung PDX models examined were as follows: PDX D35087, PDX D37638, PDX D35376, LXFL-430, LXFE-937, LXFE-397, LXFA-737 and LXFA-629. Preliminary pathology and patient characteristics for the lung PDXs examined are outlined in Table 4.

TABLE 4

Characteristics of lung cancer patient-derived xenograph (PDX) models

| Tumor No. | Tissue type | Origin | Differentiation | Patient age | Gender | Stage |
|---|---|---|---|---|---|---|
| LXFE_937 | Squamous | Lung | moderately differentiated | 37 | female | T3N1M0 |
| LXFE_397 | Squamous | Lung | poorly differentiated | 56 | male | T1N0Mx |
| LXFL_430 | Large cell | Lung | poorly differentiated | 53 | male | T2N1M0 |
| LXFA_629 | Adeno | Lung | poorly differentiated | 59 | male | T3N2Mx |
| LXFA_737 | Adeno | Lung | moderately differentiated | 56 | male | T3N2Mx |
| PDX D35087 | Squamous | Lung | moderately differentiated | — | — | T3N0M0 |
| PDX D37638 | Squamous | Lung | poorly differentiated | — | — | T3N2M0 |
| PDX D35376 | Squamous | Lung | moderately differentiated | — | — | T2N0M0 |

Six week old female SCID mice were purchased from Charles River Laboratories (Wilmington, Mass.) and were acclimated for 1 week before the start of the study. PDX tumor fragments were obtained from xenografts in serial passage in donor SCID mice. After removal of tumors from donor mice, they were cut into fragments (1-2 mm diameter, ~25 mgs) and placed in RPMI 1640 culture medium until subcutaneous implantation. Recipient mice were anaesthetized by inhalation of isoflurane. A small pocket was formed with blunt forceps and one chunk of tumor PDX was placed in the pocket. The wound was sealed using dermabond glue and a drop of bupivicaine placed on the incision. One day following PDX implantation mice were sorted and randomized (n=10) and treatment initiated as described below.

FGFR1-ECD.339-Fc was formulated in PBS at 3 mg/ml and administered intraperitoneally (i.p.) at 15 mg/kg (300 µg/100 µl/mouse) twice a week for four to eight weeks depending on the growth rate of the PDX tumor implanted. Human albumin was purchased from Grifols USA (Los Angeles, Calif.; Cat. No. NDC 61953-0002-1), diluted to a working stock (3 mg/ml) with 0.9% sodium chloride, and was used as negative control at 300 ng/100 µl/mouse (15 mg/kg) administered twice a week for four to eight weeks depending on the growth rate of the PDX tumor implanted.

Tumor sizes were measured in each mouse on days 11, 18, 25, 32, 39 and 46 following the day of tumor cell inoculation. The length and width of each tumor was measured using calipers and the tumor size calculated according to the formula:

$$\text{Tumor size (mm}^3\text{)} = (\text{width (mm)} \times \text{length (mm)})^2/2$$

Mice were euthanized as a "cancer death" when the subcutaneous tumor volumes exceeded 2000 mm$^3$ or when the tumors became excessively necrotic.

Figure 9:
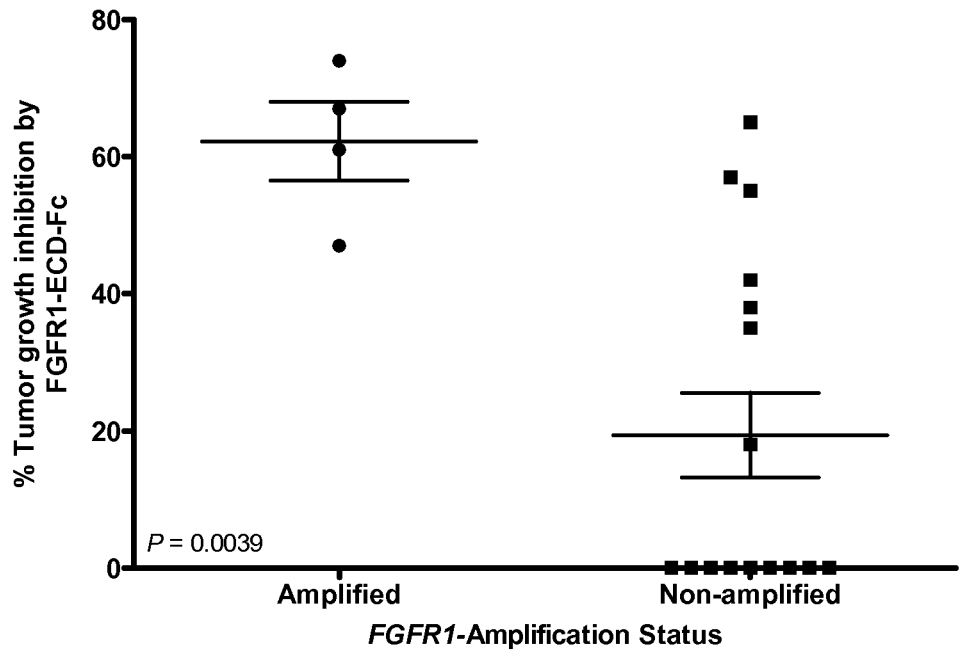
FIG. 9 shows % tumor growth inhibition by FGFR1-ECD.339-Fc in mouse xenografts of tumor cells having FGFR1 gene amplification and tumor cells having a non-amplified FGFR1 gene, as described in Example 6.

Percentage tumor growth inhibition by FGFR1-ECD.339-Fc was determined by area-under-the-curve (AUC) analysis of xenograft growth curves treated with FGFR1-ECD.339-Fc compared to albumin control. FIG. 9 shows a scatterplot of the results of this analysis. Lung cancer xenografts with FGFR1 gene amplification had an average a 56% reduction in tumor growth with FGFR1-ECD.339-Fc treatment. In comparison, lung cancer xenografts without FGFR1 gene amplification displayed an average 22% decrease in xenograft growth with FGFR1-ECD.339-Fc treatment compared to control. The difference in FGFR1-ECD.339-Fc-mediated xenograft inhibition between FGFR1 gene amplified and non-amplified lung cancer xenograft models was statistically significant (P=0.0333).

Thus, FGFR1 gene amplified tumor cells were found to be more sensitive to FGFR1-ECD.339-Fc administration than tumor cells with a non-amplified FGFR1 gene.

Example 7: FGFR1 Overexpression in FGFR1 Gene-Amplified and Non-Amplified Lung Cancer Cell Lines and Xenografts The expression of the FGFR1 at the RNA level was compared between FGFR1 gene amplified and non-amplified lung cancer cell lines, xenograft models, and PDX models. Lung cancer cell lines without FGFR1gene amplification examined in this experiment were as follows: A549, NCI-H460, NCI-H226, NCI-H2126, NCI-H441, NCI-H358, NCI-H522, MSTO-211H, and Colo699. Non-amplified cell lines were purchased from ATTC (Manassas, Va.) and cultured according to supplier instructions. A panel of patient-derived xenograft (PDX) models of lung cancer without FGFR1 gene amplification was also examined for FGFR1 mRNA expression. Lung PDX models examined were as follows: PDX D35087, PDX D37638, PDX D35376, LXFL-430, LXFE-937, LXFE-397, LXFA-737, and LXFA-629. Preliminary pathology and patient characteristics for the lung PDXs examined are outlined above in Table 4.

RNA was extracted from cell lines grown in vitro or tumor xenografts grown in vivo using the RNAeasy® mini kit (cat. No. 74104, Qiagen, Germany). Extracted RNA was treated with DNAse I prior to creating cDNA with random hexamer priming and reverse transcriptase using the QuantiTect Reverse Transcription Kit (cat. No. 205311, Qiagen, Germany). Human FGFR1 RNA expression was determined using an FGFR1 QuantiTect Primer Assay (Hs_FGFR1_1_SG, cat. No. QT00102837, Qiagen, Germany) and a human GUSB control reference QuantiTect Primer Assay (Hs_GUSB_1_SG, cat. No. QT00046046, Qiagen, Germany). QuantiTect SYBR Green PCR Kits (cat. No. 204145, Qiagen, Germany) were used to quantify mRNA expression levels using real-time qRT-PCR and an ABI Prism ViiA™ 7 Real-Time PCR System (Applied Biosystems, Foster City, Calif.). Relative gene expression quantification was calculated according to the comparative Ct method using human GUSB as a reference and commercial RNA controls (Stratagene, La Jolla, Calif.). Relative quantification was determined according to the formula: $2^{-(\Delta Ct\ sample - \Delta Ct\ calibrator)}$.

GUSB-normalized FGFR1 RNA expression was compared between lung cancer cell lines (FIG. 10) and xenograft models (FIG. 12) with and without FGFR1 gene amplification.

Figure 10:
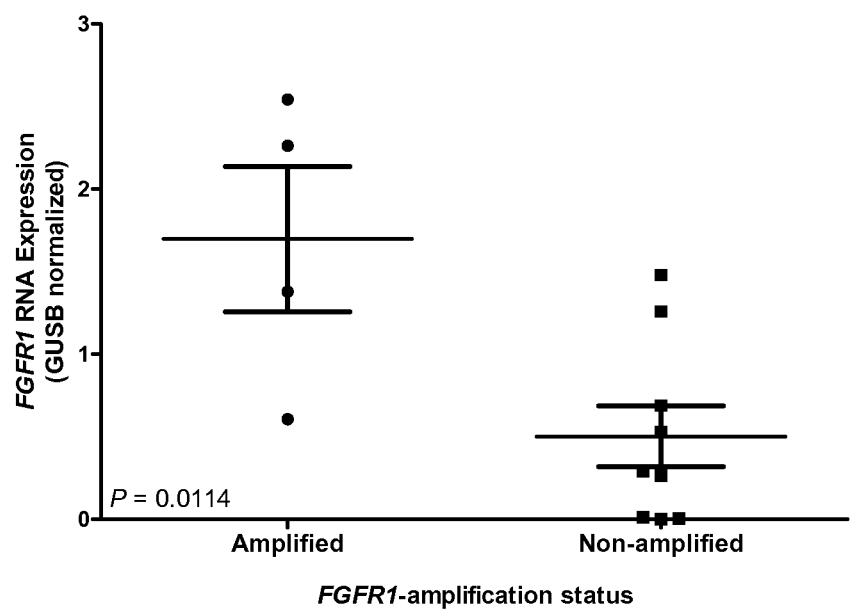
FIG. 10 shows a scatter plot of FGFR1 mRNA expression in lung cancer cell lines with and without FGFR1 gene amplification, as described in Example 7.

FIG. 10 shows a scatterplot of FGFR1 RNA expression in cell lines with and without FGFR1 gene amplification. Lung cancer cell lines with FGFR1gene amplification have a statistically significant increase (P=0.0114) in FGFR1 mRNA expression compared to cell lines without FGFR1 gene amplification. FIG. 10 also demonstrates that a sub-population of lung cancer cell lines have high FGFR1 mRNA expression in the absence of FGFR1 gene amplification. NCI-H226, which has a GUSB normalized gene expression of FGFR1 of 1.48, and NCI-H522, which has a GUSB normalized gene expression of FGFR1 of 1.26, represent the two uppermost outlier points in the non-amplified lung cancer cell line population.

Figure 11:
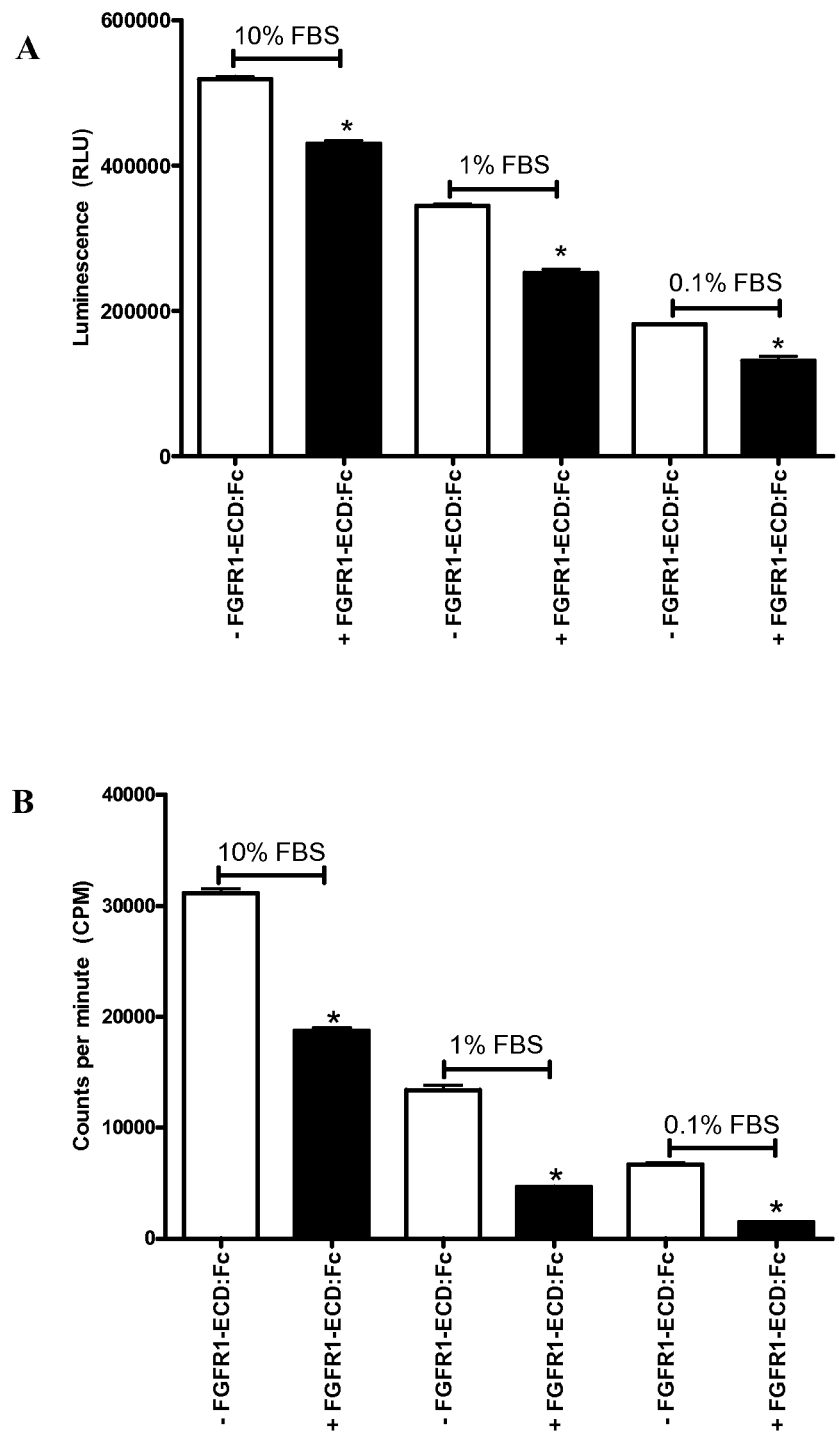
FIG. 11 shows graphs of (A) average luminescence in the CellTiterGlo® assay and (B) counts per minute in the tritiated thymidine incorporation assay carried out on NCI-H226 cells grown with varying amounts of serum and in the presence or absence of FGFR1-ECD.339-Fc, as described in Example 7.

NCI-H226 and NCI-H522 were also sensitive to FGFR1-ECD.339-Fc in vitro, having decreased cell proliferation and number using the tritiated thymidine ([3H]-TdR) incorporation assay and CellTiter-Glo® Luminescent Cell Viability Assay (Promega, Madison, Wis.), respectively. FIG. 11A shows results from the CellTiter-Glo® assay for the NCI-H226 cell line, demonstrating that cell number was significantly (* indicates P=>0.05) reduced by FGFR1-ECD.339-Fc incubation in the NCI-H226 cell line, which does not have FGFR1-amplification. P-values were determined using an unpaired t-test. See, e.g., Mathematical Statistics and Data Analysis, 1988, Wadsworth & Brooks, Pacific Grove, Calif.

FIG. 11B shows results from the tritiated thymidine incorporation assay for the NCI-H226 cell line, demonstrating that cell proliferation was significantly (* indicates P=>0.05) reduced by FGFR1-ECD.339-Fc incubation in the NCI-H226 cell line, which does not have FGFR1 gene amplification. P-values were determined using an unpaired t-test. The control ECD Fc had little no impact on NCI-H226 cell proliferation.

Thus, certain lung cancer cell lines that do not have FGFR1 gene amplification, but which have FGFR1 overexpression, are sensitive to FGFR1-ECD.339-Fc treatment.

Figure 12:
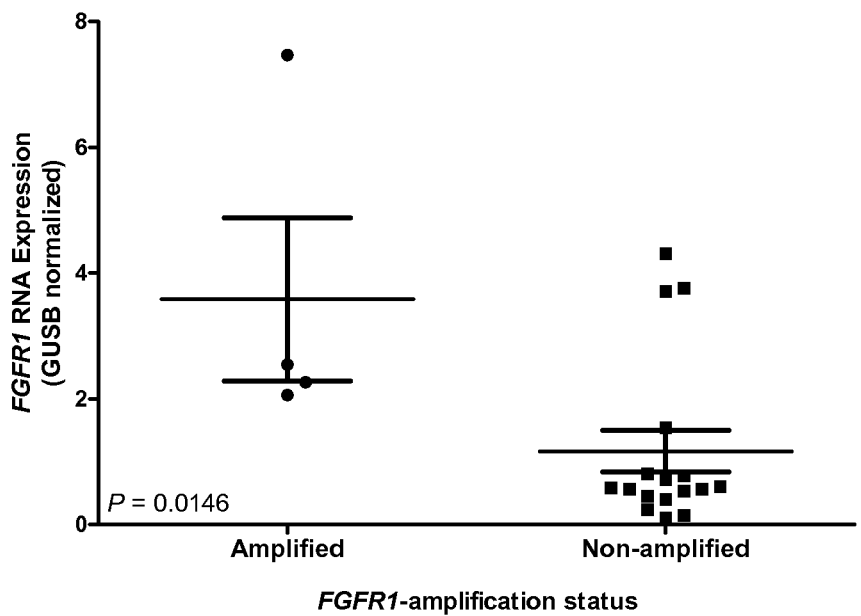
FIG. 12 shows a scatter plot of FGFR1 mRNA expression in lung cancer xenografts with and without FGFR1 gene amplification, as described in Example 7.

FIG. 12 shows a scatterplot of FGFR1 mRNA expression comparing FGFR1 gene amplified to non-amplified lung cancer xenografts. Xenograft models with FGFR1 gene amplification had a statistically significant (P=0.0146) increase in FGFR1 RNA levels compared to non-amplified cell lines. In addition, in agreement with the in vitro data, a sub-population of lung cancer xenograft models has high FGFR1 RNA expression in the absence of FGFR1 gene amplification. Xenograft models NCI-H226, NCI-H522 and PDX D35087 represent the 3 outlier points for FGFR1 RNA expression in the non-amplified lung models (FIG. 12), with GUSB-normalized gene expression levels of 3.70, 3.75 and 4.30, respectively.

NCI-H226, NCI-H522, and PDX D35087 were also sensitive to FGFR1-ECD.339-Fc in vivo, demonstrating a statistically significant (P<0.05) reduction in tumor growth of 55, 42 and 57% respectively with FGFR1-ECD.339-Fc treatment. For PDX D35087, the experiment was carried out substantially as described in Example 6.

Tumor sizes were measured in each mouse on days 26, 35, 41 and 45 following the day of PDX D35087 implantation. The length and width of each tumor was measured using calipers and the tumor size calculated according to the formula:

$$\text{Tumor size (mm}^3) = (\text{width (mm)} \times \text{length (mm)})^2/2$$

Figure 13:
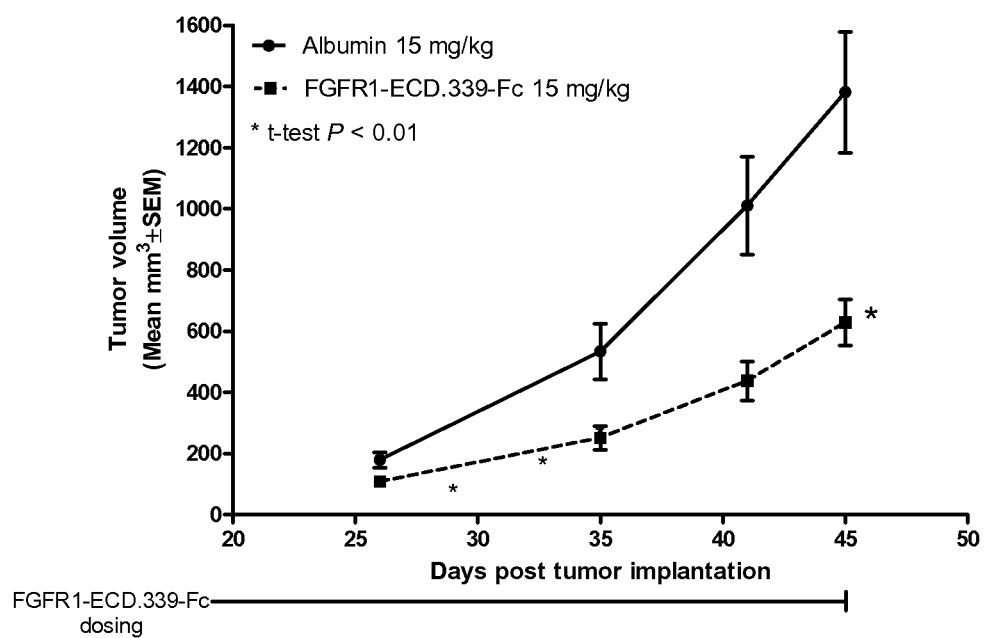
FIG. 13 shows mean tumor volume at various time points in mice implanted with PDX D35087 cells and treated with FGFR1-ECD.339-Fc or albumin, as described in Example 7.

FIG. 13 shows the results of this experiment. Mice that received FGFR1-ECD.339-Fc showed an inhibition of tumor growth compared to albumin-treated animals. Comparison of PDX 35087 tumor volume at day 45 in the FGFR1-ECD.339-Fc treatment group and vehicle treated group indicated that this result was statistically significant (P<0.01). P-values were calculated using an ANOVA analysis. See, e.g., Mathematical Statistics and Data Analysis, 1988, Wadsworth & Brooks, Pacific Grove, Calif. This analysis demonstrated that FGFR1-ECD.339-Fc significantly reduced tumor growth in the PDX lung tumor model D35087, which does not have amplification of the FGFR1 gene, but expresses relatively high-levels of FGFR1 mRNA.

Thus, certain lung cancer xenograft models that do not have FGFR1 gene amplification, but which have FGFR1 overexpression, are sensitive to FGFR1-ECD.339-Fc treatment.

Example 8: Predictors of FGFR1-ECD.339-Fc Response

The RNA expression of a panel of FGFR1-related genes including FGF ligands, FGF receptors, FGF binding proteins, FGF signaling molecules, and a group of angiogenesis-related targets was determined in a set of 35 tumor cell lines and xenografts using qRT-PCR. RNA was extracted from cell lines grown in vitro or tumor xenografts grown in vivo using the RNAeasy® mini kit (Qiagen, Germany). Extracted RNA was treated with DNAse I prior to creating cDNA with random hexamer priming and reverse transcriptase using the QuantiTect Reverse Transcription Kit (Qiagen, Germany). Human and mouse RNA expression was determined using QuantiTect Primer Assays (Qiagen, Germany) employing a human GUSB control reference QuantiTect Primer Assay (Qiagen, Germany). QuantiTect SYBR Green PCR Kits (Qiagen, Germany) were used to quantify mRNA expression levels using real-time qRT-PCR and an ABI Prism ViiA™ 7 Real-Time PCR System (Applied Biosystems, Foster City, Calif.). Relative gene expression quantification was calculated according to the comparative Ct method using human GUSB as a reference and commercial RNA controls (Stratagene, La Jolla, Calif.). Relative quantification was determined according to the formula: $2^{-(\Delta Ct\ sample - \Delta Ct\ calibrator)}$.

The tumor cell lines and xenografts used in this experiment are shown in Table 5. Also shown in Table 5 are the dosing schedule for FGFR1-ECD.339-Fc in a mouse xenograft model, the percent tumor growth inhibition (TGI (%)) and the statistical significance of the tumor growth inhibition (P Value), as well as whether the FGFR1 gene is amplified in the cell line.

TABLE 5

Anti-tumor activity of FGFR1-ECD.339-Fc in a panel of xenograft models

| Tumor type | Xenograft model | Cell line/ PDX | Dosing route | Dose | Dose sched. | TGI (%) | P Value | FGFR1 amp. status |
|---|---|---|---|---|---|---|---|---|
| Colon | HCT116 | Cell Line | IP | 15 mg/kg | BIW | 0% | ns | Non-amplified |
|  | Colo205 | Cell Line | IV | 5 mg/kg | BIW | 38% | P < 0.001 | Non-amplified |
|  | Colo201 | Cell Line | IP | 15 mg/kg | BIW | 0% | ns | Non-amplified |
| Renal | G-401 | Cell Line | IP | 15 mg/kg | BIW | 36% | P < 0.05 | Non-amplified |
|  | A498 | Cell Line | IP | 15 mg/kg | BIW | 7% | ns | Non-amplified |
|  | Caki-1 | Cell Line | IV | 10 mg/kg | BIW | 81% | P < 0.001 | Non-amplified |
| Lung | A549 | Cell Line | IP | 10 mg/kg | BIW | 38% | P < 0.05 | Non-amplified |
|  | NCI-H460 | Cell Line | IP | 10 mg/kg | BIW | 35% | P < 0.05 | Non-amplified |
|  | NCI-H226 | Cell Line | IP | 15 mg/kg | 3×/w | 55% | P < 0.001 | Non-amplified |
|  | NCI-H520 | Cell Line | IP | 20 mg/kg | BIW | 47% | P < 0.05 | Amplified |
|  | NCI-H1703 | Cell Line | IP | 15 mg/kg | BIW | 31% | P < 0.05 | Amplified |
|  | NCI-H2126 | Cell Line | IP | 15 mg/kg | BIW | 0% | ns | Non-amplified |
|  | NCI-H441 | Cell Line | IP | 15 mg/kg | BIW | 0% | ns | Non-amplified |
|  | NCI-H358 | Cell Line | IP | 15 mg/kg | BIW | 0% | ns | Non-amplified |
|  | NCI-H522 | Cell Line | IP | 10 mg/kg | BIW | 42% | P < 0.05 | Non-amplified |
|  | NCI-H1581 | Cell Line | IP | 15 mg/kg | BIW | 74% | P = 0.002 | Amplified |
|  | DMS53 | Cell Line | IP | 15 mg/kg | BIW | 64% | 0.003 | Amplified |
|  | DMS114 | Cell Line | IP | 15 mg/kg | BIW | 64% | P < 0.001 | Amplified |
|  | Calu-1 | Cell Line | IP | 15 mg/kg | BIW | 0% | ns | Non-amplified |
|  | D35087 | PDX | IP | 15 mg/kg | BIW | 57% | P < 0.01 | Non-amplified |
|  | D37638 | PDX | IP | 15 mg/kg | BIW | 0% | ns | Non-amplified |
|  | D35376 | PDX | IP | 15 mg/kg | BIW | 0% | ns | Non-amplified |
|  | LXFA-737 | PDX | IP | 15 mg/kg | BIW | 0% | ns | Non-amplified |
|  | LXFA-629 | PDX | IP | 15 mg/kg | BIW | 65% | P = 0.007 | Non-amplified |
| Mesothelioma | MSTO-211H | Cell Line | IP | 15 mg/kg | BIW | 64% | P < 0.0001 | Non-amplified |
| Glioblastoma | U-87 | Cell Line | IP | 15 mg/kg | BIW | 0% | ns | Non-amplified |
|  | U-118 | Cell Line | IP | 15 mg/kg | BIW | 36% | ns | Non-amplified |
|  | U-251 | Cell Line | IP | 15 mg/kg | BIW | 48% | P = 0.0078 | Non-amplified |
| Retinoblastoma | Y79 | Cell Line | IP | 10 mg/kg | BIW | 0% | ns | Non-amplified |
| Prostate | Du145 | Cell Line | IP | 0.15 mg/kg | 3×/w | 31% | ns | Non-amplified |
| Endometrial | MFE-280 | Cell Line | IP | 15 mg/kg | BIW | 96% | P < 0.001 | Non-amplified |
|  | HEC-1B | Cell Line | IP | 15 mg/kg | BIW | 30% | P < 0.05 | Non-amplified |
|  | MFE-319 | Cell Line | IP | 15 mg/kg | BIW | 0% | ns | Non-amplified |
| Breast | MDA-MB-231 | Cell Line | IP | 15 mg/kg | BIW | 0% | ns | Non-amplified |
|  | JIMT1 | Cell Line | IP | 1 mg/kg | BIW | 28% | P < 0.05 | Non-amplified |

Figure 16:
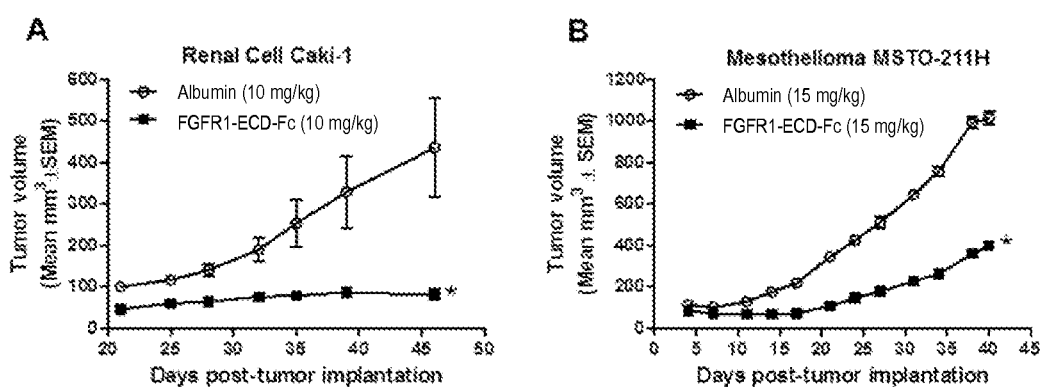
FIG. 16 shows anti-tumor activity of FGFR1-ECD.339-Fc in (A) a Caki-1 renal cell carcinoma xenograft model, and (B) a MSTO-211H mesothelioma xenograft model, as described in Example 8.

An exemplary xenograft experiment is as follows. For Caki-1 and MSTO-211H, five million cells were implanted subcutaneously over the right flank of SCID mice (N=10 per group). FGFR1-ECD.339-Fc or albumin was administered i.p. twice a week at the dose indicated in Table 5. FIG. 16 shows anti-tumor activity of FGFR1-ECD.339-Fc in selected xenograft models. Representative tumor growth curves are shown for a renal cancer, Caki-1, (A), and mesothelioma, MSTO-211H, (B) xenograft cancer model. In the renal cell carcinoma (RCC) Caki-1 model, administration of FGFR1-ECD.339-Fc at 10 mg/kg twice a week for 6 weeks resulted in 81% (P<0.001) tumor growth inhibition (TGI; FIG. 16a). In the MSTO-211H mesothelioma model, FGFR1-ECD.339-Fc administration reduced tumor growth (FIG. 16b) by 64% (P<0.0001). In responding tumors, FGFR1-ECD.339-Fc significantly reduced tumor volume as assessed by area-under-the-curve (AUC) analysis. Responses were observed in 19/35 (54%) of the models examined, with a range of 25-96% inhibition (see Table 5).

In order to further understand the potential molecular determinants that make xenograft models sensitive to treatment with FGFR1-ECD.339-Fc, the RNA expression of a panel of genes including FGF ligands, FGF receptors, FGF binding proteins and FGF signaling molecules was examined using qRT-PCR in certain xenograft models from Table 5. The results are shown in Table 7, below.

Gene expression was then correlated to FGFR1-ECD.339-Fc response to determine RNA expression signatures positively and negatively correlated with anti-tumor activity. Table 8 shows the results of that analysis. In addition to FGF2, RNA expression of FGF18 (P=0.02227) was also positively (6.9-fold) correlated with FGFR1-ECD.339-Fc anti-tumor activity. The downstream target gene of FGF signaling, ets variant 4 (ETV4), was the most significant (P=0.01639) gene for its positive (2.897-fold) association with FGFR1-ECD.339-Fc activity. Expression of FGFR1 (P=0.01276), including the FGFR1IIIc splice variant (P=0.01603), was a positive predictor for FGFR1-ECD.339-Fc response. Expression of the FGFR1IIIb splice variant was not correlated with FGFR1-ECD.339-Fc response in that experiment. In addition to FGFR1, expression of the FGFR3IIIc receptor (P=0.02488) was also positively correlated with FGFR1-ECD.339-Fc response, reflecting the potential overlap in FGF-ligand binding affinities between the Inc-splice isoforms of FGFR1 and FGFR3 receptors. Significant genes with a negative association with FGFR1-ECD.339-Fc activity were not found in this analysis.

TABLE 8

Statistical analysis of FGF-related gene expression in relation to FGFR1-ECD.339-Fc anti-tumor response in xenograft models

| Gene | Ratio§ | P value† |
|---|---|---|
| ETV4 | 2.897 | 0.01639 |
| FGFR1 | 2.447 | 0.01669 |
| FGFR3IIIc | 9.863 | 0.01944 |
| FGF18 | 6.915 | 0.02227 |
| FGF2 | 247.7 | 0.03569 |
| FGFR1IIIc | 3.647 | 0.0431 |
| DUSP4 | 0.09578 | 0.08166 |
| TNC | 0.0345 | 0.1212 |
| VIM | 5.155 | 0.1448 |
| ETV5 | 1.447 | 0.1567 |
| FGFBP3 | 1.84 | 0.1592 |
| PLAU | 0.3842 | 0.1781 |
| PLAUR | 0.3805 | 0.2408 |
| FGF7 | 1.991 | 0.243 |

TABLE 8-continued

Statistical analysis of FGF-related gene expression in relation to FGFR1-ECD.339-Fc anti-tumor response in xenograft models

| Gene | Ratio§ | P value† |
|---|---|---|
| FGF5 | 24.79 | 0.2691 |
| KDR | 0.5892 | 0.2742 |
| FGF11 | 2.153 | 0.2944 |
| MET | 0.4225 | 0.2962 |
| FGF2 | 5.48 | 0.3015 |
| DUSP5 | 0.4765 | 0.3238 |
| FGF22 | 1.604 | 0.3484 |
| FGF10 | 1.91 | 0.3518 |
| FGFR2 | 1.402 | 0.3587 |
| FGF1 | 0.09845 | 0.398 |
| FGFR2IIIc | 5.546 | 0.4195 |
| FGF17 | 1.334 | 0.4361 |
| FGFR3IIIb | 1.08 | 0.451 |
| FGF20 | 5.967 | 0.4729 |
| FGFR1IIIb | 0.6493 | 0.486 |
| SPRY3 | 1.665 | 0.4944 |
| SPRY1 | 1.394 | 0.5008 |
| DUSP6 | 0.6418 | 0.507 |
| FGF19 | 1.203 | 0.5338 |
| FLRT1 | 1.158 | 0.5676 |
| FGF3 | 1.431 | 0.5699 |
| FGFR4 | 1.347 | 0.5755 |
| FGF9 | 0.5356 | 0.6102 |
| FGFR3 | 1.767 | 0.6165 |
| SPRY2 | 0.3142 | 0.6313 |
| SERPINE1 | 0.333 | 0.6642 |
| FGF21 | 1.935 | 0.6744 |
| FLRT2 | 0.2276 | 0.693 |
| FGFR2b | 0.9266 | 0.7897 |
| FGF6 | 0 | 0.8316 |
| FGFBP1 | 0.5 | 0.8372 |
| SOX9 | 1.181 | 0.8372 |
| SPRY4 | 0.9028 | 0.8372 |
| NCAM1 | 1.661 | 0.8731 |
| FGF8 | 1.052 | 0.9552 |
| ELK4 | 1.062 | 0.9815 |
| CDH1 | 0.1158 | 0.9818 |
| ELK3 | 1.157 | 0.9818 |
| FGFBP2 | 0.7737 | 0.9818 |
| FGF16 | 1.076 | 1 |
| FLRT3 | 0.7523 | 1 |

§Gene expression ratio determined by median gene expression in FGFR1-ECD.339-Fc responders/non-responders
†P-values are determined by a Mann-Whitney test of PCR gene expression in responders vs. non-responders for each gene using all models in Table 5.

To determine what RNA factors may determine lung xenograft response in the absence of FGFR1-gene amplification, the correlation of FGFR1-ECD.339-Fc response in the non-FGFR1 amplified subset of lung models was examined (N=13). The results of that analysis are shown in Table 9. FGF2 expression was up-regulated>3,000 fold in responding vs. non-responding FGFR1 non-amplified lung models (P=0.029). The expression of FGFR1IIIc and FGFR3IIIc also displayed a positive trend with FGFR1-ECD.339-Fc response in the non-FGFR1 amplified lung subset in this experiment.

TABLE 9

Statistical analysis of FGF-related gene expression in relation to FGFR1-ECD.339-Fc anti-tumor response in non-FGFR1 amplified lung xenograft models

| Gene | Ratio§ | P value† |
|---|---|---|
| FGF2 | 3437 | 0.02857 |
| SPRY2 | 0.1395 | 0.05714 |
| FGFR3IIIc | 3.765 | 0.1375 |
| DUSP5 | 0.3241 | 0.2 |
| FGFR1IIIc | 3.688 | 0.2343 |
| FGF21 | 6.868 | 0.2454 |

TABLE 9-continued

Statistical analysis of FGF-related gene expression in
relation to FGFR1-ECD.339-Fc anti-tumor response in
non-FGFR1 amplified lung xenograft models

| Gene | Ratio[§] | P value[†] |
|---|---|---|
| FGFR2 | 8.793 | 0.2949 |
| FGFR1 | 3.72 | 0.2949 |
| FGF19 | 20.79 | 0.3094 |
| FGFR1IIIb | 0.553 | 0.3429 |
| ELK3 | 0.5091 | 0.3429 |
| SPRY4 | 0.3532 | 0.3429 |
| FGFBP1 | 0.1836 | 0.3429 |
| DUSP6 | 0.1254 | 0.3429 |
| DKK3 | 46.5 | 0.366 |
| FGF18 | 2.455 | 0.366 |
| FGF22 | 1.373 | 0.3836 |
| FGF2 | 30.92 | 0.4452 |
| VIM | 4.122 | 0.4452 |
| ETV4 | 1.665 | 0.4452 |
| FGFBP3 | 4.424 | 0.4857 |
| SOX9 | 0.3956 | 0.4857 |
| SERPINE1 | 0.3155 | 0.4857 |
| SPRY1 | 0.1799 | 0.4857 |
| FGF8 | 0.3268 | 0.5338 |
| FGF20 | 0.4803 | 0.6573 |
| ELK4 | 1.019 | 0.6857 |
| FGFBP2 | 0.6526 | 0.6857 |
| FLRT3 | 0.2211 | 0.6857 |
| FGF11 | 2.039 | 0.7308 |
| FGF5 | 44.05 | 0.8294 |
| FGFR2IIIc | 2.029 | 0.8357 |
| FGF1 | 1.45 | 0.8357 |
| FGFR3 | 1.285 | 0.8357 |
| FGFR4 | 0.8265 | 0.8357 |
| FGF10 | 0.4615 | 0.8357 |
| FGF17 | 0.4268 | 0.8357 |
| ETV5 | 0.8563 | 0.8857 |
| FLRT2 | 0.828 | 0.8857 |
| FLRT1 | 0.8212 | 0.8857 |
| PLAUR | 0.716 | 0.8857 |
| FGFR3IIIb | 0.7137 | 0.8857 |
| FGFR2b | 0.5752 | 0.8857 |
| FGF16 | 1.786 | 0.9452 |
| SPRY3 | 1.051 | 0.9452 |
| FGF9 | 2.07 | 1 |
| NCAM1 | 1.391 | 1 |
| DUSP4 | 0.9031 | 1 |
| FGF3 | 0.8571 | 1 |
| FGF7 | 0.738 | 1 |

[§]Gene expression ratio determined by median gene expression in FGFR1-ECD.339-Fc responders/median gene expression in non-responders
[†]P-values are determined by a Mann-Whitney test of PCR gene expression in responders vs. non-responders for each gene using the non-FGFR1 amplified lung models in table 5.

It was examined if there was a correlation in gene expression amongst the significant gene markers identified for their association with FGFR1-ECD.339-Fc response in all models. The results of that analysis are shown in Table 10. In this experiment, there was a significant, positive correlation between the majority of the individual RNA markers identified as predictive for FGFR1-ECD.339-Fc xenograft response. For example, xenograft FGF2 RNA expression is positively correlated with FGFR3IIIc, FGFR1IIIc and FGFR1 expression (P<0.05); FGFR1 RNA expression is positively correlated with FGFR3IIIc, FGF2 and FGF18. The expression of ETV4 was not associated with other FGFR1-ECD.339-Fc responsive genes.

TABLE 10

Spearman correlation of gene expression markers predictive
of FGFR1-ECD.339-Fc efficacy in xenograft models

| Gene 1 | Gene 2 | Correlation | P-value[§] |
|---|---|---|---|
| FGF18 | FGFR1 | 0.47 | 0.0083 |
| FGF18 | FGFR1IIIc | 0.57 | 0.0008 |
| FGF2 | FGFR3IIIc | 0.49 | 0.0139 |
| FGFR1 | FGFR3IIIc | 0.41 | 0.0244 |
| FGF2 | FGFR1IIIc | 0.43 | 0.0336 |
| FGF2 | FGFR1 | 0.39 | 0.0447 |

[§]2-sided p-values approximated with a Monte Carlo simulation

Figure 14:
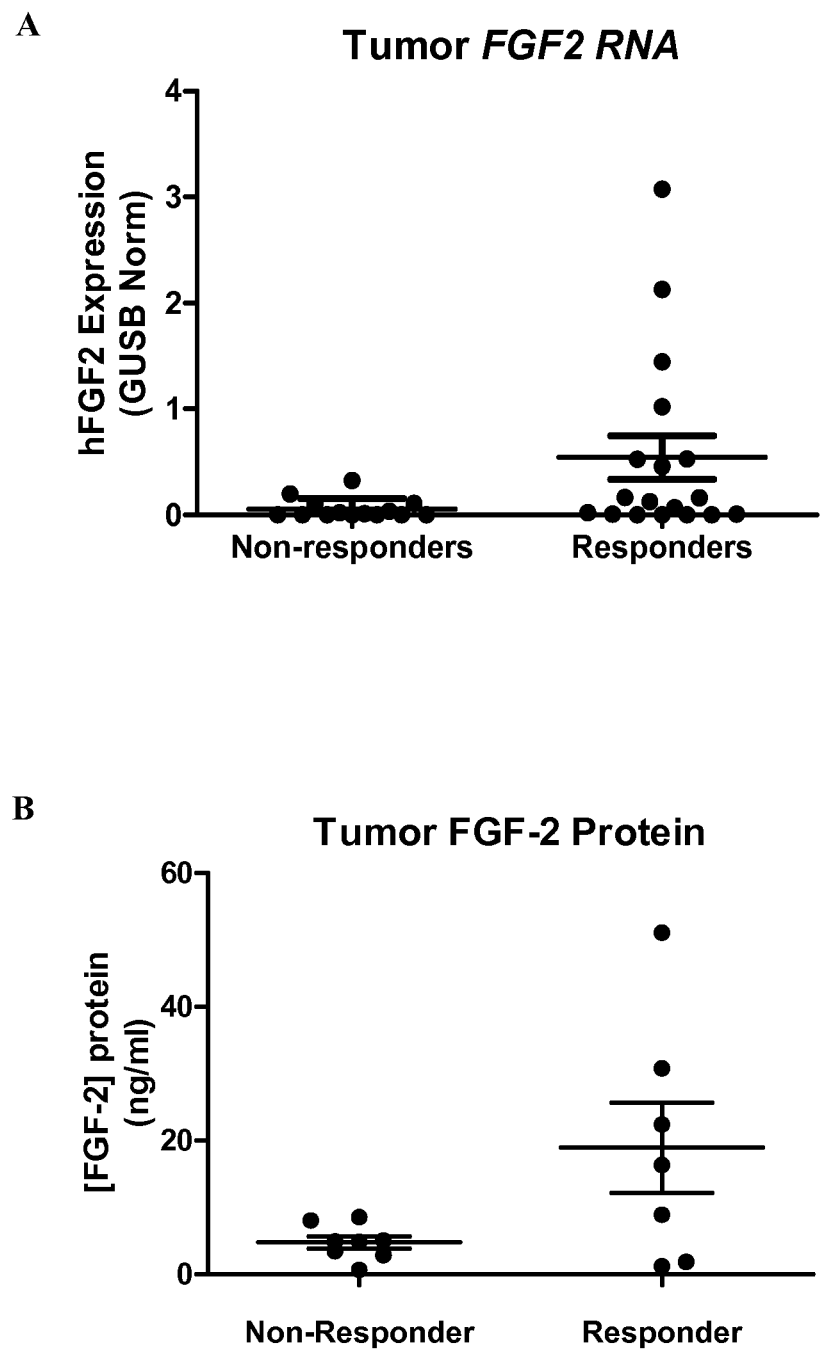
FIG. 14 shows (A) FGF2 mRNA (normalized to GUSB) and (B) FGF2 protein expression (normalized to total protein) in FGFR1-ECD.339-Fc responder and non-responder xenografts, as described in Example 8.

FIG. 14 shows (A) FGF2 mRNA (normalized to GUSB) and (B) FGF2 protein expression in FGFR1-ECD.339-Fc responder and non-responder xenografts. Expression of FGF2 (P=0.03569) was positively associated with FGFR1-ECD.339-Fc response. FGF2 displayed a high ratio (247.7-fold) of mRNA gene expression between FGFR1-ECD.339-Fc responder and non-responder xenografts. FGF2 protein levels were also confirmed to correlate with FGFR1-ECD.339-Fc response.

Figure 17:
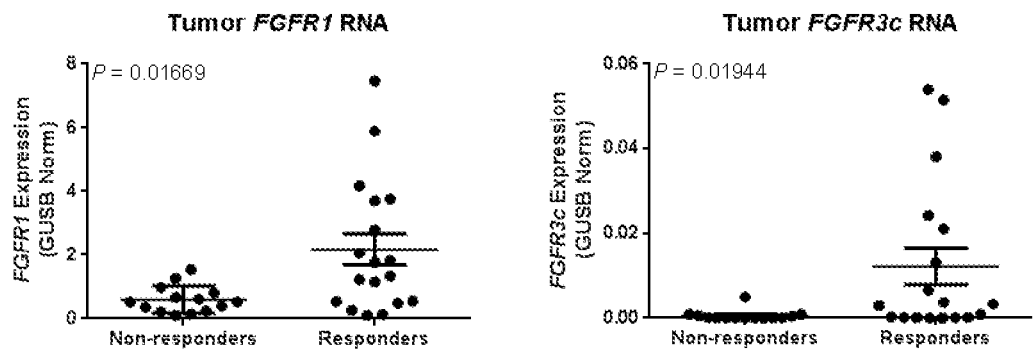
FIG. 17 shows (A) FGFR1 and (B) FGFR3IIIc mRNA expression in FGFR1-ECD.339-Fc responsive and non-responsive xenograft models, as described in Example 8.

FIG. 17 shows (A) FGFR1 mRNA expression (normalized to GUSB) and (B) FGFR3IIIc mRNA expression (normalized to GUSB) in FGFR1-ECD.339-Fc responder and non-responder xenografts. Expression of FGFR1 (P=0.01669; FIG. 17a), and the FGFR1IIIc splice variant (P=0.0431; Table 8), was positively correlated with FGFR1-ECD.339-Fc anti-tumor activity. In addition to FGFR1, expression of the FGFR3IIIc receptor (P=0.01944, Table 8) was also positively correlated with FGFR1-ECD.339-Fc anti-tumor response (FIG. 5b), reflecting the overlap in FGF-ligand binding specificity between the c-splice isoforms of FGFR1 and FGFR3 receptors (see, e.g., Zhang, et al. *J. Biol. Chem.* 281, 15694-15700 (2006); Ornitz, et al. *J. Biol. Chem.* 271, 15292-15297 (1996)).

Example 9: Predictor of FGFR1-ECD.339-Fc Response

DKK3 mRNA expression was determined in a set of 25 xenografts using qRT-PCR. RNA was extracted from tumor xenografts grown in vivo using the RNAeasy® mini kit (Qiagen, Germany). Extracted RNA was treated with DNAse I prior to creating cDNA with random hexamer priming and reverse transcriptase using the QuantiTect Reverse Transcription Kit (Qiagen, Germany). Human DKK3 RNA expression was determined using QuantiTect Primer Assays (Qiagen, Germany) employing a human GUSB control reference QuantiTect Primer Assay (Qiagen, Germany). QuantiTect SYBR Green PCR Kits (Qiagen, Germany) were used to quantify mRNA expression levels using real-time qRT-PCR and an ABI Prism ViiA™ 7 Real-Time PCR System (Applied Biosystems, Foster City, Calif.). Relative gene expression quantification was calculated according to the comparative Ct method using human GUSB as a reference and commercial RNA controls (Stratagene, La Jolla, Calif.). Relative quantification was determined according to the formula: $2^{-(\Delta Ct\ sample - \Delta Ct\ calibrator)}$.

The tumor xenografts used in this experiment are shown in Table 11. Also shown in Table 11 are the dosing schedule for FGFR1-ECD.339-Fc in a mouse xenograft model, the percent tumor growth inhibition (TGI (%)) and the statistical significance of the tumor growth inhibition (P Value).

TABLE 11

Panel of xenograft models with microarray data.

| Tumor type | Xenograft model | Cell line/ PDX | Dosing route | Dose | Dose schedule | TGI (%) | P Value |
|---|---|---|---|---|---|---|---|
| Colon | HCT116 | Cell Line | IP | 15 mg/kg | BIW | 0% | ns |
|  | Colo205 | Cell Line | IV | 5 mg/kg | BIW | 38% | P < 0.001 |
|  | Colo201 | Cell Line | IP | 15 mg/kg | BIW | 0% | ns |
| Renal | A498 | Cell Line | IP | 15 mg/kg | BIW | 7% | ns |
|  | Caki-1 | Cell Line | IV | 10 mg/kg | BIW | 81% | P < 0.001 |
| Lung | A549 | Cell Line | IP | 10 mg/kg | BIW | 38% | P < 0.05 |
|  | NCI-H460 | Cell Line | IP | 10 mg/kg | BIW | 35% | P < 0.05 |
|  | NCI-H226 | Cell Line | IP | 15 mg/kg | 3×/w | 55% | P < 0.001 |
|  | NCI-H520 | Cell Line | IP | 20 mg/kg | BIW | 47% | P < 0.05 |
|  | NCI-H1703 | Cell Line | IP | 15 mg/kg | BIW | 31% | P < 0.05 |
|  | NCI-H2126 | Cell Line | IP | 15 mg/kg | BIW | 0% | ns |
|  | NCI-H441 | Cell Line | IP | 15 mg/kg | BIW | 0% | ns |
|  | NCI-H358 | Cell Line | IP | 15 mg/kg | BIW | 0% | ns |
|  | NCI-H522 | Cell Line | IP | 10 mg/kg | BIW | 42% | P < 0.05 |
|  | NCI-H1581 | Cell Line | IP | 15 mg/kg | BIW | 74% | P = 0.002 |
|  | Calu-1 | Cell Line | IP | 15 mg/kg | BIW | 0% | ns |
| Methothelioma | MSTO-211H | Cell Line | IP | 15 mg/kg | BIW | 64% | P < 0.0001 |
| Glioblastoma | U-87 | Cell Line | IP | 15 mg/kg | BIW | 0% | ns |
|  | U-118 | Cell Line | IP | 15 mg/kg | BIW | 36% | ns |
|  | U-251 | Cell Line | IP | 15 mg/kg | BIW | 48% | P = 0.0078 |
| Retinoblastoma | Y79 | Cell Line | IP | 10 mg/kg | BIW | 0% | ns |
| Prostate | Du145 | Cell Line | IP | 0.15 mg/kg | 3×/w | 31% | ns |
| Endometrial | HEC-1B | Cell Line | IP | 15 mg/kg | BIW | 30% | P < 0.05 |
| Breast | MDA-MB-231 | Cell Line | IP | 15 mg/kg | BIW | 0% | ns |
|  | JIMT1 | Cell Line | IP | 1 mg/kg | BIW | 28% | P < 0.05 |

Gene expression was then correlated to FGFR1-ECD.339-Fc response to determine RNA expression signatures positively and negatively correlated with anti-tumor activity. Expression of DKK3 mRNA was higher in tumors that were sensitive to FGFR1-ECD.339-Fc than in tumors that were not sensitive to FGFR1-ECD.339-Fc (P=0.0069).

Figure 15:
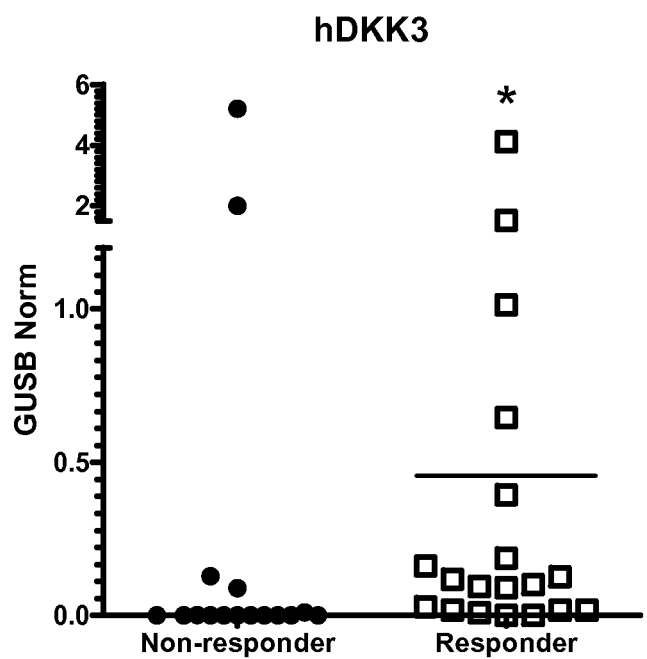
FIG. 15 shows DKK3 mRNA expression (normalized to GUSB) in FGFR1-ECD.339-Fc responder and non-responder xenografts, as described in Example 9.

FIG. 15 shows DKK3 mRNA levels (normalized to GUSB) in FGFR1-ECD.339-Fc responder and non-responder xenografts. The horizontal line indicates the median expression level for that group.

Example 10: FGFR1-ECD.339-Fc does not Increase Serum Phosphate Following High Dose Administration in Rats FGFR1-ECD.339-Fc binds to the mitogenic FGFs with 10 to 100-fold higher affinity than to FGF-23. The binding affinity of FGFR1-ECD.339-Fc for rodent FGF-23 is comparable to that of human FGF-23 by SPR analysis ($6.0 \times 10^{-8}$ vs. $6.7 \times 10^{-8}$ M). The potential biological impact of this relatively weak FGFR1-ECD.339-Fc/FGF-23 binding was investigated in rats following four weekly doses of FGFR1-ECD.339-Fc at a dose range of 10-200 mg/kg/qwk.

In the first experiment, Sprague Dawley rats (Charles River Labs; N=5/group) were dosed with vehicle, 10, 50 or 200 mg/kg/qwk of FGFR1-ECD.339-Fc for four weekly doses and plasma concentrations of FGFR1-ECD.339-Fc were determined throughout the study by an ELISA based detection method.

FGFR1-ECD.339-Fc concentration in plasma was determined using a quantitative ELISA. Briefly, recombinant human FGF-2 (R&D Systems) was immobilized on a half-well microtiter ELISA plate, blocked and incubated with test samples (diluted 1:10 with blocking buffer/20 µg/mL of heparin). The plate was subsequently washed and a dilute goat anti-human IgG-Fc HRP antibody solution (Sigma) was added and incubated. After a final wash step, a tetramethylbenzidine peroxidase substrate solution was added and incubated at ambient temperature with gentle shaking. The reaction was stopped with a phosphoric acid solution. Plates were read on a plate reader (450 nm). FGFR1-ECD.339-Fc concentrations were determined on a standard curve obtained by plotting optical density (OD) versus concentration.

In the second experiment, Sprague Dawley rats (Charles River Labs; N=5/group) were administered the FGFR kinase inhibitor PD173074 (Chemdea, Ridgewood, N.J.; 50 mg/kg/day) or vehicle control by oral gavage for 7 days; or were administered FGFR1-ECD.339-Fc (200 mg/kg) or appropriate vehicle weekly by intravenous administration. Blood samples were collected at the time points indicated and serum phosphate was determined at 24 and 168 hours post-initiation of dosing (Idexx laboratories, Westbrook, Mass.).

Figure 18:
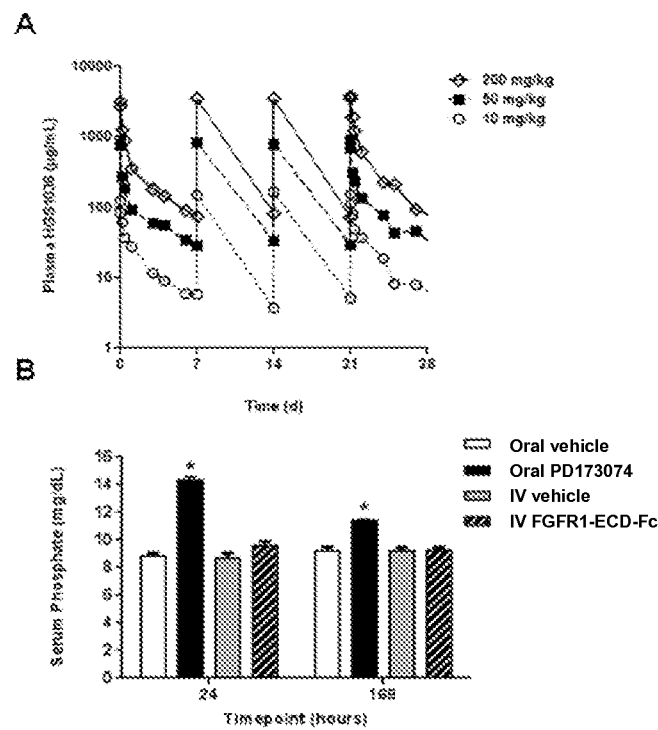
FIG. 18 shows (A) plasma FGFR1-ECD.339-Fc levels over time in rats administered weekly doses of FGFR1-ECD.339-Fc, and (B) serum phosphate levels after 24 hours and 168 hours in rats administered FGFR1-ECD.339-Fc or FGFR kinase inhibitor PD173074, as described in Example 10.

The results of those experiments are shown in FIG. 18. At the 200 mg/kg/qwk dose the maximal plasma concentration of the drug was 3.6 and 4.2 mg/ml for female and male rats, respectively (FIG. 18A). Despite these sustained high levels of drug, no significant changes in plasma phosphate were observed for any FGFR1-ECD.339-Fc dose compared to animals that received vehicle (9.61 vs. 10.19 mg/dL for vehicle and 200 mg/kg/qwk FGFR1-ECD.339-Fc, respectively). In contrast, daily dosing of rats with the small molecule FGFR kinase inhibitor PD173043 resulted in significantly elevated plasma phosphate levels either at 24 hour or 1 week of daily dosing (FIG. 18B). Additionally, histological analysis of 55 tissues in animals treated with high-dose FGFR1-ECD.339-Fc failed to reveal any changes consistent with those reported by Brown et al. (*Toxicol. Pathol.* 33, 449-455 (2005)), who observed hyperphosphatemia and calcium-phosphorus deposition in various organs following administration of a small molecule inhibitor of FGFR1 kinase activity.

In addition, FGFR1-ECD.339-Fc has completed a phase 1 dose-escalation study (N=39) of up to 16 mg/kg/qwk in patients with solid tumors. No impact of FGFR1-ECD.339-

Fc on serum phosphate was observed at any of the dose-levels examined (See, e.g., Tolcher, et al. Proceedings of the 22nd EORTC-NCI-AACR Symposium on Molecular Targets and Cancer Therapeutics (2010)). In summary, these results support the biophysical data that FGFR1-ECD.339-Fc does not bind to FGF-23 with high-affinity and does not induce hyperphosphatemia as was shown for other broad inhibitors of the FGFR pathway.

Example 11: FGFR1-ECD.339-Fc Mediated Inhibition of FGF-2 and VEGF-A Induced Angiogenesis in a Matrigel Plug Assay Recombinant human FGF-2 (final concentration 250 ng/ml; Peprotech) and/or recombinant human VEGF-A (final concentration 100 ng/ml; Peprotech) were added to matrigel (BD Biosciences, Franklin Lakes, N.J.) with sodium heparin (2 units/ml; Sigma). FGF-2 and/or VEGF-A containing matrigel plugs (one per animal) were implanted subcutaneously in the abdomen region of C57BL/6 mice (Charles River, Wilmington, Mass.). FGFR1-ECD.339-Fc was administered by tail vein injection on days 1, 4, and 7 post-matrigel implantation. On day 9, plugs were excised and processed for hematoxylin and eosin (H&E) staining. Digital images of the stained matrigel sections were generated using a Retiga 2000R digital camera (QImaging, Burnaby, BC). Image analysis was performed using Image-Pro Plus 5.1 (Media Cybernetics Inc., Silver Spring, Md.). Neovascularization was defined as the cellular response in the Matrigel plugs, consisting of newly formed blood vessels and migrated cells.

Figure 19:
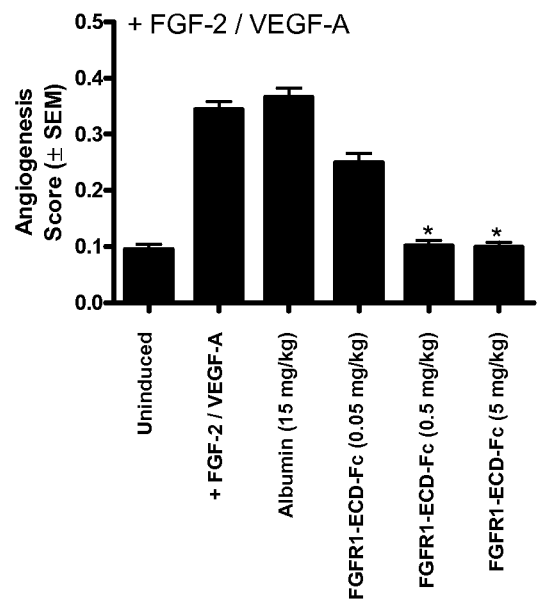
FIG. 19 shows FGFR1-ECD.339-Fc mediated inhibition of FGF-2 and VEGF-A induced angiogenesis in a matrigel plug assay, as described in Example 11.

The results of that experiment are shown in FIG. 19. Administration of 5 mg/kg or higher FGFR1-ECD.339-Fc completely blocked in vivo angiogenesis induced by a matrigel plug impregnated with FGF-2. Administration of 15 or 45 mg/kg FGFR1-ECD.339-Fc also completely blocked in vivo angiogenesis in response to a matrigel plug impregnated with VEGF-A only or FGF-2 plus VEGF-A. Anti-angiogenic activity against VEGF induced angiogenesis in this model system may reflect inhibition of the synergistic activity between VEGF in the plug and murine-derived stromal FGFs since SPR analysis shows that FGFR1-ECD.339-Fc does not directly interact with VEGF-A.

To determine whether FGFR1-ECD.339-Fc blocks VEGF-induced proliferation of endothelial cells, HUVEC cells (Life Technologies, Grand Island, N.Y.) were seeded at a density of $4 \times 10^3$ cells/well in basal media (Medium 200 (Life Technologies) with 2% heat inactivated FBS) and stimulated with either 10 ng/ml FGF2 (R&D Systems, Minneapolis, Minn.) or 15 ng/ml VEGF-A165 (R&D Systems, Minneapolis, Minn.) either in the presence of absence of 10 µg/ml FGFR1-ECD.339-Fc. HUVEC cell proliferation was determined 3 days post-stimulation using CellTiter-Glo® Luminescent Cell Viability Assay.

Figure 20:
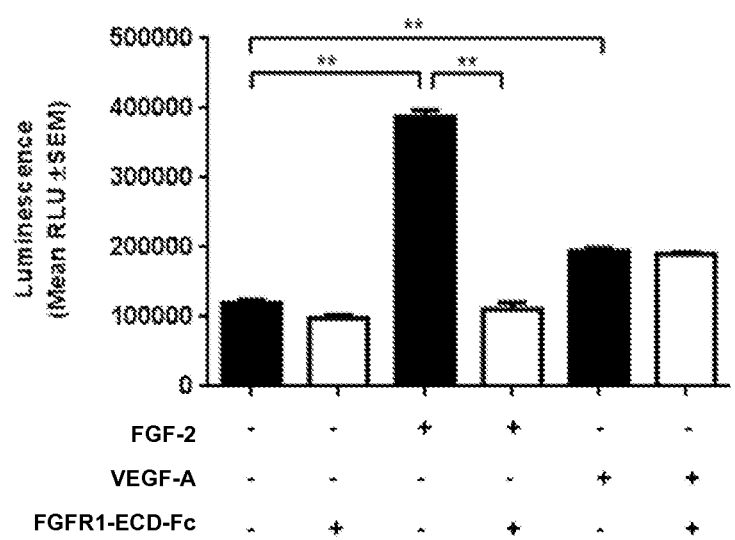
FIG. 20 shows that FGFR1-ECD.339-Fc does not inhibit VEGF-A induced human umbilical vein endothelial cell (HUVEC) proliferation, as described in Example 11.

The results of that experiment are shown in FIG. 20. FGFR1-ECD.339-Fc did not block VEGF-induced proliferation of HUVECs, although it is capable of blocking FGF-2 induced HUVEC proliferation.

Example 12: FGFR1-ECD.339-Fc Inhibits Tumor Angiogenesis in the Caki-1 Renal Cell Carcinoma Xenograft Model Human renal carcinoma Caki-1 cells ($1.5 \times 10^7$ cells/mouse) cells were implanted subcutaneously into the right flank of CB17-SCID mice. One day after tumor implantation, the mice were randomized and treated intravenously with either vehicle or FGFR1-ECD.339-Fc (5 mg/kg) twice a week. At the end of the study (Day 57), tumors were excised (N=3/gp) and used for histological analysis. Frozen sections were probed with anti-mouse CD31 monoclonal antibody (BD Biosciences, Franklin Lakes, N.J.) and visualized using HRP-conjugated secondary antibody coupled with diaminobenzidine staining (brown color). Slides were counter-stained with hematoxylin to identify cell nuclei (blue color). Representative sections are shown (5× magnification).

Figure 21:
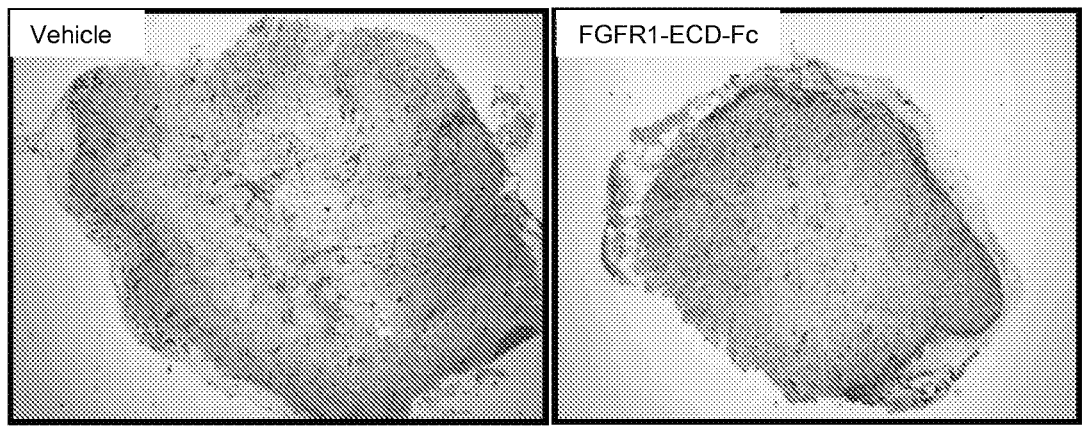
FIG. 21 shows inhibition of tumor angiogenesis (as assessed by CD31 immunostaining) in Caki-1 renal cell carcinoma xenograft model mice administered FGFR1-ECD.339-Fc, as described in Example 12.

The results of that experiment are shown in FIG. 21. Following treatment with FGFR1-ECD.339-Fc, reduced CD31 staining is observed, indicating that tumor angiogenesis was inhibited by FGFR1-ECD.339-Fc administration in this experiment.

Example 13: FGFR1-ECD.339-Fc-Mediated Inhibition of FGFR1 Signaling in the JIMT-1 Breast Cancer Xenograft Model Animals with established (200 mm3) human breast cancer JIMT-1 tumors were administered either a single (24 and 72 hour timepoints) or three times per week (multidose) i.p. dose(s) of FGFR1-ECD.339-Fc at 15 mg/kg. Tumor samples were collected at 24 and 72 hours post-dose for the single dose groups and 48 hours post the last dose in multi-dose group, snap-frozen in liquid nitrogen and lyzed in RIPA buffer (Sigma Aldrich, St Luis, Mo.). Tumor lysates were separated by SDS-PAGE and western blotting was performed using monoclonal antibodies FGFR1, pFGFR1, FRS2α, pFRS2α, Akt, pAkt, and βActin (Cell Signaling Technology, Inc). FGFR1-ECD.339-Fc was detected using anti-human Fc monoclonal antibody (Jackson Immuno Research).

Figure 22:
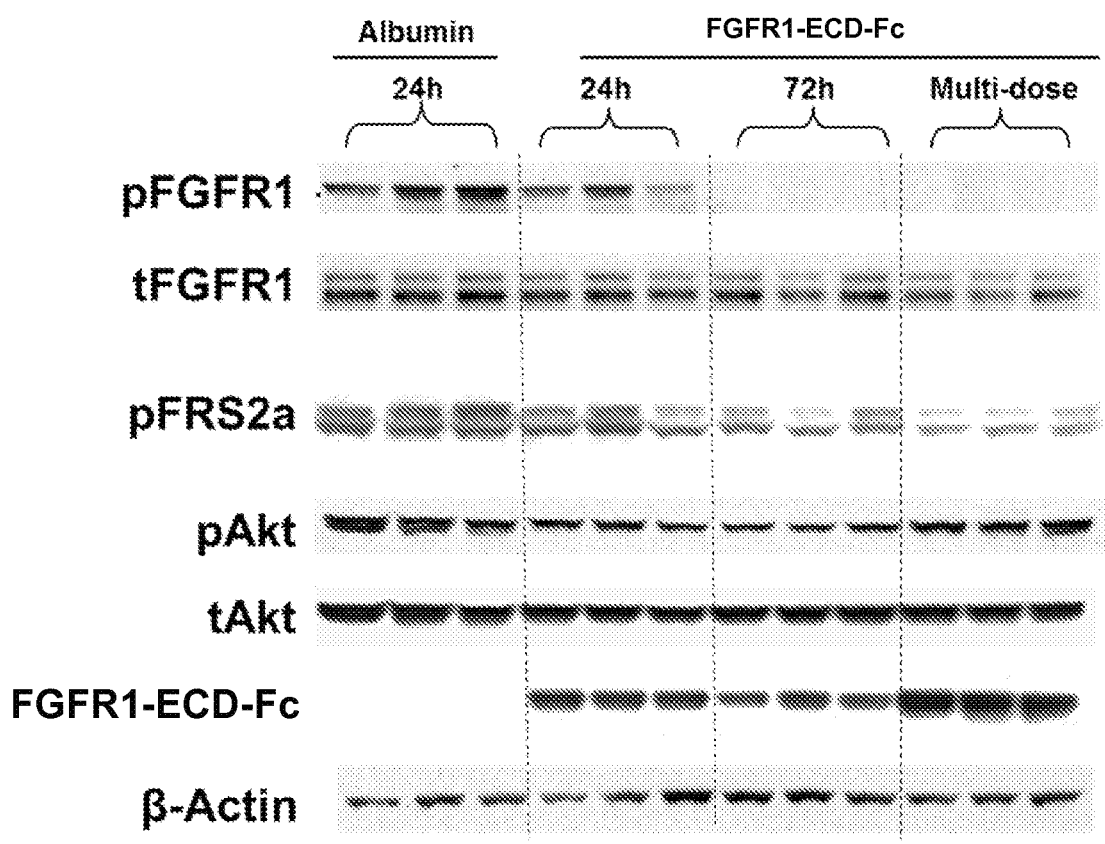
FIG. 22 shows FGFR1-ECD.339-Fc mediated inhibition of FGFR1 signaling in a JIMT-1 breast cancer xenograft, as described in Example 13.

The results of that experiment are shown in FIG. 22. FGFR1-ECD.339-Fc reduced levels of phosphorylated FGFR1 by 24 hours post-dose and completely abolished FGFR1 phosphorylation by 72 hours post-dose. Phosphorylated FRS and Akt levels were reduced 24 hours post-dose and further reduced two days later. Thus, FGFR1-ECD.339-Fc inhibited FGFR1 signaling in the JIMT-1 breast cancer xenograft model.

TABLE OF SEQUENCES

Table 6 lists certain sequences discussed herein. FGFR1 sequences are shown without the signal peptide, unless otherwise indicated.

TABLE 6

| SEQ ID NO | Description | Sequence |
| --- | --- | --- |
| 1 | Full-length human FGER1 ECD (with signal peptide); SP- | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD |

TABLE 6-continued

Sequences and Descriptions

| SEQ ID NO | Description | Sequence |
|---|---|---|
| | hFGFR1-ECD.353 | ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAVMTSP LYLE |
| 2 | Full-length human FGER1 ECD (without signal peptide); hFGFR1-ECD.353 | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAVMTSP LYLE |
| 3 | SP-hFGFR1-ECD.339 | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL |
| 4 | hFGFR1-ECD.339 | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL |
| 5 | SP-hFGFR1-ECD.339-Fc | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 6 | hFGFR1-ECD.339-Fc | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 7 | hFGFR1 signal peptide | MWSWKCLLFWAVLVTATLCTA |
| 8 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS |

TABLE 6-continued

Sequences and Descriptions

| SEQ ID NO | Description | Sequence |
|---|---|---|
| | | DIAVEWESNG QPENNYKTTP PVLDSDGSFF LYSKLTVDKS RWQQGNVFSC SVMHEALHNH YTQKSLSLSP GK |
| 9 | Exemplary Fc #1 | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 10 | Exemplary Fc #2 | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |

TABLE 7

Gene expression values for certain xenograft models from Table 5.

| Gene | A498 | A549 | Caki-1 | Calu-1 | Colo201 | Colo205 | D35087 |
|---|---|---|---|---|---|---|---|
| AREG | 0.007391 | 0.188156 | 1.24833 | 0.141611 | 1.1487 | 0.5 | 5.41702 |
| CA12 | 6.49802 | 1.46409 | 1.00696 | 0.064257 | 0.003826 | 0.011924 | NA |
| CDH1 | 0.001253 | 1.79005 | 0.269807 | 0.071298 | 3.94493 | 11.7942 | NA |
| DKK3 | 0.128514 | 0.028557 | 1.01396 | 2 | 0.000157 | 0 | 3.50594 |
| DUSP4 | 0.000171 | 0.066064 | 0.007977 | 0.028956 | 0.085378 | 0.171943 | NA |
| DUSP5 | 0.026645 | 0.102238 | 0.68302 | 0.697372 | 0.125869 | 0.07966 | NA |
| DUSP6 | 0.083043 | 0.203063 | 3.27161 | 1.18921 | 3.11666 | 0.570382 | NA |
| EGF | 0.004072 | 0.010525 | 0.036398 | 0.065607 | 0.000162 | 4.11E−05 | NA |
| EGFR | 0.646176 | 0.353553 | 0.450625 | 0.97942 | 0.558644 | 0.438303 | NA |
| ELK3 | 0.04095 | 0.307786 | 0.76313 | 1.44393 | 0.085378 | 0.065607 | NA |
| ELK4 | 0.000015 | 6.28E−05 | 0.000265 | 7.67E−05 | 0.000513 | 0.000322 | NA |
| ERBB2 | 0.096723 | 0.185565 | 0.712025 | 0.271624 | 0.528509 | 0.566442 | NA |
| ERBB3 | 0.456916 | 0.50698 | 0.22688 | 0.001677 | 1.23114 | 0.757858 | 2.53696 |
| EREG | 0 | 0.080772 | 2.11404 | 0.673617 | 1.03526 | 0.129408 | 0.03438 |
| ETV4 | 0.010672 | 0.697372 | 0.346277 | 0.351111 | 0.297302 | 0.624165 | 3.77951 |
| ETV5 | 0.034674 | 0.200267 | 0.784584 | 0.528509 | 0.303549 | 0.389582 | NA |
| FGF1 | 0.037421 | 0.00357 | 0.001186 | 0.043889 | 0.04095 | 0.021051 | 0.681223 |
| FGF10 | 0 | 1.17E−05 | 3.73E−05 | 0.000147 | 2.69E−05 | 2.19E−05 | 1.73E−05 |
| FGF11 | 0.076947 | 0.003173 | 0.01937 | 0.000644 | 0.003696 | 0.002182 | 0.753929 |
| FGF16 | 0 | 0.000348 | 0.000804 | 0.000649 | 0.002372 | 0.00143 | 0.011209 |
| FGF17 | 4.72E−05 | 0.000148 | 4.14E−05 | 0.000156 | 0.001391 | 0.00093 | 0.000251 |
| FGF18 | 0.000735 | 0.00194 | 0.004129 | 0.107321 | 0.006801 | 0.015303 | 0.012216 |
| FGF19 | 0 | 0.000207 | 0 | 0 | 0.358489 | 0.721965 | NA |
| FGF2 | 0.035158 | 0.166086 | 0.524858 | 0.000581 | 0 | 0 | NA |
| FGF20 | 0.000159 | 0.000246 | 0.018841 | 0.005799 | 0.000115 | 0 | NA |
| FGF21 | 4.29E−05 | 3.58E−05 | 0 | 2.55E−05 | 0.000918 | 0.000561 | NA |
| FGF22 | 0.003002 | 0.004581 | 0.002879 | 0.004581 | 0.003285 | 0.002244 | NA |
| FGF3 | 1.09E−05 | 0 | 0 | 0 | 0.021945 | 0.036147 | NA |
| FGF4 | 0 | 0 | 0 | 0 | 0 | 0 | NA |
| FGF5 | 0.020054 | 1.01E−05 | 0.033262 | 0.248273 | 0 | 2.83E−05 | 0.005164 |
| FGF6 | 0 | 0 | 0 | 0 | 0 | 0 | NA |
| FGF7 | 4.23E−05 | 0 | 9.3E−06 | 0.000143 | 0 | 3.01E−05 | 0 |
| FGF8 | 0.000116 | 3.12E−05 | 0.000338 | 3.63E−05 | 0.00296 | 0.000918 | 0.000517 |
| FGF9 | 0.000672 | 0.000735 | 0.001994 | 0.003545 | 0.037682 | 0.035649 | NA |
| FGFBP1 | 0.001245 | 0.111878 | 2.01391 | 0.002405 | 0.006434 | 0.0017 | NA |
| FGFBP2 | 7.46E−05 | 0.001253 | 0.005839 | 0.002137 | 0.00148 | 0.000355 | NA |
| FGFBP3 | 0.000203 | 0.001861 | 0.003217 | 0.000868 | 0.001642 | 0.002438 | NA |
| FGFR1 | 0.356012 | 0.535887 | 1.1487 | 1.53688 | 0.664343 | 0.126745 | 4.30765 |
| FGFR1IIIb | 0.000152 | 0.000309 | 0.000288 | 0.000282 | 0.000963 | 0.000456 | NA |
| FGFR1IIIc | 0.119908 | 0.131215 | 0.193446 | 0.646176 | 0.114229 | 0.009753 | 0.381142 |
| FGFR2 | 0.166086 | 0.001186 | 0.00072 | 0.001554 | 0.092142 | 0.003401 | 2.3227 |
| FGFR2IIIb | 0.009163 | 0.000334 | 8.63E−05 | 0.000169 | 0.045753 | 0.001797 | NA |
| FGFR2IIIc | 0.196146 | 0.000175 | 0.000133 | 0.000804 | 0.000275 | 8.51E−05 | 0.00162 |
| FGFR3 | 0.327598 | 0.044811 | 0.456916 | 0.033493 | 0.148651 | 0.038741 | 4.50554 |
| FGFR3IIIb | 0.006661 | 0.006003 | 0.006524 | 0.00014 | 0.023036 | 0.010167 | NA |
| FGFR3IIIc | 0.039555 | 0.001576 | 0.063813 | 0.005048 | 0 | 0 | 0.001059 |
| FGFR4 | 0.167241 | 0.111105 | 0.558644 | 0.000399 | 0.184284 | 0.107321 | 0.041146 |
| FLRT1 | 0.002489 | 0.02352 | 0.01209 | 0.007867 | 0.040107 | 0.076415 | NA |
| FLRT2 | 4.03E−05 | 0.042986 | 0.003879 | 1.12506 | 0 | 5.24E−05 | NA |
| FLRT3 | 0.001586 | 0.051474 | 0.042986 | 0.000052 | 0.000186 | 0.001773 | NA |

TABLE 7-continued

Gene expression values for certain xenograft models from Table 5.

| | | | | | | | |
|---|---|---|---|---|---|---|---|
| HGF | 0 | 0.007977 | 0.033961 | 0.000725 | 0 | 0 | 0 |
| IGF1 | 0.000405 | 0.002613 | 0 | 0.000381 | 3.25E−05 | 0 | NA |
| IGF1R | 0.02977 | 0.598739 | 0.071794 | 0.469761 | 1.10957 | 1.01396 | NA |
| IGF2 | 0.004129 | 0.05954 | 0.060371 | 0.043285 | 0.002438 | 0.000299 | NA |
| KDR | 0.000502 | 8.34E−05 | 0.000238 | 0.01418 | 0.000478 | 0.000122 | 0.000281 |
| MET | 1.28343 | 0.503478 | 7.26015 | 1.50525 | 0.790041 | 0.366021 | NA |
| MMP1 | 2.51E−05 | 0.018841 | 0.007599 | 0.303549 | 0.000413 | 0.000899 | NA |
| MMP2 | 1.54E−05 | 0.030186 | 0.888843 | 2.39496 | 0 | 0 | 12.3138 |
| NCAM1 | 0.05366 | 5.85E−05 | 0.000485 | 0.000394 | 0.000159 | 2.44E−05 | NA |
| PDGFRa | 0.000627 | 0.00095 | 0.173139 | 0.219151 | 0 | 0 | 0.023016 |
| PDGFRb | 0.001887 | 0.000735 | 0.021793 | 0.952638 | 0.002405 | 0.001114 | NA |
| PLAU | 0.013888 | 0.267943 | 5.20537 | 0.456916 | 0.271684 | 0.289172 | NA |
| PLAUR | 0.228458 | 0.97942 | 0.920188 | 1.94531 | 0.582367 | 0.248273 | NA |
| SERPINE1 | 0.61132 | 0.230047 | 1.94531 | 9.00047 | 0.077482 | 0.105843 | NA |
| SOX9 | 0.602904 | 1.26576 | 2.82843 | 1.72907 | 1.87905 | 4.85678 | NA |
| SPRY1 | 0.013415 | 0.022718 | 0.160428 | 0.198884 | 0.119908 | 0.186856 | NA |
| SPRY2 | 0.028756 | 0.136787 | 0.5 | 0.301452 | 0.395021 | 0.50698 | NA |
| SPRY3 | 0.002668 | 0.003086 | 0.014579 | 0.001491 | 0.002668 | 0.003521 | 0.003134 |
| SPRY4 | 0.002372 | 0.001565 | 0.005336 | 0.022876 | 0.009163 | 0.020905 | NA |
| TGFa | 0.456916 | 0.051833 | 0.258816 | 0.009552 | 0.271684 | 0.127626 | NA |
| TNC | 0.002542 | 0.007139 | 0.222211 | 1.67018 | 0.50698 | 0.123279 | NA |
| VIM | 27.0958 | 13.8326 | 122.786 | 60.9688 | 0.336808 | 0.166086 | 43.9259 |

| Gene | D35376 | D37638 | DMS114 | DMS53 | Du145 | G-401 | HCT116 |
|---|---|---|---|---|---|---|---|
| AREG | 0.004051 | 1.51362 | 0.000292 | 0.008144 | 0.166086 | 0.0019 | 2.18859 |
| CA12 | NA | NA | NA | NA | 0.015303 | 0.02936 | 0.026278 |
| CDH1 | NA | NA | NA | NA | 0.933033 | 0.003262 | 1.09429 |
| DKK3 | 0.000737 | 3.12315 | NA | NA | 0.010237 | 0.018073 | 5.43E−05 |
| DUSP4 | NA | NA | NA | NA | 0.01468 | 0.000155 | 0.052193 |
| DUSP5 | NA | NA | NA | NA | 0.028956 | 0.011281 | 0.316439 |
| DUSP6 | NA | NA | NA | NA | 0.692555 | 2.63902 | 4.08405 |
| EGF | NA | NA | 0 | 0.000918 | 0.065607 | 1.09E−05 | 0.008609 |
| EGFR | NA | NA | NA | NA | 0.594604 | 0.000399 | 1.42405 |
| ELK3 | NA | NA | NA | NA | 0.041521 | 0.156041 | 0.234881 |
| ELK4 | NA | NA | NA | NA | 0.000023 | 6.28E−05 | 0.000104 |
| ERBB2 | NA | NA | NA | NA | 0.389582 | 0.121582 | 0.217638 |
| ERBB3 | 0.000903 | 0.108909 | 0.001913 | 0.012691 | 0.260616 | 0.031686 | 0.231647 |
| EREG | 0 | 0.002591 | 0 | 9.93E−06 | 0.034197 | 0.003853 | 5.65685 |
| ETV4 | 0.151082 | 1.54928 | NA | NA | 0.014579 | 1.20581 | 0.15822 |
| ETV5 | NA | NA | NA | NA | 0.046071 | 0.426317 | 0.371131 |
| FGF1 | 0.000328 | 0.050036 | NA | NA | 0.001631 | 0.000176 | 0.034674 |
| FGF10 | 0.000157 | 0.00023 | NA | NA | 3.39E−05 | 0.5 | 0.000192 |
| FGF11 | 0.012728 | 0.101173 | NA | NA | 0.008669 | 0.251739 | 0.022876 |
| FGF16 | 0.026669 | 0.026479 | NA | NA | 0.000585 | 0.000311 | 0.000918 |
| FGF17 | 0.000632 | 0.006306 | NA | NA | 0.006801 | 0.000681 | 0.011359 |
| FGF18 | 0.000445 | 0.002484 | NA | NA | 0.00286 | 0.003826 | 0.03082 |
| FGF19 | NA | NA | NA | NA | 0.000128 | 0.000937 | 0.035897 |
| FGF2 | NA | NA | NA | NA | 0.107321 | 0.008373 | 0.10083 |
| FGF20 | NA | NA | NA | NA | 0.00145 | 0.30566 | 0.00613 |
| FGF21 | NA | NA | NA | NA | 0.000193 | 4.59E−05 | 0.000231 |
| FGF22 | NA | NA | NA | NA | 0.008373 | 0.002668 | 0.01937 |
| FGF3 | NA | NA | NA | NA | 0 | 6.23E−05 | 0.000331 |
| FGF4 | NA | NA | NA | NA | 0 | 0 | 0 |
| FGF5 | 5.91E−05 | 0.000808 | NA | NA | 0 | 1.84E−05 | 0 |
| FGF6 | NA | NA | NA | NA | 0.000052 | 0 | 0.00015 |
| FGF7 | 0 | 0 | NA | NA | 7.11E−05 | 0.000233 | 0.000045 |
| FGF8 | 0.000961 | 0.001714 | NA | NA | 0.000301 | 0.01541 | 0.006003 |
| FGF9 | NA | NA | NA | NA | 0.003065 | 0.001137 | 0.009227 |
| FGFBP1 | NA | NA | NA | NA | 0.050067 | 0 | 0.248273 |
| FGFBP2 | NA | NA | NA | NA | 0.001211 | 0.00029 | 0.005048 |
| FGFBP3 | NA | NA | NA | NA | 0.000618 | 0.060371 | 0.00588 |
| FGFR1 | 0.581641 | 0.709808 | 0.678302 | 0.078563 | 0.220676 | 1.32869 | 0.517632 |
| FGFR1IIIb | NA | NA | 0 | 0 | 0.001665 | 5.62E−05 | 0.085378 |
| FGFR1IIIc | 0.069464 | 0.386462 | 0.027585 | 0.01698 | 0.057512 | 0.473029 | 0.063373 |
| FGFR2 | 0.000917 | 1.05416 | 0.008974 | 0.001084 | 0.033032 | 1.22264 | 0.137738 |
| FGFR2IIIb | NA | NA | NA | NA | 0.023036 | 0.049721 | 0.118257 |
| FGFR2IIIc | 0.000498 | 0.012137 | NA | NA | 0.00075 | 0.972655 | 0.000294 |
| FGFR3 | 0.009346 | 0.580312 | 0.009163 | 0.002093 | 0.033262 | 0.025559 | 0.329877 |
| FGFR3IIIb | NA | NA | NA | NA | 0.005799 | 0.000844 | 0.030607 |
| FGFR3IIIc | 9.87E−05 | 0.00035 | NA | NA | 0.000135 | 0.003747 | 6.36E−05 |
| FGFR4 | 0.000564 | 0.009061 | 0.002879 | 0.000168 | 0.004395 | 0.015953 | 0.042394 |
| FLRT1 | NA | NA | NA | NA | 0.01698 | 0.005839 | 0.034197 |
| FLRT2 | NA | NA | NA | NA | 0.009889 | 0.010027 | 0 |
| FLRT3 | NA | NA | NA | NA | 0.007867 | 0.000886 | 0.002372 |
| HGF | 0.044508 | 0.009057 | NA | NA | 6.2E−06 | 2.23457 | 0 |
| IGF1 | NA | NA | NA | NA | 0.002036 | 0.000294 | 0 |
| IGF1R | NA | NA | NA | NA | 0.297302 | 0.065154 | 0.088388 |

TABLE 7-continued

Gene expression values for certain xenograft models from Table 5.

| | | | | | | | |
|---|---|---|---|---|---|---|---|
| IGF2 | NA | NA | NA | NA | 0.006754 | 0.104386 | 0.20166 |
| KDR | 0.000377 | 0.009784 | NA | NA | 0.00294 | 0.000142 | 0.000557 |
| MET | NA | NA | NA | NA | 0.119908 | 0.003747 | 1.1487 |
| MMP1 | NA | NA | NA | NA | 0.044502 | 0.000184 | 0.002339 |
| MMP2 | 0.000158 | 0.138658 | NA | NA | 0 | 0.325336 | 0 |
| NCAM1 | NA | NA | NA | NA | 0.000061 | 0.562529 | 0.003401 |
| PDGFRa | 0.005323 | 0.038353 | NA | NA | 0.000208 | 0.001748 | 0 |
| PDGFRb | NA | NA | NA | NA | 0.001381 | 0.007443 | 0.00294 |
| PLAU | NA | NA | NA | NA | 0.289172 | 0.00324 | 0.297302 |
| PLAUR | NA | NA | NA | NA | 0.194791 | 0.035403 | 0.429283 |
| SERPINE1 | NA | NA | NA | NA | 0.03983 | 0.001153 | 0.45376 |
| SOX9 | NA | NA | NA | NA | 0.063813 | 0.012174 | 1.94531 |
| SPRY1 | NA | NA | NA | NA | 0.004876 | 0.088388 | 0.030396 |
| SPRY2 | NA | NA | NA | NA | 0.027017 | 0.721965 | 0.055553 |
| SPRY3 | 0.00269 | 0.006099 | 7.89E−05 | 0.000644 | 0.007599 | 0.007922 | 0.020054 |
| SPRY4 | NA | NA | NA | NA | 0.000162 | 0.00162 | 0.003773 |
| TGFa | NA | NA | NA | NA | 0.05954 | 0.000428 | 0.121582 |
| TNC | NA | NA | NA | NA | 0.014579 | 0.000162 | 0.000118 |
| VIM | 16.4293 | 3.26549 | NA | NA | 2.15846 | 38.5858 | 0.051119 |

| Gene | HEC-1B | JIMT1 | LXFA-629 | LXFA-737 | MDA-MB-231 | MFE-280 | MFE-319 |
|---|---|---|---|---|---|---|---|
| AREG | 0.000804 | 0.0625 | 0.794269 | 0.941087 | 1.37554 | 0.001511 | 0.001271 |
| CA12 | 2.8481 | 0.010672 | NA | NA | 0.119908 | 0.02683 | 0.035403 |
| CDH1 | 0.033493 | 3.20428 | NA | NA | 0.000139 | 0.602904 | 0.895025 |
| DKK3 | 0.646176 | 0.118257 | 0.039949 | 0.067093 | 0.000516 | 0.188156 | 0.000761 |
| DUSP4 | 0.000446 | 0.023683 | NA | NA | 0.070805 | 0.001511 | 6.87E−05 |
| DUSP5 | 0.203063 | 0.050067 | NA | NA | 0.432269 | 0.039282 | 0.02936 |
| DUSP6 | 2.36199 | 0.183011 | NA | NA | 3.68075 | 1.3566 | 0.084202 |
| EGF | 0.00588 | 0.023196 | NA | NA | 0.011125 | 0.001061 | 0.00362 |
| EGFR | 0.432269 | 3.03143 | NA | NA | 1.86607 | 0.092783 | 0.307786 |
| ELK3 | 0.628507 | 0.154963 | NA | NA | 0.539614 | 0.03983 | 0.037163 |
| ELK4 | 0.000032 | 0.00143 | NA | NA | 8.28E−05 | 0 | 8.3E−06 |
| ERBB2 | 0.535887 | 5.06303 | NA | NA | 0.11744 | 1.31039 | 0.48971 |
| ERBB3 | 0.072293 | 0.271684 | 0.152936 | 1.94598 | 0.046071 | 0.309927 | 0.080214 |
| EREG | 2.08E−05 | 0.06164 | 0.067803 | 0.041083 | 0.25349 | 1.78E−05 | 0.000119 |
| ETV4 | 0.528509 | 0.493116 | 0.185141 | 0.889459 | 0.210224 | 0.888843 | 0.011598 |
| ETV5 | 0.371131 | 0.179244 | NA | NA | 0.248273 | 0.05672 | 0.017824 |
| FGF1 | 0.003354 | 0.036398 | 0.0984 | 0.004799 | 0.077482 | 0.000462 | 0.001032 |
| FGF10 | 3.03E−05 | 0 | 3.2E−05 | 2.51E−05 | 3.23E−05 | 0.000168 | 4.9E−06 |
| FGF11 | 0.009552 | 0.017948 | 0.173307 | 0.554631 | 0.003086 | 0.057115 | 0.009037 |
| FGF16 | 9.78E−05 | 0.002137 | 0.016327 | 0.025879 | 0.000341 | 0.000485 | 0.000147 |
| FGF17 | 0.000821 | 0.024349 | 0.000633 | 0.003234 | 0.000391 | 0.034197 | 0.013139 |
| FGF18 | 1.45397 | 0.057115 | 0.00032 | 0.001085 | 0.001362 | 0.049378 | 0.043586 |
| FGF19 | 0 | 0 | NA | NA | 7.26E−05 | 0.008432 | 7.3E−06 |
| FGF2 | 0.021793 | 0 | NA | NA | 0 | 0.009889 | 0.001598 |
| FGF20 | 0.006896 | 0 | NA | NA | 0.001785 | 0.001004 | 0.000016 |
| FGF21 | 2.66E−05 | 0.000452 | NA | NA | 1.25E−05 | 0.000084 | 7.1E−06 |
| FGF22 | 0.00519 | 0.019237 | NA | NA | 0.003401 | 0.012691 | 0.049037 |
| FGF3 | 0.000011 | 0.001289 | NA | NA | 0 | 0.000735 | 0 |
| FGF4 | 0 | 0 | NA | NA | 0 | 0.000437 | 0 |
| FGF5 | 0.001011 | 0.004364 | 0.006428 | 5.47E−05 | 0.181747 | 2.23E−05 | 7.8E−06 |
| FGF6 | 0 | 0 | NA | NA | 9.5E−06 | 0 | 3.09E−05 |
| FGF7 | 2.14E−05 | 0 | 0 | 0 | 4.14E−05 | 9.85E−05 | 0.003173 |
| FGF8 | 0.001325 | 0.00064 | 7.08E−05 | 0.000522 | 8.11E−05 | 0.000331 | 0.000368 |
| FGF9 | 0.001011 | 0.008549 | NA | NA | 0.000495 | 0.001245 | 0.013697 |
| FGFBP1 | 0.20733 | 0.664343 | NA | NA | 0.002244 | 0.002355 | 0.002065 |
| FGFBP2 | 0.003195 | 0.000428 | NA | NA | 0.000127 | 0.001887 | 0.003961 |
| FGFBP3 | 0.000267 | 0.003065 | NA | NA | 0.00734 | 0.001047 | 0.00162 |
| FGFR1 | 0.479632 | 5.89708 | 0.6208 | 0.448755 | 0.524858 | 1.22264 | 0.554785 |
| FGFR1IIIb | 0.000475 | 0.204476 | NA | NA | 0.00097 | 0.00734 | 0.000509 |
| FGFR1IIIc | 0.236514 | 1.86607 | 0.114633 | 0.108525 | 0.204476 | 1.02101 | 0.267943 |
| FGFR2 | 0.050067 | 1.21419 | 0.121945 | 0.001513 | 0.003065 | 0.027394 | 0.211686 |
| FGFR2IIIb | 0.012344 | 0.602904 | NA | NA | 0.001169 | 0.014279 | 0.160428 |
| FGFR2IIIc | 0.016289 | 0.005448 | 2.79E−05 | 0.000266 | 0.000137 | 0.001178 | 0.009486 |
| FGFR3 | 0.200267 | 0.840896 | 1.05256 | 1.51215 | 0.005154 | 0.094732 | 0.062935 |
| FGFR3IIIb | 0.023196 | 0.148651 | NA | NA | 0.00147 | 0.007391 | 0.005486 |
| FGFR3IIIc | 0.013139 | 0.000194 | 0.000669 | 0.000864 | 0.000132 | 0.000144 | 0.000152 |
| FGFR4 | 0.225313 | 0.094732 | 0.005931 | 0.111491 | 0.000523 | 0.013985 | 0.004581 |
| FLRT1 | 0.00362 | 0.018711 | NA | NA | 0.031034 | 0.041521 | 0.040667 |
| FLRT2 | 0.001677 | 0 | NA | NA | 0.069348 | 0.00362 | 0.089003 |
| FLRT3 | 0.041521 | 0 | NA | NA | 2.87E−05 | 0.002228 | 0.034197 |
| HGF | 2.62E−05 | 0 | 4.75E−05 | 0 | 0 | 5.13E−05 | 2.36E−05 |
| IGF1 | 0 | 0.000581 | NA | NA | 0.000045 | 0.030186 | 0.000653 |
| IGF1R | 0.125869 | 0.61132 | NA | NA | 0.200267 | 0.063373 | 0.004743 |
| IGF2 | 0.137738 | 0.196146 | NA | NA | 0.034197 | 0.0625 | 0.11744 |
| KDR | 0.000375 | 0.000233 | 0.000274 | 0.000304 | 0.01038 | 0.000686 | 0.001532 |

TABLE 7-continued

Gene expression values for certain xenograft models from Table 5.

| | | | | | | | |
|---|---|---|---|---|---|---|---|
| MET | 4.46915 | 0.920188 | NA | NA | 0.450625 | 0.019915 | 0.057115 |
| MMP1 | 0.021642 | 0.00162 | NA | NA | 0.45376 | 0.00093 | 0.002981 |
| MMP2 | 0.162668 | 0.038741 | 0.67301 | 0.009119 | 0.000419 | 0.001381 | 0.000509 |
| NCAM1 | 0.000104 | 9.58E−05 | NA | NA | 9.7E−06 | 0.039555 | 0.010027 |
| PDGFRa | 8.51E−05 | 0.001011 | 4.55E−06 | 0.001835 | 0.004016 | 0.018581 | 0.001253 |
| PDGFRb | 0.000862 | 0.002559 | NA | NA | 0.019915 | 0.003521 | 0.001025 |
| PLAU | 1.34723 | 1.40444 | NA | NA | 2.32947 | 0.007139 | 0.004581 |
| PLAUR | 0.316439 | 0.632878 | NA | NA | 0.757858 | 0.080772 | 0.008201 |
| SERPINE1 | 0.096723 | 7.51618 | NA | NA | 2.82843 | 0.008432 | 0.001069 |
| SOX9 | 0.858565 | 0.000145 | NA | NA | 0.429283 | 0.149685 | 0.004395 |
| SPRY1 | 0.234881 | 0.00982 | NA | NA | 0.061214 | 0.039282 | 0.014989 |
| SPRY2 | 0.271684 | 0.035403 | NA | NA | 0.297302 | 0.017098 | 0.029157 |
| SPRY3 | 0.008432 | 0.012604 | 0.001365 | 0.045286 | 0.004518 | 0.006087 | 0.015843 |
| SPRY4 | 0.020334 | 0.002981 | NA | NA | 0.018581 | 0.001861 | 0.000821 |
| TGFa | 0.118257 | 0.120742 | NA | NA | 0.034915 | 0.027776 | 0.087172 |
| TNC | 0.01541 | 0.737135 | NA | NA | 0.146604 | 0.020617 | 0.00613 |
| VIM | 69.551 | 5.54044 | 0.091157 | 0.065954 | 44.3235 | 2.39496 | 0.463294 |

| Gene | MSTO-211H | NCI-H1581 | NCI-H1703 | NCI-H2126 | NCI-H226 | NCI-H358 | NCI-H441 |
|---|---|---|---|---|---|---|---|
| AREG | 0.0017 | 0.000868 | 1.87E−05 | 0.064704 | 0.013048 | 5.73582 | 2.44528 |
| CA12 | 0.084788 | 0.084202 | 0.000012 | 0.003645 | 0.015734 | 0 | 0 |
| CDH1 | 0.009618 | 0.073302 | 0.000772 | 1.81504 | 0.042986 | 12.7286 | 9.84916 |
| DKK3 | 4.11246 | 0.127626 | 0.094732 | 0.000255 | 0.161544 | 0 | 3.71E−05 |
| DUSP4 | 0.000309 | 0.000219 | 0.0007 | 0.045123 | 0.003496 | 0.040386 | 0.013508 |
| DUSP5 | 0.186856 | 0.02797 | 0.02977 | 0.02836 | 0.174343 | 0.223756 | 0.190782 |
| DUSP6 | 0.255253 | 1.47427 | 0.149685 | 0.062935 | 0.063813 | 4.34694 | 2.86791 |
| EGF | 0.003595 | 0.000997 | 0.00011 | 0.000542 | 0.00982 | 0.07966 | 0.049721 |
| EGFR | 1.56917 | 0.108819 | 0.34151 | 0.460094 | 3.05252 | 0.628507 | 0.895025 |
| ELK3 | 0.473029 | 0.214641 | 0.376312 | 0.063813 | 0.435275 | 0.463294 | 0.329877 |
| ELK4 | 3.97E−05 | 3.55E−05 | 0.000788 | 2.85E−05 | 4.44E−05 | 2.64E−05 | 0.00181 |
| ERBB2 | 0.189465 | 0.368567 | 0.246558 | 0.20733 | 0.156041 | 0.641713 | 0.482968 |
| ERBB3 | 0.011125 | 0.208772 | 0.00942 | 0.099442 | 0.073812 | 0.721965 | 0.447513 |
| EREG | 0 | 0.000157 | 1.41E−05 | 2.93E−05 | 0.000145 | 0.907519 | 1.18099 |
| ETV4 | 0.063813 | 0.408951 | 0.466516 | 0.019641 | 0.166086 | 0.230047 | 0.148651 |
| ETV5 | 0.15932 | 0.271684 | 0.907519 | 0.03125 | 0.293209 | 0.183011 | 0.20733 |
| FGF1 | 0.007813 | 0.00564 | 0.002668 | 0.000158 | 0.016289 | 0.0819 | 0.006849 |
| FGF10 | 0.000194 | 0.000546 | 9.58E−05 | 1.35E−05 | 0.000343 | 7.31E−05 | 3.58E−05 |
| FGF11 | 0.022876 | 0.301452 | 0.001543 | 0.00282 | 0.005486 | 0.042394 | 0.019641 |
| FGF16 | 0.002079 | 0.000523 | 7.46E−05 | 0.000239 | 0.002372 | 0.00029 | 0.001099 |
| FGF17 | 4.32E−05 | 0.00879 | 0.001887 | 0.000117 | 0.001091 | 0.002307 | 1.46E−05 |
| FGF18 | 0.005373 | 0.119908 | 0.005154 | 0.000549 | 0.619854 | 0.000686 | 0.000816 |
| FGF19 | 9.25E−05 | 0.01038 | 2.25E−05 | 5.7E−05 | 3.63E−05 | 0.000804 | 0 |
| FGF2 | 3.07375 | 0.528509 | 0.069348 | 7.26E−05 | 2.12874 | 0.000273 | 4.63E−05 |
| FGF20 | 0.008432 | 0.121582 | 0.000174 | 0 | 0 | 0.000478 | 3.36E−05 |
| FGF21 | 0 | 2.01E−05 | 6.28E−05 | 0.000003 | 7.94E−05 | 0 | 9.9E−06 |
| FGF22 | 0.004158 | 0.009685 | 0.003173 | 0.00162 | 0.014082 | 0.00292 | 0.004843 |
| FGF3 | 0 | 0.000109 | 0 | 1.12E−05 | 6.28E−05 | 3.48E−05 | 0 |
| FGF4 | 0 | 0 | 0 | 0 | 0 | 0 | 0 |
| FGF5 | 0.939523 | 0.00181 | 0.514057 | 0 | 0.148651 | 0.002595 | 0 |
| FGF6 | 0 | 1.11E−05 | 2.68E−05 | 4.1E−06 | 3.03E−05 | 0 | 0 |
| FGF7 | 0.013322 | 0.001609 | 0.000378 | 2.87E−05 | 4.11E−05 | 0.000112 | 2.08E−05 |
| FGF8 | 0.000472 | 0.10083 | 0.000495 | 1.39E−05 | 0.000193 | 0.000397 | 0.000695 |
| FGF9 | 0.002008 | 0.001253 | 0.000146 | 0.000234 | 0.028164 | 0.070316 | 0.010599 |
| FGFBP1 | 0.111105 | 0.000782 | 2.77E−05 | 0.007239 | 0.469761 | 2.88786 | 0.607097 |
| FGFBP2 | 0.000109 | 0.000478 | 4.03E−05 | 0.002743 | 0.000318 | 0.00128 | 0.000296 |
| FGFBP3 | 0.004187 | 3.20428 | 0.001797 | 0.000597 | 0.00012 | 0.002405 | 0.001773 |
| FGFR1 | 3.75809 | 2.05623 | 1.76541 | 0.146604 | 3.70635 | 0.607097 | 0.397768 |
| FGFR1IIIb | 0.000593 | 5.54E−05 | 0.000228 | 0.000589 | 0.00141 | 0.000362 | 0.001654 |
| FGFR1IIIc | 1.33793 | 1.17283 | 0.521233 | 0.011842 | 1.12506 | 0.045437 | 0.048027 |
| FGFR2 | 0.002152 | 4.85678 | 0.02936 | 0.00071 | 0.023196 | 0.033726 | 0.001861 |
| FGFR2IIIb | 0.000644 | 0.303549 | 0.001773 | 0.000277 | 0.009355 | 0.020054 | 0.001106 |
| FGFR2IIIc | 0.000345 | 3.78423 | 0.008974 | 4.35E−05 | 0.006302 | 0.000531 | 0.000173 |
| FGFR3 | 0.008315 | 0.043586 | 0.277392 | 0.051119 | 0.086569 | 0.156041 | 0.00367 |
| FGFR3IIIb | 7.57E−05 | 0.001835 | 0.01278 | 0.00849 | 0.005719 | 0.009889 | 2.23E−05 |
| FGFR3IIIc | 0.00088 | 0.006615 | 0.035403 | 0.000026 | 0.003377 | 0.000443 | 0 |
| FGFR4 | 0.001343 | 0.004645 | 0.010309 | 0.005048 | 0.001642 | 0.004581 | 0.004334 |
| FLRT1 | 0.004044 | 0.029564 | 0.036906 | 0.027017 | 0.002743 | 0.016863 | 0.033961 |
| FLRT2 | 0.028164 | 0.008729 | 0.41466 | 0.013048 | 0.11908 | 0.118257 | 0.077482 |
| FLRT3 | 2.77E−05 | 0.002559 | 0.001114 | 0.190782 | 0.001665 | 0.005226 | 0.005563 |
| HGF | 6.59E−05 | 0.005524 | 2.44E−05 | 0.00013 | 0 | 0 | 0 |
| IGF1 | 0 | 0.006801 | 9.71E−05 | 0.000005 | 3.97E−05 | 0.030186 | 0.008729 |
| IGF1R | 0.275476 | 0.965936 | 0.021793 | 0.179244 | 0.840896 | 0.737135 | 0.211686 |
| IGF2 | 2.36199 | 0.047366 | 0.005448 | 0.048361 | 0.023357 | 0.214641 | 3.94E−05 |
| KDR | 0.001253 | 0.004044 | 4.03E−05 | 8.63E−05 | 0.036398 | 0.5 | 0.271684 |
| MET | 1.75321 | 0.017337 | 0.128514 | 0.173139 | 2.53151 | 0.558644 | 4.82323 |
| MMP1 | 0.035403 | 0.022718 | 0.307786 | 0.002542 | 0.058315 | 0.503478 | 0.001797 |

TABLE 7-continued

Gene expression values for certain xenograft models from Table 5.

| | | | | | | | |
|---|---|---|---|---|---|---|---|
| MMP2 | 3.11666 | 0.004809 | 0.003906 | 0.001099 | 0.078563 | 0 | 0 |
| NCAM1 | 0.002524 | 0.000174 | 5.13E−05 | 0.000413 | 0.000856 | 0.000264 | 0.000169 |
| PDGFRa | 0.005962 | 0.486327 | 6.45313 | 0.000142 | 0.001926 | 0.001253 | 6.73E−05 |
| PDGFRb | 0.392292 | 0.178006 | 0.000627 | 0 | 0.267943 | 0.004518 | 0.001654 |
| PLAU | 1.6358 | 0.641713 | 0.00471 | 0.054788 | 0.021793 | 1.43396 | 3.53081 |
| PLAUR | 0.646176 | 0.11908 | 0.143587 | 0.447513 | 2.23457 | 0.773782 | 0.732043 |
| SERPINE1 | 37.7918 | 0.275476 | 1.07923 | 0.06983 | 18.1261 | 0.316439 | 0.554785 |
| SOX9 | 0.417544 | 0.450625 | 0.006087 | 0.214641 | 0.124137 | 1.45397 | 0.103665 |
| SPRY1 | 0.012344 | 0.50698 | 0.185565 | 0.010525 | 0.00879 | 0.119908 | 0.0625 |
| SPRY2 | 0.044502 | 0.030186 | 0.021642 | 0.062068 | 0.019641 | 0.186856 | 0.161544 |
| SPRY3 | 0.001522 | 0.007289 | 0.01278 | 0.004016 | 0.003472 | 0.00296 | 0.001797 |
| SPRY4 | 0.002323 | 0.009291 | 0.015093 | 0.000288 | 0.001091 | 0.004843 | 0.00471 |
| TGFa | 0.001161 | 0.008088 | 0.000581 | 0.01937 | 0.010097 | 0.320857 | 0.521233 |
| TNC | 0.02352 | 0.003262 | 3.76E−05 | 0.007546 | 0.100134 | 2.14355 | 1.07923 |
| VIM | 78.249 | 21.8566 | 32.6724 | 0.110338 | 19.8353 | 5.38893 | 0.479632 |

| Gene | NCI-H460 | NCI-H520 | NCI-H522 | U-118 | U-251 | U-87 | Y79 |
|---|---|---|---|---|---|---|---|
| AREG | 0.052556 | 0.05329 | 0.111878 | 0.000605 | 0.000065 | 4.3E−06 | 9.9E−06 |
| CA12 | 0.082469 | 0.003906 | 0.010237 | 0.659754 | 0.087172 | 1.02811 | 0.358489 |
| CDH1 | 0.004809 | 0.111105 | 0.005839 | 6.02E−05 | 0.007867 | 0.000181 | 0.000121 |
| DKK3 | 0.017824 | 0.091505 | 0.017098 | 5.20537 | 1.51572 | 0.089003 | 0.00026 |
| DUSP4 | 0.059129 | 0.002668 | 3.73E−05 | 0.000343 | 0.005448 | 0.01468 | 0.001785 |
| DUSP5 | 0.032129 | 0.013697 | 0.016863 | 0.021642 | 0.094732 | 0.06164 | 0.046391 |
| DUSP6 | 0.30566 | 1.49485 | 0.946058 | 0.273573 | 0.63728 | 0.476319 | 0.001491 |
| EGF | 0.07966 | 0.01176 | 5.35E−05 | 0.014885 | 0.15822 | 0.005083 | 2.14E−05 |
| EGFR | 0.11344 | 0.017948 | 0.473029 | 0.673617 | 0.993092 | 0.48971 | 0 |
| ELK3 | 0.055169 | 0.006302 | 0.096055 | 0.368567 | 0.25349 | 0.084788 | 0.008669 |
| ELK4 | 7.62E−05 | 7.41E−05 | 0 | 1.49E−05 | 4.89E−05 | 0.000129 | 4.1E−06 |
| ERBB2 | 0.04181 | 0.049378 | 0.348686 | 0.169575 | 0.111878 | 0.005013 | 0.005962 |
| ERBB3 | 0.001773 | 0.018841 | 0.011518 | 0.002275 | 0.019641 | 0.000416 | 0.001913 |
| EREG | 0.01698 | 3.03E−05 | 0.089622 | 0.034435 | 0.004216 | 0.395021 | 1.44E−05 |
| ETV4 | 0.5 | 0.312083 | 0.266093 | 0.003424 | 0.085971 | 0.026278 | 0.00015 |
| ETV5 | 0.133972 | 0.858565 | 0.056328 | 0.156041 | 1.09429 | 0.271684 | 0.003065 |
| FGF1 | 0.000192 | 0.002137 | 0.001511 | 0.035649 | 0.120742 | NA | 0.000388 |
| FGF10 | 3.55E−05 | 0.000233 | 0.02683 | 0.000236 | 0.000482 | NA | 0 |
| FGF11 | 0.007289 | 0.010672 | 0.072796 | 0.00176 | 0.025033 | 0.003401 | 0.005759 |
| FGF16 | 0.001554 | 0.00176 | 0.000383 | 0.000163 | 0.000225 | NA | 0.000112 |
| FGF17 | 0.000176 | 0.006615 | 0.000288 | 4.14E−05 | 0.002421 | NA | 0.000681 |
| FGF18 | 0.001665 | 0.055939 | 0.002065 | 0.039282 | 0.014378 | NA | 0.004487 |
| FGF19 | 8.22E−05 | 0.447513 | 2.79E−05 | 0 | 0.000167 | NA | 0.000231 |
| FGF2 | 0.162668 | 0.125 | 1.02101 | 0.325336 | 0.456916 | NA | 0.021493 |
| FGF20 | 0 | 0.070805 | 0.000892 | 0.000104 | 0.001362 | NA | 1.27E−05 |
| FGF21 | 5.28E−05 | 0.002022 | 0 | 6.28E−05 | 0.00012 | NA | 0.00002 |
| FGF22 | 0.001913 | 0.028164 | 0.005719 | 0.001848 | 0.006708 | NA | 0.018073 |
| FGF3 | 0 | 3.29436 | 9.6E−06 | 0 | 0 | NA | 7.2E−06 |
| FGF4 | 0 | 0.000147 | 0 | 0 | 0 | NA | 0 |
| FGF5 | 0 | 0.00052 | 0.000042 | 0.230047 | 0.032577 | NA | 5.7E−06 |
| FGF6 | 4.5E−06 | 4.32E−05 | 0 | 4.4E−06 | 1.81E−05 | NA | 6.9E−06 |
| FGF7 | 0.00143 | 0.001106 | 3.07E−05 | 0.00294 | 0.001554 | NA | 7.5E−06 |
| FGF8 | 0.000148 | 0.002197 | 0.001236 | 8.94E−05 | 0 | NA | 0.006172 |
| FGF9 | 0.001106 | 0.217638 | 0.03983 | 0.000886 | 0.001289 | NA | 0.000341 |
| FGFBP1 | 0.000943 | 0.02352 | 6.32E−05 | 0.000113 | 0.000475 | 7.78E−05 | 0.000019 |
| FGFBP2 | 0.002307 | 0.000943 | 0.000977 | 0.001271 | 0.002079 | 0.000502 | 0.000411 |
| FGFBP3 | 0.017824 | 0.008549 | 0.00982 | 0.00639 | 0.007239 | 0.005263 | 0.00128 |
| FGFR1 | 0.101531 | 7.46426 | 4.16986 | 1.25701 | 1.81504 | NA | 0.10083 |
| FGFR1IIIb | 1.47E−05 | 0.11744 | 0.000217 | 0.000104 | 0.000527 | NA | 1.02E−05 |
| FGFR1IIIc | 0.020054 | 2.17347 | 3.83706 | 0.952638 | 0.231647 | NA | 0.032804 |
| FGFR2 | 0.001631 | 0.006003 | 0.004129 | 0.00088 | 0.082469 | NA | 0.044502 |
| FGFR2IIIb | 7.57E−05 | 0.001848 | 0.000462 | 0.000103 | 0.007189 | NA | 0.004876 |
| FGFR2IIIc | 0.000402 | 0.000109 | 0.003853 | 0.000488 | 0.023036 | NA | 0.016516 |
| FGFR3 | 0.004016 | 0.291183 | 0.01937 | 0.002291 | 0.373712 | NA | 0.029977 |
| FGFR3IIIb | 5.35E−05 | 0.049378 | 0.00044 | 1.12E−05 | 0.010672 | NA | 0.000756 |
| FGFR3IIIc | 0.000136 | 0.000299 | 0.002981 | 1.55E−05 | 0.021051 | NA | 0.000899 |
| FGFR4 | 0.000715 | 0.007041 | 0.001047 | 7.16E−05 | 0.001748 | NA | 0.006003 |
| FLRT1 | 0.0625 | 0.020475 | 0.012517 | 0.001848 | 0.016747 | 0.006434 | 0.015625 |
| FLRT2 | 0.395021 | 0.001381 | 0.006944 | 0.329877 | 0.033262 | 0.084788 | 0.007239 |
| FLRT3 | 0.000618 | 0.000074 | 0.00072 | 0 | 0 | 0.002108 | 0.000223 |
| HGF | 2.87E−05 | 0.007391 | 0.011679 | 1.19748 | 0.000411 | 1.32869 | 2.01E−05 |
| IGF1 | 0 | 5.02805 | 0.001689 | 0.070805 | 0.015303 | 0.00471 | 0.000226 |
| IGF1R | 0.368567 | 0.028956 | 1.34723 | 0.041521 | 0.668964 | 0.052193 | 0.142595 |
| IGF2 | 0.008258 | 0.00357 | 0.05872 | 0.097396 | 0.000459 | 0.000197 | 0.035649 |
| KDR | 0.007705 | 0.001145 | 0.000196 | 0.001228 | 0.003308 | 0.000108 | 0.00004 |
| MET | 0.262429 | 0.066064 | 0.089622 | 1.3566 | 0.366021 | 0.697372 | 0.00088 |
| MMP1 | 0.00639 | 0.000125 | 0.033493 | 0.104386 | 0.003906 | 0.049378 | 5.4E−06 |
| MMP2 | 0.006708 | 0.139661 | 0.003545 | 5.61778 | 2.37841 | 10.9283 | 0.001289 |
| NCAM1 | 0.022251 | 0.02836 | 8.7E−06 | 0.000446 | 0.125 | 0.004016 | 0.030186 |

TABLE 7-continued

Gene expression values for certain xenograft models from Table 5.

| | | | | | | | |
|---|---|---|---|---|---|---|---|
| PDGFRa | 0 | 0.001325 | 0.005759 | 1.07177 | 0.650671 | 0.120742 | 0.000121 |
| PDGFRb | 0.021945 | 0.00148 | 0.002152 | 3.50642 | 0 | 1.28343 | 0.000338 |
| PLAU | 0.011598 | 0.000226 | 0.021493 | 1.46409 | 0.933033 | 2.56685 | 8.57E−05 |
| PLAUR | 0.098755 | 0.022718 | 0.003826 | 0.190782 | 0.939523 | 0.933033 | 0.041235 |
| SERPINE1 | 0.044811 | 0.010027 | 0.003002 | 1.54756 | 3.53081 | 2.2974 | 2.46E−05 |
| SOX9 | 0.535887 | 0.496546 | 0.02797 | 0.119908 | 3.34035 | 0.30566 | 0.000983 |
| SPRY1 | 0.010097 | 0.001532 | 0.334482 | 0.070316 | 0.092783 | 0.003496 | 0.019505 |
| SPRY2 | 0.028956 | 0.115024 | 0.008851 | 0.092783 | 0.432269 | 0.351111 | 0.017458 |
| SPRY3 | 0.046391 | 0.015517 | 0.001785 | 0.001598 | 0.009291 | 0.007813 | 0.004425 |
| SPRY4 | 0.00181 | 0.007239 | 0.002668 | 0.002065 | 0.002879 | 0.002197 | 0.00012 |
| TGFa | 0.001665 | 0.099442 | 0.021793 | 0.002259 | 0.266093 | 0.024689 | 0.000296 |
| TNC | 0 | 0.000531 | 0.001609 | 2.62079 | 2.32947 | 4.02782 | 0.000341 |
| VIM | 13.0864 | 2.71321 | 5.1337 | 31.3414 | 48.1679 | 22.4711 | 0.790041 |

The invention claimed is:

1. A method of treating lung cancer having a fibroblast growth factor receptor 1 (FGFR1) gene amplification in a subject, wherein at least a portion of the cells of the lung cancer having an FGFR1 gene amplification have a ratio of FGFR1 gene to chromosome 8 centromere of at least 1.5, comprising:
administering a therapeutically effective amount of an FGFR1 extracellular domain (ECD) or an FGFR1 ECD fusion molecule to the subject.

2. A method of treating lung cancer having a fibroblast growth factor receptor 1 (FGFR1) gene amplification in a subject, comprising administering a therapeutically effective amount of an FGFR1 extracellular domain (ECD) or an FGFR1 ECD fusion molecule to the subject, wherein, prior to administration of the FGFR1 ECD or FGFR1 ECD fusion molecule, at least a portion of the cells of the lung cancer have been determined to have a ratio of FGFR1 gene to chromosome 8 centromere of at least 1.5.

3. The method of claim 1, wherein at least a portion of the cells of the lung cancer having an FGFR1 gene amplification comprise at least three copies of the FGFR1 gene.

4. The method of claim 2, wherein FGFR1 gene amplification was determined by a method selected from fluorescence in situ hybridization, array comparative genomic hybridization, DNA microarray, spectral karyotyping, quantitative PCR, southern blotting, or sequencing.

5. The method of claim 1, wherein the cancer overexpresses at least one, at least two, at least three, at least four, or five markers selected from FGFR1, FGFR3IIIc, DKK3, FGF18, and ETV4.

6. The method of claim 5, wherein the cancer overexpresses FGFR1IIIc.

7. The method of claim 5, wherein the overexpression is protein overexpression.

8. The method of claim 7, wherein protein overexpression is determined using immunohistochemistry.

9. The method of claim 5, wherein the overexpression is mRNA overexpression.

10. The method of claim 9, wherein mRNA overexpression is determined using quantitative RT-PCR.

11. The method of claim 1, wherein the method comprises administering an FGFR1 ECD.

12. The method of claim 11, wherein the FGFR1 ECD comprises an amino acid sequence selected from SEQ ID NOs: 1 to 4.

13. The method of claim 1, wherein the method comprises administering an FGFR1 ECD fusion molecule.

14. The method of claim 13, wherein the FGFR1 ECD fusion molecule comprises an FGFR1 ECD and a fusion partner, and wherein the fusion partner is Fc.

15. The method of claim 14, wherein the FGFR1 ECD fusion molecule comprises the amino acid sequence of SEQ ID NO: 5.

16. The method of claim 14, wherein the FGFR1 ECD fusion molecule comprises the amino acid sequence of SEQ ID NO: 6.

17. The method of claim 1, wherein the lung cancer is small cell lung cancer (SCLC).

18. The method of claim 1, wherein the lung cancer is non-small cell lung cancer (NSCLC).

19. The method of claim 1, further comprising administering paclitaxel and carboplatin to the subject.

20. A method of treating non-small cell lung cancer (NSCLC) having a fibroblast growth factor receptor (FGFR1) gene amplification in a subject, wherein at least a portion of the cells of the cancer having an FGFR1 gene amplification have a ratio of FGFR1 gene to chromosome 8 centromere of at least 1.5, comprising:
   administering a therapeutically effective amount of an FGFR1 extracellular domain (ECD) fusion molecule comprising the amino acid sequence of SEQ ID NO: 6, paclitaxel, and carboplatin to the subject.

* * * * *

SEQUENCE LISTING

<160> NUMBER OF SEQ ID NOS: 10

<210> SEQ ID NO 1
<211> LENGTH: 374
<212> TYPE: PRT
<213> ORGANISM: Artificial sequence
<220> FEATURE:
<223> OTHER INFORMATION: Synthetic

<400> SEQUENCE: 1

```
Met Trp Ser Trp Lys Cys Leu Leu Phe Trp Ala Val Leu Val Thr Ala
1               5                  10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
```

```
            245                 250                 255
Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
            275                 280                 285

Lys His Ile Glu Val Asn Gly Ser Lys Ile Gly Pro Asp Asn Leu Pro
            290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
                340                 345                 350

Trp Leu Thr Val Leu Glu Ala Leu Glu Glu Arg Pro Ala Val Met Thr
                355                 360                 365

Ser Pro Leu Tyr Leu Glu
            370

<210> SEQ ID NO 2
<211> LENGTH: 353
<212> TYPE: PRT
<213> ORGANISM: Artificial sequence
<220> FEATURE:
<223> OTHER INFORMATION: Synthetic

<400> SEQUENCE: 2

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
                20                  25                  30

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
        50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
```

```
                225                 230                 235                 240
Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
                260                 265                 270

Asn Gly Ser Lys Ile Gly Pro Asp Asn Leu Pro Tyr Val Gln Ile Leu
                275                 280                 285

Lys Thr Ala Gly Val Asn Thr Thr Asp Lys Glu Met Glu Val Leu His
                290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Pro Ala Val Met Thr Ser Pro Leu Tyr Leu
                340                 345                 350

Glu

<210> SEQ ID NO 3
<211> LENGTH: 360
<212> TYPE: PRT
<213> ORGANISM: Artificial sequence
<220> FEATURE:
<223> OTHER INFORMATION: Synthetic

<400> SEQUENCE: 3

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
                35                  40                  45

Asp Leu Leu Gln Leu Arg Cys Arg Leu Arg Asp Asp Val Gln Ser Ile
                50                  55                  60

Asn Trp Leu Arg Asp Gly Val Gln Leu Ala Glu Ser Asn Arg Thr Arg
65              70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
                100                 105                 110

Tyr Phe Ser Val Asn Val Ser Asp Ala Leu Pro Ser Ser Glu Asp Asp
                115                 120                 125

Asp Asp Asp Asp Asp Ser Ser Ser Glu Glu Lys Glu Thr Asp Asn Thr
                130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
                180                 185                 190

Lys Glu Phe Lys Pro Asp His Arg Ile Gly Gly Tyr Lys Val Arg Tyr
                195                 200                 205

Ala Thr Trp Ser Ile Ile Met Asp Ser Val Val Pro Ser Asp Lys Gly
                210                 215                 220

Asn Tyr Thr Cys Ile Val Glu Asn Glu Tyr Gly Ser Ile Asn His Thr
225                 230                 235                 240
```

Tyr Gln Leu Asp Val Val Glu Arg Ser Pro His Arg Pro Ile Leu Gln
            245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
            275                 280                 285

Lys His Ile Glu Val Asn Gly Ser Lys Ile Gly Pro Asp Asn Leu Pro
            290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
            325                 330                 335

Tyr Thr Cys Leu Ala Gly Asn Ser Ile Gly Leu Ser His His Ser Ala
            340                 345                 350

Trp Leu Thr Val Leu Glu Ala Leu
            355                 360

<210> SEQ ID NO 4
<211> LENGTH: 339
<212> TYPE: PRT
<213> ORGANISM: Artificial sequence
<220> FEATURE:
<223> OTHER INFORMATION: Synthetic

<400> SEQUENCE: 4

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
        50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
            85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
            115                 120                 125

Ala Pro Tyr Trp Thr Ser Pro Glu Lys Met Glu Lys Lys Leu His Ala
            130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
            165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
            195                 200                 205

Val Glu Asn Glu Tyr Gly Ser Ile Asn His Thr Tyr Gln Leu Asp Val
            210                 215                 220

Val Glu Arg Ser Pro His Arg Pro Ile Leu Gln Ala Gly Leu Pro Ala
225                 230                 235                 240

```
Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu

<210> SEQ ID NO 5
<211> LENGTH: 592
<212> TYPE: PRT
<213> ORGANISM: Artificial sequence
<220> FEATURE:
<223> OTHER INFORMATION: Synthetic

<400> SEQUENCE: 5

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255
```

Ala Gly Leu Pro Ala Asn Lys Thr Val Ala Leu Gly Ser Asn Val Glu
                260                 265                 270

Phe Met Cys Lys Val Tyr Ser Asp Pro Gln Pro His Ile Gln Trp Leu
            275                 280                 285

Lys His Ile Glu Val Asn Gly Ser Lys Ile Gly Pro Asp Asn Leu Pro
        290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Pro Lys Ser Ser Asp Lys Thr
        355                 360                 365

His Thr Cys Pro Pro Cys Pro Ala Pro Glu Leu Leu Gly Gly Pro Ser
    370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
            420                 425                 430

Lys Thr Lys Pro Arg Glu Glu Gln Tyr Asn Ser Thr Tyr Arg Val Val
        435                 440                 445

Ser Val Leu Thr Val Leu His Gln Asp Trp Leu Asn Gly Lys Glu Tyr
450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590

<210> SEQ ID NO 6
<211> LENGTH: 571
<212> TYPE: PRT
<213> ORGANISM: Artificial sequence
<220> FEATURE:
<223> OTHER INFORMATION: Synthetic

<400> SEQUENCE: 6

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
                20                  25                  30

-continued

```
Arg Cys Arg Leu Arg Asp Asp Val Gln Ser Ile Asn Trp Leu Arg Asp
         35                  40                  45
Gly Val Gln Leu Ala Glu Ser Asn Arg Thr Arg Ile Thr Gly Glu Glu
 50                  55                  60
Val Glu Val Gln Asp Ser Val Pro Ala Asp Ser Gly Leu Tyr Ala Cys
 65                  70                  75                  80
Val Thr Ser Ser Pro Ser Gly Ser Asp Thr Thr Tyr Phe Ser Val Asn
             85                  90                  95
Val Ser Asp Ala Leu Pro Ser Ser Glu Asp Asp Asp Asp Asp Asp Asp
            100                 105                 110
Ser Ser Ser Glu Glu Lys Glu Thr Asp Asn Thr Lys Pro Asn Pro Val
            115                 120                 125
Ala Pro Tyr Trp Thr Ser Pro Glu Lys Met Glu Lys Lys Leu His Ala
            130                 135                 140
Val Pro Ala Ala Lys Thr Val Lys Phe Lys Cys Pro Ser Ser Gly Thr
145                 150                 155                 160
Pro Asn Pro Thr Leu Arg Trp Leu Lys Asn Gly Lys Glu Phe Lys Pro
                165                 170                 175
Asp His Arg Ile Gly Gly Tyr Lys Val Arg Tyr Ala Thr Trp Ser Ile
                180                 185                 190
Ile Met Asp Ser Val Val Pro Ser Asp Lys Gly Asn Tyr Thr Cys Ile
            195                 200                 205
Val Glu Asn Glu Tyr Gly Ser Ile Asn His Thr Tyr Gln Leu Asp Val
            210                 215                 220
Val Glu Arg Ser Pro His Arg Pro Ile Leu Gln Ala Gly Leu Pro Ala
225                 230                 235                 240
Asn Lys Thr Val Ala Leu Gly Ser Asn Val Glu Phe Met Cys Lys Val
                245                 250                 255
Tyr Ser Asp Pro Gln Pro His Ile Gln Trp Leu Lys His Ile Glu Val
                260                 265                 270
Asn Gly Ser Lys Ile Gly Pro Asp Asn Leu Pro Tyr Val Gln Ile Leu
            275                 280                 285
Lys Thr Ala Gly Val Asn Thr Thr Asp Lys Glu Met Glu Val Leu His
            290                 295                 300
Leu Arg Asn Val Ser Phe Glu Asp Ala Gly Glu Tyr Thr Cys Leu Ala
305                 310                 315                 320
Gly Asn Ser Ile Gly Leu Ser His His Ser Ala Trp Leu Thr Val Leu
                325                 330                 335
Glu Ala Leu Glu Pro Lys Ser Ser Asp Lys Thr His Thr Cys Pro Pro
                340                 345                 350
Cys Pro Ala Pro Glu Leu Leu Gly Gly Pro Ser Val Phe Leu Phe Pro
            355                 360                 365
Pro Lys Pro Lys Asp Thr Leu Met Ile Ser Arg Thr Pro Glu Val Thr
            370                 375                 380
Cys Val Val Val Asp Val Ser His Glu Asp Pro Glu Val Lys Phe Asn
385                 390                 395                 400
Trp Tyr Val Asp Gly Val Glu Val His Asn Ala Lys Thr Lys Pro Arg
                405                 410                 415
Glu Glu Gln Tyr Asn Ser Thr Tyr Arg Val Val Ser Val Leu Thr Val
                420                 425                 430
Leu His Gln Asp Trp Leu Asn Gly Lys Glu Tyr Lys Cys Lys Val Ser
            435                 440                 445
Asn Lys Ala Leu Pro Ala Pro Ile Glu Lys Thr Ile Ser Lys Ala Lys
```

-continued

```
            450                 455                 460
Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
            515                 520                 525

Phe Leu Tyr Ser Lys Leu Thr Val Asp Lys Ser Arg Trp Gln Gln Gly
            530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 7
<211> LENGTH: 21
<212> TYPE: PRT
<213> ORGANISM: Artificial sequence
<220> FEATURE:
<223> OTHER INFORMATION: Synthetic

<400> SEQUENCE: 7

Met Trp Ser Trp Lys Cys Leu Leu Phe Trp Ala Val Leu Val Thr Ala
1               5                   10                  15

Thr Leu Cys Thr Ala
            20

<210> SEQ ID NO 8
<211> LENGTH: 232
<212> TYPE: PRT
<213> ORGANISM: Artificial sequence
<220> FEATURE:
<223> OTHER INFORMATION: Synthetic

<400> SEQUENCE: 8

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 9
<211> LENGTH: 228
<212> TYPE: PRT
<213> ORGANISM: Artificial sequence
<220> FEATURE:
<223> OTHER INFORMATION: Synthetic

<400> SEQUENCE: 9

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 10
<211> LENGTH: 229
<212> TYPE: PRT
<213> ORGANISM: Artificial sequence
<220> FEATURE:
<223> OTHER INFORMATION: Synthetic

<400> SEQUENCE: 10

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
        210                 215                 220

Leu Ser Leu Gly Lys
225
```